US008604174B2

(12) United States Patent
Babcook et al.

(10) Patent No.: US 8,604,174 B2
(45) Date of Patent: Dec. 10, 2013

(54) HIGH AFFINITY FULLY HUMAN MONOCLONAL ANTIBODIES TO INTERLEUKIN-8

(75) Inventors: John Babcook, Vancouver (CA); Palaniswami Rathanaswami, Vancouver (CA); Orit Foord, Foster City, CA (US); Jaspal S. Kang, Surrey (CA)

(73) Assignee: Amgen Inc., Thousand Oaks, CA (US)

( * ) Notice: Subject to any disclaimer, the term of this patent is extended or adjusted under 35 U.S.C. 154(b) by 1440 days.

(21) Appl. No.: 11/911,940

(22) PCT Filed: Apr. 18, 2006

(86) PCT No.: PCT/US2006/014440
§ 371 (c)(1),
(2), (4) Date: Apr. 16, 2008

(87) PCT Pub. No.: WO2006/113643
PCT Pub. Date: Oct. 26, 2006

(65) Prior Publication Data
US 2009/0130110 A1    May 21, 2009

Related U.S. Application Data

(60) Provisional application No. 60/473,452, filed on Apr. 20, 2005.

(51) Int. Cl.
*C07K 16/24*     (2006.01)
*A61K 39/00*     (2006.01)
*A61K 39/395*    (2006.01)

(52) U.S. Cl.
USPC .............. 530/388.23; 424/142.1; 424/158.1

(58) Field of Classification Search
None
See application file for complete search history.

(56) References Cited

U.S. PATENT DOCUMENTS

| 3,935,074 | A | * | 1/1976 | Rubenstein et al. ........... 435/7.9 |
| 5,686,070 | A | | 11/1997 | Doerschuk et al. |
| 5,707,622 | A | | 1/1998 | Fong et al. |
| 5,874,080 | A | * | 2/1999 | Hebert et al. .............. 424/145.1 |
| 5,939,598 | A | | 8/1999 | Kucherlapati et al. |
| 6,075,181 | A | | 6/2000 | Kucherlapati et al. |
| 6,114,598 | A | | 9/2000 | Kucherlapati et al. |
| 6,150,584 | A | | 11/2000 | Kucherlapati et al. |
| 6,162,963 | A | | 12/2000 | Kucherlapati et al. |
| 6,713,610 | B1 | | 3/2004 | Kucherlapati et al. |
| 7,282,568 | B2 | | 10/2007 | Teeling et al. |
| 2003/0232048 | A1 | | 12/2003 | Yang et al. |

FOREIGN PATENT DOCUMENTS

| EP | 0 463 151 B1 | 6/1996 |
| EP | 0822830 | 4/2008 |
| JP | 3 068 180 82 | 7/2000 |
| JP | 3 068 506 82 | 7/2000 |
| JP | 3 068 507 82 | 7/2000 |
| WO | WO 94/02602 | 2/1994 |
| WO | WO 96/33735 | 10/1996 |
| WO | WO 96/34096 | 10/1996 |
| WO | WO 98/24893 | 6/1998 |
| WO | WO 98/37200 A2 | 8/1998 |
| WO | WO 00/76310 | 12/2000 |
| WO | WO 01/25492 A1 | 4/2001 |
| WO | WO 01/40306 A1 | 6/2001 |
| WO | WO 03/047336 | 6/2003 |
| WO | WO 03/048730 A2 | 6/2003 |
| WO | WO 2004/058797 A2 | 7/2004 |
| WO | WO 2006/113643 A2 | 10/2006 |

OTHER PUBLICATIONS

Rudikoff et al, 1982, Proc Natl Acad Sci, vol. 79 p. 1979-1983.*
MacCallum et al. J. Mol. Biol. (1996) 262,732-745.*
Pascalis et al., The Journal of Immunology (2002) 169, 3076-3084.*
Casset et al., 2003, Biochemical and Biophysical Research Communications 307, 198-205.*
Vajdos et al., 2002, J. Mol. Biol., 320, 415-428.*
Holm et al., 2007, Mol. Immunol, 44, 1075-1084.*
Chen et al., 1999, J. Mol. Bio. 293, 865-881.*
Wu et al., 1999, J. Mol. Biol. 294, 151-162.*
Adams, G.P. and Schier, R., "Generating improved single-chain Fv molecules for tumor targeting," *J. Immunol. Methods* 231, 249-260 (1999).
Ajuebor et al., *Immunology* 105(2):137-43 (2002).
Babcook et al., "A novel strategy for generating monoclonal antibodies from single, isolated lymphocytes producing antibodies of defined specifities," *Proc. Natl. Acad. Sci. USA* 93, 7843-7848 (1996).
Balint et al. "Antibody engineering by parsimonious mutagenesis," *Gene* (1993) 137(1): 109-118.
Barbas, C.F. III and Burton, D.R., "Selection and evolution of high-affinity human anti-viral antibodies," *Trends Biotechnol* 14, 230-234 (1996).
Batista F.D. and Neuberger, M.S., "Affinity dependence of the B cell response to antigen: a threshold, a ceiling, and the importance of off-rate," *Immunity* 8, 751-759 (1998).
Biasi et al., "Neutrophil functions and IL-8 in psoriatic arthritis and in cutaneous psoriasis," *Inflammation* 22, 533-543 (1998).
Blake et al., "Automated kinetic exclusion assays to quantify protein binding interactions in homogeneous solution," *Anal. Biochem.* 282, 123-124 (1999).
Boder et al., "Directed evolution of antibody fragments with monovalent femtomolar antigen-binding affinity," *Proc. Natl. Acad. Sci. USA* 97, 10701-10705 (2000).
Burrows et al., "Determination of the monomer-dimer equilibrium of interleukin-8 reveals it is a monomer at physiological concentrations," *Biochemistry* 33, 12741-12745 (1994).
Cauerhff et al., "Structural mechanism for affinity maturation of an anti-lysozyme antibody," *Proc. Natl. Acad. Sci. USA* 101, 3539-3544 (2004).

(Continued)

*Primary Examiner* — Robert Landsman
*Assistant Examiner* — Bruce D Hissong
(74) *Attorney, Agent, or Firm* — Melissa A. Shaw

(57) ABSTRACT

The present embodiments are related to high-affinity antibodies directed to IL-8, methods of making and characterizing such antibodies and uses of such antibodies. Isolated polynucleotide sequences encoding, and amino acid sequences comprising, heavy and light chain immunoglobulin molecules, particularly sequences corresponding to contiguous heavy and light chain sequences spanning the framework regions (FR's) and/or complementarity determining regions (CDR's), are provided.

7 Claims, 18 Drawing Sheets

(56) References Cited

OTHER PUBLICATIONS

Checovich et al., "Fluorescence polarization—a new tool for cell and molecular biology," *Nature* 375, 254-256 (1995).

Chen et al., "Selection and analysis of an optimized anti-VEGB antibody: crystal structure of an affinity-matured Fab in complex with antigen," *J. Mol. Biol.* 293, 865-881 (1999).

De Haard, "A large non-immunized human Fab fragment phage library that permits rapid isolation and kinetic analysis of high affinity antibodies," *J. Biol. Chem.* 274, 18218-18230 (1999).

Dinarello et al., *JAMA*, 269(14):1829-35 (1993).

Drake et al., "Characterizing high-affinity antigen/antibody complexes by kinetic- and equilibrium-based methods," *Anal. Biochem.* 328, 35-43 (2004).

Ferrante, A. and Thong, Y.H., "A Rapid One-Step Procedure for Purification of Mononuclear and Polymorphonuclear Leukocytes from Human Blood Using a Modification of the Hypaque-Ficoll Technique," *J. Immunol. Methods* 24:389-393 (1978).

Foote et al., "Kinetic and affinity limits on antibodies produce during immune response," *Proc. Natl. Acad. Sci. USA* 92, 1254-1256 (1995).

Green and Jakobovits, *J. Exp. Med.* 188:483-495 (1998).

Green, L.L., "Antibody engineering via genetic engineering of the mouse: XenoMouse strains are a vehicle for the facile generation of therapeutic human monoclonal antibodies," *J. Immunol. Methods*, 231, 11-23 (1999).

Griffiths et al., "Isolation of high affinity human antibodies directly from large synthetic repertoires," *EMBO J.* 13, 3245-3260 (1994).

Hanes et al., "Picomolar affinity antibodies from a fully synthetic naïve library selected and evolved by ribosome display," *Nat. Biotechnol.* 18, 1287-1292 (2000).

Imada et al., *Scand J Gastroenterol*, 36(8):854-64 (2001).

International Search Report, International Application No. PCT/US2006/014440, dated Jul. 16, 2007.

Jiang et al., *Int J Dermatol*., 40(11):699-703 (2001).

Johnson, S., Griego, S. D., Pfarr, D. S., Doyle, M. L., Woods, R., Carlin, D., Prince, G. A., Koenig, S., Young, J. F. & Dillon, S. B. (1999) J Infect Dis 180, 35-40.

Jonsson et al., "Real-time biospecific interaction analysis using surface plasmon resonance and a sensor chip technology," *Biotechniques* 11, 620-627 (1991).

Joss et al., "Interpreting kinetic rate constants from optical biosensor data recorded on a decaying surface," *Anal. Biochem.* 261, 203-210 (1998).

Kitadai et al. "Expression of Interleukin-8 Correlates with Vascularity in Human Gastric Carcinoma," Amer. J. Pathol. Oct. 1997, vol. 152, No. 1, pp. 93-100.

Li et al., "Antibodies highly effective in Scid mice during infection by the intracellular bacterium," *Ehrlichia chaffeensis* are of picomolar affinity and exhibit preferential epitope and isotype utilization, *J. Immunol.* 169, 1419-1415 (2002).

Lowe et al., "New approaches for the analysis of molecular recognition using the lasys evanescent wave biosensor," *J. Mol. Recognit.* 11, 194-199 (1998).

Lynch et al., *Am Rev Respir Dis*., 145(6):1433-9 (1992).

Marks, J.D., "Deciphering antibody properties that lead to potent botulinum neurotoxin neutralization," *Mov. Disord.* 19 (Suppl. 8) S101-S108 (2004).

Matsumoto et al., *J. Leukoc. Biol.*, 62(5):581-7 (1997).

McCall, A. M., Shahied, L., Amoroso, A. R., Horak, E. M., Simmons, H. H., Nielson, U., Adams, G. P., Schier, R., Marks, J. D. & Weiner, L. M. (2001) J Immunol 166, 6112-7.

Mendez et al., *Nature Genetics* 15:146-156 (1997).

Myszka, D.G., "Kinetic analysis of macromolecular interactions using surface plasmon resonance biosensors," *Curr. Opin. Biotechnol.* 8, 50-57 (1997).

Paolini et al., "The chemokines IL-8, monocyte chemoattractant protein-1, and I-309 are monomers at physiologically relevant concentrations," *J. Immunol.* 153, 2704-2717 (1994).

Rathanaswami et al., "Demonstration of an in vivo generated sub-picomolar affinity fully human monoclonal antibody to interleukin-8," *Biochemical and Biophysical Research Communications*, 334, 1004-1013 (2005).

Reich et al., *J Invest Dermatol*, 116(2):319-29 (2001) (identified as Kraan et al. in specification).

Schier et al., "Isolation of picomolar affinity anti-c-erbB-2 single-chain Fv by molecular evolution of the complementarity determining regions in the center of the antibody binding site," *J. Mol. Biol.* 263, 551-567 (1996).

Schreiber et al. "Rapid, electrostatically assisted association of proteins," Nat. Struct. Biol. 3 (1996) 427-431.

Sheets, M. D., Amersdorfer, P., Finnern, R., Sargent, P., Lindquist, E., Schier, R., Hemingsen, G., Wong, C., Gerhart, J. C., Marks, J. D. & Lindqvist, E. (1998) Proc Natl Acad Sci U S A 95, 6157-62.

Singh et al., *Histol Histopathol*, 15(3):843-9 (2000).

Vaughan et al., "Human antibodies with sub-nanomolar affinities isolated from a large non-immunized phage display library," *Nat. Biotechnol.*, 14, 309-314 (1996).

Watts, C. and Davidson, H.W., *EMBO J.*, 7:1937-45 (1998).

Xie et al., *Cytokine Growth Factor Rev.*, 12(4):375-91 (2001).

Yang et al., *J. Leukoc. Biol.* 66(3):401-410 (1999).

Yang, W. P., Green, K., Pinz-Sweeney, S., Briones, A. T., Burton, D. R. & Barbas, C. F., 3rd (1995) J Mol Biol 254, 392-403.

Zhu et al., Inhibition of human leukemia in an animal model with human antibodies directed against vascular endothelial growth factor receptor 2. Correctional between antibody affinity and biological activity. *Leukemia* 17, 604-611 (2003).

Zuckier et al, "Influence of affinity and antigen density on antibody localization in a modifiable tumor targeting model," *Cancer Res.* 60 7008-7013 (2000).

Extended European Search Report dated Aug. 25, 2010, received in European Patent Application No. 06750468.8.

File History, US Patent No. 6,713,610, issued Mar. 30, 2004.

Huang, et al., "Fully humanized neutralizing antibodies to interleukin-8 (ABX-IL8) inhibit angiogenesis, tumor growth, and metastasis of human melanoma." American Journal of Pathology, vol. 161, No. 1, (Jul. 2002): pp. 125-134.

Leong, S.R. et al., "Adapting pharmacokinetic properties of a humanized anti-interleukin-8 antibody for therapeutic applications using site-specific pegylation." *Cytokine*, vol. 16, No. 3, (Nov. 7, 2001): pp. 106-119.

Rathanaswami et al., "Demonstration of an in vivo generated sub-picomolar affinity fully human monoclonal antibody to interleukin-8", Biochem Biodlys Res Common, 334(4):1004-4013, 2005.

U.S. Appl. No. 07/466,008, filed Jan. 12, 1990, Kucherlapati et al.
U.S. Appl. No. 07/610,515, filed Nov. 8, 1990, Kucherlapati et al.
U.S. Appl. No. 07/919,297, filed Jul. 24, 1992, Kucherlapati et al.
U.S. Appl. No. 07/922,649, filed Jul. 30, 1992, Kucherlapati et al.
U.S. Appl. No. 08/031,801, filed Mar. 15, 1993, Kucherlapati et al.
U.S. Appl. No. 08/112,848, filed Aug. 27, 1993, Kucherlapati et al.
U.S. Appl. No. 08/234,145, filed Apr. 28, 1994, Kucherlapati et al.
U.S. Appl. No. 08/376,279, filed Jan. 20, 1995, Jakobovits et al.
U.S. Appl. No. 08/430,938, filed Apr. 27, 1995, Kucherlapati et al.
U.S. Appl. No. 08/462,513, filed Jun. 5, 1995, Kucherlapati et al.
U.S. Appl. No. 08/462,837, filed Jun. 5, 1995, Kucherlapati et al.
U.S. Appl. No. 08/463,191, filed Jun. 5, 1995, Kucherlapati et al.
U.S. Appl. No. 08/464,582, filed Jun. 5, 1995, Kucherlapati et al.
U.S. Appl. No. 08/464,584, filed Jun. 5, 1995, Jakobovits et al.
U.S. Appl. No. 08/486,853, filed Jun. 5, 1995, Kucherlapati et al.
U.S. Appl. No. 08/486,857, filed Jun. 5, 1995, Kucherlapati et al.
U.S. Appl. No. 08/486,859, filed Jun. 5, 1995, Kucherlapati et al.
U.S. Appl. No. 08/724,752, filed Oct. 2, 1996, Kucherlapati et al.
U.S. Appl. No. 08/759,620, filed Dec. 3, 1996, Jakobovits et al.

* cited by examiner

Anti-IL8 mAb 33 Vk  (Seq. ID No: 1)
DIVMTQSPDSLAVSLGERATINCMSSQSLLYSSNNKNYLAWYQQKPGQPPKLLIYWASTRESGV
PDRFSGSGSGTDFTLTISSLQAEDVAVYYCQQYYGTPLTFGGGTKVEIK

Anti-IL8 mAb 33 Vh  (Seq. ID No: 3)
QVQLQQWGAGLLKPSETLSLTCAVYGGFFSGYYWSWIRQPPGKGLEWIGEINHSGSTNYNPSLK
SRVTISVDTSKNQFSLKLISVTAADTAVYYCARGSAAEAFDIWGQGTMVTVSS

Anti-IL8 mAb 142 Vk  (Seq. ID No: 5)
DIQMTQSPSSLSASVGDRVTITCRASQGISNSLAWYQQKPGKVPNLLIYAASTLQSGVPSRFSG
SGSGTDFTLTISSLQPEDVATYYCQKYNSVPLTFGGGTKVEIK

Anti-IL8 mAb 142 Vh  (Seq. ID No: 7)
QVQLVQSGAEVKKPGASVKVSCKASGYTFTGYYMHWVRQAPGQGLEWMGWINSNSGGTNYSQKF
QGRVTMTRDTSISTVYMELSRLRSDDTAVYYCASGYSYGYRYYYYGMDVWGQGTTVTVSS

Anti-IL8 mAb 203 Vk  (Seq. ID No: 9)
DIQMTQSPSSLSASVGDRVTITCRASQGISNSLAWYQQKPGKVPKLLIYAASTLQSGVPSRFSG
SGSGTDFTLTISSLQPEDVATYYCQKYNSVPLTFGGGTKVEIN

Anti-IL8 mAb 203 Vh  (Seq. ID No: 11)
QVQLVQSGAEVKKPGASVKVSCKASGYTFTGYYIHWVRQAPGQGLEWMGWINSNSGGTNFAQKF
QGRVTMTRDTSISTAYMELSRLRPDDTAVYYCASGYRYGYRYYYYGMDVWGQGTTVTVSS

Anti-IL8 mAb 215 Vk  (Seq. ID No: 13)
EIVLTQSPGTLSLSPGERATLSCRASQNVSSSYLAWYQQKPGQAPRLLIYGASSRATGIPDRFS
GSGSGTDFTLTISRLEPEDFAVYYCQQYGSSFTFGPGTKVDIK

Anti-IL8 mAb 215 Vh  (Seq. ID No: 15)
QVQLVESGGGVVQPGRSLRLSCAASGFTFSSYGMHWVRQAPGKGLEWVADISYDGSNKYYADSV
KGRFTISRDNSKNTLYLQMNSLRAEDTAVYYCARDRIAVLDYWGQGTLVTVSS

Anti-IL8 mAb 469 Vk  (Seq. ID No: 17)
DIQMTQSPSSLSASVGDRVTIACRASQGIRNDLGWYQQKPGKAPKRLIYAASSLQSGVPSRFGG
SGSGTEFTLTISSLQPEDFATYYCLQHNSYPRTFGQGTKVEIK

Anti-IL8 mAb 469 Vh  (Seq. ID No: 19)
EVQLLESGGGLVQPGGSLRLSCAASGFTFSSYVMSWVRQAPGKGLEWVSAINNSGGSTDYADSV
KGRFTISRDNSKNTLYLQMNSLRAEDTAVYYCAKEGRFLEWSLYGLDVWGQGTTVTVSS

*FIG. 1A*

Anti-IL8 mAb 809 Vk   (Seq. ID No: 21)
EIVLTQSPGTLSLSPGERATLSCRASQSVSSSYLAWYQQKPGQAPRLLIYGASSRATGIPDRFS
GSGSGTDFTLTISRLEPEDFAVYYCQQYGSSFTFGPGTKVDIK

Anti-IL8 mAb 809 Vh   (Seq. ID No: 23)
QVQLVESGGGVVQPGRSLRLSCAASGFTFSSYGMLWVRQAPGKGLEWVADISYDGSNKYYADSV
KGRFTISRDNSKNTLFLQMNSLRAEDTAVYYCARDRIAVADYWGQGTLVTVSS

Anti-IL8 mAb 837 Vk   (Seq. ID No: 25)
DIVLTQSPDSLVVSLGERATINCKSSQSVLFSSNNRKYLAWYQQKTGQPPKLLIYWASTRESGV
PDRFSGSGSGTDFTLTISSLQAEDVAVYYCQQYYSTPFTFGGGTKVEIK

Anti-IL8 mAb 837 Vh   (Seq. ID No: 27)
QVQLQQWGAGLLKPSETLSLTCAVFGGTFSGYYWTWIRQPPGKGLEWIGEVIHHGSTNYSPSLK
SRVTISADTSKSQFSLRLSSVTAADTAVYYCARGGAAAALDSWGQGTLVIVSS

Anti-IL8 mAb 861 Vk   (Seq. ID No: 29)
EIVLTQSPGTLSLSPGERATLSCRASQTIDYNYLHWYQQKPGQAPRLLIYGTFIRATVIPDRFS
GSGSGTDFTLTISRLEPEDIAVYYCQQFGRSPLTFGGGTKVEIK

Anti-IL8 mAb 861 Vh   (Seq. ID No: 31)
QVQLVESGGGVVQPGRSLRLSCAASGFTFSNYGMHWVRQAPGKGLEWVAVIYFEGSNKYNADSV
KGRFTISRDNSKNTLYLQMNSLRAEDTAVYYCARSPYGDYLDYWGQGTLVTVSS

Anti-IL8 mAb 928 Vk   (Seq. ID No: 33)
EIVLTQSPGTLSLSPGERATLSCRASQSVSSSFLAWYQQKPGQAPRLLIYGASSRATGIPDRFS
GSGSGTDFILTISRLEPEDFAVYYCQQYDSSFTFGPGTKVDIK

Anti-IL8 mAb 928 Vh   (Seq. ID No: 35)
QVQLVESGGGVVQPGRSLRLSCAASGFTFSSYGMLWVRQAPGKGLEWVADISYDGSNKYYADSV
KGRFTISRDNSKNTLYLQMNSLRAEDTAVFYCARDRIAVADYWGQGTLVTVSS

Anti-IL8 mAb 1064 Vk (Seq. ID No: 37)
EIVLTQSPGTLSLSPGERATLSCRASQSVSSSYLAWYQQRPGQAPRLLIYGAYRRATGIPDRFS
GSGSGTDFTLTISRLEPEDFAVYYCQQDGSSFTFGPGTKVDIK

Anti-IL8 mAb 1064 Vh (Seq. ID No: 39)
QVQLVESGGGVVQPGRSLRLSCAASGFTFSTYGMHWVRQAPGKGLEWVALISYDGSNKYYADSV
KGRFTISRDNSKNTLYLQMNSLRAEDTAVYYCARDHIAVADYWGQGTLVTVSS

*FIG. 1B*

Anti-IL8 mAb 1080 Vk (Seq. ID No: 41)
DIVMTQSPDSLAVSLGERATINCRSSQSVLYSSNNKNYLAWYQQKSGQPPKLLIYLASIRESGV
PDRFSGSGSGTDFALTISNLQAEDVAVYYCQQYYSTPLTFGGGTKVEIK

Anti-IL8 mAb 1080 Vh (Seq. ID No: 43)
QVQLQQWGAGLLKPSESLSLTCAVYGGSFFSGYYWSWIRQPPGKGLEWIGEITHSGNTNYNPSL
KSRVSISVDTSTNQFSLKLSSVTAADTAVYYCGRGGAEVGFDYWGQGTLVTVSS

Anti-IL8 mAb 1093 Vk (Seq. ID No: 45)
DIVMTQSPDSLVVSLGERATINCKSSQSVLYSSNNKNYLAWYQQKPGQPPKLLIYWASTRESGV
PDRFSGSGSGTDFTLTISSLQAEDVAVYYCQQYYDTPFTFGGGTKVEIK

Anti-IL8 mAb 1093 Vh (Seq. ID No: 47)
QVQLQQWGAGLLKPSETLSLTCAVFGGSFSGYYWTWIRQPPGKGLEWIGEIIHHGSTNYSPSLK
SRVTISADTSKSQFSLRLSSVTAADTAVYYCARGGAAAGLDSWGQGTLVTVSS

FIG. 1C

Anti-IL8 mAb 33 Vk        (Seq. ID No: 2)
GACATCGTGATGACCCAGTCTCCAGACTCCCTGGCTGTGTCTCTGGGCGAGAGGGCCACCATCA
ACTGCATGTCCAGCCAGAGTCTTTTATACAGCTCCAACAATAAGAACTACTTAGCTTGGTACCA
GCAGAAACCAGGACAGCCTCCTAAGCTGCTCATTTACTGGGCATCTACCCGGGAATCCGGGGTC
CCTGACCGATTCAGTGGCAGCGGGTCTGGGACAGATTTCACTCTCACCATCAGCAGCCTGCAGG
CTGAAGATGTGGCAGTTTATTACTGTCAGCAATATTATGGTACTCCTCTCACTTTCGGCGGAGG
GACCAAGGTGGAGATCAAA

Anti-IL8 mAb 33 Vh        (Seq. ID No: 4)
CAGGTGCAGCTACAACAGTGGGGCGCAGGACTATTGAAGCCTTCGGAGACCCTGTCCCT
CACCTGCGCTGTCTATGGTGGGTTCTTCAGTGGTTACTACTGGAGCTGGATCCGCCAGCCCCCA
GGGAAGGGGCTGGAGTGGATTGGGGAAATCAATCATAGTGGAAGCACCAACTACAACCCGTCCC
TCAAGAGTCGAGTCACCATATCAGTAGACACGTCCAAGAACCAGTTCTCCCTGAAGTTGATCTC
TGTGACCGCCGCGGACACGGCTGTGTATTACTGTGCGAGAGGATCAGCAGCCGAGGCTTTTGAT
ATCTGGGGCCAAGGGACAATGGTCACCGTCTCTTCA

Anti-IL8 mAb 142 Vk        (Seq. ID No: 6)
GACATCCAGATGACCCAGTCTCCATCCTCCCTGTCTGCATCTGTAGGAGACAGAGTCACCATCA
CTTGCCGGGCGAGTCAGGGCATTAGCAATTCTTTAGCCTGGTATCAGCAGAAACCAGGGAAAGT
TCCTAACCTCCTGATCTATGCTGCGTCCACTTTGCAATCTGGGGTCCCATCTCGGTTTAGTGGC
AGTGGATCTGGGACAGATTTCACTCTCACCATCAGCAGCCTGCAGCCTGAAGATGTTGCAACTT
ATTACTGTCAAAAATATAACAGTGTCCCGCTCACCTTCGGCGGAGGGACCAAGGTGGAGATCAA
A

Anti-IL8 mAb 142 Vh        (Seq. ID No: 8)
CAGGTGCAGCTGGTGCAGTCTGGGGCTGAGGTGAAGAAGCCTGGGGCCTCAGTGAAGGTCTCCT
GCAAGGCTTCTGGATACACCTTCACCGGCTACTATATGCACTGGGTGCGACAGGCCCCTGGACA
AGGGCTTGAGTGGATGGGATGGATCAACTCTAACAGTGGTGGCACAAACTATTCACAGAAGTTT
CAGGGCAGGGTCACCATGACCAGGGACACGTCCATCAGCACAGTCTACATGGAGCTGAGCAGGC
TGAGATCTGACGACACGGCCGTGTATTACTGTGCGAGTGGATACAGCTATGGTTACCGCTACTA
CTACTACGGTATGGACGTCTGGGGCCAAGGGACCACGGTCACCGTCTCCTCA

Anti-IL8 mAb 203 Vk        (Seq. ID No: 10)
GACATCCAGATGACCCAGTCTCCATCCTCCCTGTCTGCATCTGTAGGAGACAGAGTCACCATCA
CTTGCCGGGCGAGTCAGGGCATTAGCAATTCTTTAGCCTGGTATCAGCAGAAACCAGGGAAAGT
TCCTAAGCTCCTGATCTATGCTGCATCCACTTTGCAATCAGGGGTCCCATCTCGGTTTAGTGGC
AGTGGATCTGGGACAGATTTCACTCTCACCATCAGCAGCCTGCAGCCGGAAGATGTTGCAACTT
ATTACTGTCAAAAGTATAACAGTGTCCCGCTCACTTTCGGCGGAGGGACCAAGGTGGAGATCAA
T

FIG. 2A

Anti-IL8 mAb 203 Vh        (Seq. ID No: 12)
CAGGTGCAGCTGGTGCAGTCTGGGGCTGAGGTGAAGAAGCCTGGGGCCTCAGTGAAGGTCTCCT
GCAAGGCTTCTGGATATACCTTCACCGGCTACTATATACATGGGTGCGACAGGCCCCTGGACA
AGGGCTTGAGTGGATGGGATGGATCAACTCTAACAGTGGTGGCACAAACTTTGCACAGAAGTTT
CAGGGCAGGGTCACCATGACCAGGGACACGTCCATCAGCACAGCCTACATGGAGCTGAGCAGGC
TGAGACCTGACGACACGGCCGTGTATTACTGTGCGAGTGGATATAGATATGGCTACCGCTACTA
CTACTACGGTATGGACGTCTGGGGCCAAGGGACCACGGTCACCGTCTCCTCA

Anti-IL8 mAb 215 Vk        (Seq. ID No: 14)
GAAATTGTGTTGACGCAGTCTCCAGGCACCCTGTCTTTGTCTCCAGGGGAAAGAGCCACCCTCT
CCTGCAGGGCCAGTCAGAATGTTAGCAGCAGCTACTTAGCCTGGTACCAGCAGAAACCTGGCCA
GGCTCCCAGGCTCCTCATCTATGGTGCATCCAGCAGGGCCACTGGCATCCCAGACAGGTTCAGT
GGCAGTGGGTCTGGGACAGACTTCACTCTCACCATCAGCAGACTGGAGCCTGAAGATTTTGCAG
TGTATTACTGTCAGCAGTATGGTAGCTCATTCACTTTCGGCCCTGGGACCAAAGTGGATATCAA
A

Anti-IL8 mAb 215 Vh        (Seq. ID No: 16)
CAGGTGCAGCTGGTGGAGTCTGGGGGAGGCGTGGTCCAGCCTGGGAGGTCCCTGAGACTCTCCT
GTGCAGCCTCTGGATTCACCTTCAGTAGCTATGGCATGCACTGGGTCCGCCAGGCTCCAGGCAA
GGGGCTGGAGTGGGTGGCAGATATATCATATGATGGAAGTAATAAATACTATGCAGACTCCGTG
AAGGGCCGATTCACCATCTCCAGAGACAATTCCAAGAACACGCTGTATCTGCAAATGAACAGCC
TGAGAGCTGAGGACACGGCTGTGTATTACTGTGCGAGAGACCGTATAGCAGTGTTGGACTACTG
GGGCCAGGGAACCCTGGTCACCGTCTCCTCA

Anti-IL8 mAb 469 Vk        (Seq. ID No: 18)
GACATTCAGATGACCCAGTCTCCATCCTCCCTGTCTGCATCTGTGGGAGACAGAGTCACCATCG
CTTGCCGGGCAAGTCAGGGCATTAGAAATGATTTAGGCTGGTATCAGCAGAAGCCAGGGAAAGC
CCCTAAACGCCTGATCTATGCTGCATCCAGTTTACAAAGTGGGGTCCCATCAAGGTTCGGCGGC
AGTGGATCTGGGACAGAATTCACTCTCACAATCAGCAGCCTGCAGCCTGAAGATTTTGCAACTT
ATTACTGTCTACAGCATAATAGTTACCCTCGGACGTTCGGCCAAGGAACCAAGGTGGAAATCAA
A

Anti-IL8 mAb 469 Vh        (Seq. ID No: 20)
GAAGTGCAGCTGTTGGAGTCGGGGGGAGGCTTGGTACAGCCTGGGGGGTCCCTGAGACTCTCCT
GTGCAGCCTCTGGATTCACCTTTAGCAGCTATGTCATGAGCTGGGTCCGCCAGGCTCCAGGGAA
GGGGCTGGAGTGGGTCTCAGCTATTAATAATAGTGGTGGTAGCACAGACTACGCAGACTCCGTG
AAGGGCCGGTTCACCATCTCCAGAGACAATTCCAAGAACACGCTGTATCTGCAAATGAACAGCC
TGAGAGCCGAGGACACGGCCGTATATTACTGTGCGAAAGAGGGACGATTTTGGAGTGGTCCCT
CTACGGTTTGGACGTCTGGGGCCAAGGGACCACGGTCACCGTCTCCTCAG

*FIG. 2B*

Anti-IL8 mAb 809 Vk      (Seq. ID No: 22)
GAAATTGTGTTGACGCAGTCTCCAGGCACCCTGTCTTTGTCTCCAGGGGAAAGAGCCACCCTCT
CCTGCAGGGCCAGTCAGAGTGTTAGCAGCAGCTACTTAGCCTGGTACCAGCAGAAACCTGGCCA
GGCTCCCAGGCTCCTCATCTATGGTGCATCCAGCAGGGCCACTGGCATCCCAGACAGGTTCAGT
GGCAGTGGGTCTGGGACAGACTTCACTCTCACCATCAGCAGACTGGAGCCTGAAGATTTTGCAG
TGTATTACTGTCAGCAGTATGGTAGCTCATTCACTTTCGGCCCTGGGACCAAAGTGGATATCAA
A

Anti-IL8 mAb 809 Vh      (Seq. ID No: 24)
TGTCCAGTGTCAGGTGCAGCTGGTGGAGTCTGGGGGAGGCGTGGTCCAGCCTGGGAGGTCCCTG
AGACTCTCCTGTGCAGCCTCTGGATTCACCTTCAGTAGCTATGGCATGCTCTGGGTCCGCCAGG
CTCCAGGCAAGGGGCTGGAGTGGGTGGCAGATATATCATATGATGGAAGTAATAAATACTATGC
AGACTCCGTGAAGGGCCGATTCACCATCTCCAGAGACAATTCCAAGAACACGCTGTTTCTGCAA
ATGAACAGCCTGAGAGCTGAGGACACGGCTGTGTATTACTGTGCGAGAGACCGTATAGCAGTGG
CTGACTACTGGGGCCAGGGAACCCTGGTCACCGTCTCCTCAGCCTCCACCAAGGGCCCATCGGT
CTTCCCCCTGGCGCCCTGCTCTAGAAGCACCTCCGAGAGCACAGCGGCCCTTGGCTGCCTGGTC
AAGGACTACTTCCCCGAACCGGTGACGGTGTC

Anti-IL8 mAb 837 Vk      (Seq. ID No: 26)
GACATCGTGCTGACCCAGTCTCCAGACTCCCTGGTTGTGTCTCTGGGCGAGAGGGCCACCATCA
ACTGCAAGTCCAGCCAGAGTGTTTTGTTCAGCTCCAACAATAGGAAATATTTAGCTTGGTACCA
GCAGAAAACAGGACAGCCTCCTAAGTTGCTCATTTACTGGGCATCTACCCGGGAATCCGGGGTC
CCTGACCGATTCAGTGGCAGCGGGTCTGGGACAGATTTCACTCTCACCATCAGCAGCCTGCAGG
CTGAAGATGTGGCAGTTTATTACTGTCAGCAATATTATAGTACTCCGTTCACTTTCGGCGGAGG
GACCAAGGTGGAGATCAAA

Anti-IL8 mAb 837 Vh      (Seq. ID No: 28)
CAGGTGCAACTACAGCAGTGGGGCGCAGGACTGTTGAAGCCTTCGGAAACCCTGTCCCTCACCT
GCGCTGTCTTTGGTGGGACCTTCAGTGGTTACTACTGGACCTGGATCCGCCAGCCCCCAGGGAA
GGGACTGGAGTGGATTGGGGAAGTCATCCATCATGGAAGCACCAACTACAGCCCGTCCCTCAAG
AGTCGAGTCACCATATCAGCAGACACGTCCAAGAGCCAGTTCTCCCTGAGGCTGAGCTCTGTGA
CCGCCGCGGACACGGCTGTGTATTACTGTGCGAGACGGGGAGCAGCAGCTGCTCTTGACTCCTG
GGGCCAGGGAACCCTGGTCATCGTCTCCTCA

Anti-IL8 mAb 861 Vk      (Seq. ID No: 30)
GAAATTGTGTTGACGCAGTCTCCAGGCACCCTGTCTTTGTCTCCAGGGGAAAGAGCCACCCTCT
CCTGCAGGGCCAGTCAGACCATTGACTACAACTATTTGCATTGGTACCAGCAGAAACCTGGCCA
GGCTCCCAGGCTCCTCATATATGGTACATTCATCAGGGCCACTGTCATCCCAGACAGGTTCAGT
GGCAGTGGGTCTGGGACAGACTTCACTCTCACCATCAGCAGACTGGAGCCTGAAGATATTGCAG
TGTATTACTGTCAGCAGTTTGGTAGGTCACCGCTCACTTTCGGCGGAGGGACCAAGGTGGAGAT
CAAA

FIG. 2C

Anti-IL8 mAb 861 Vh      (Seq. ID No: 32)
CAGGTGCAGCTGGTGGAGTCTGGGGGAGGCGTGGTCCAGCCTGGGAGGTCCCTGAGACTCTCCT
GTGCAGCGTCTGGATTCACCTTCAGTAACTATGGCATGCACTGGGTCCGCCAGGCTCCAGGCAA
GGGGCTGGAGTGGGTGGCGGTTATTTATTTTGAAGGAAGTAACAAATAC
AATGCAGACTCCGTGAAGGGCCGATTCACCATCTCCAGAGACAATTCCAAGAACACGCTGTATC
TGCAAATGAACAGCCTGAGAGCCGAGGACACGGCTCTGTATTACTGTGCGAGATCCCCCTACGG
TGACTACCTTGACTACTGGGGCCAGGGAACCCTGGTCACCGTCTCCTCA

Anti-IL8 mAb 928 Vk      (Seq. ID No: 34)
GAAATTGTGTTGACGCAGTCTCCAGGCACCCTGTCTTTGTCTCCAGGGGAAAGAGCCACCCTCT
CCTGCAGGGCCAGTCAGAGTGTTAGCAGTAGTTTCTTAGCCTGGTACCAGCAGAAACCTGGCCA
GGCTCCCAGGCTCCTCATCTATGGTGCATCCAGCAGGGCCACTGGCATCCCAGACAGGTTCAGT
GGCAGTGGGTCTGGGACAGACTTCATTCTCACCATCAGCAGACTGGAGCCTGAAGATTTTGCAG
TGTATTACTGTCAGCAGTATGATAGCTCATTCACTTTCGGCCCTGGGACCAAAGTGGATATCAA
A

Anti-IL8 mAb 928 Vh      (Seq. ID No: 36)
CAGGTGCAGCTGGTGGAGTCTGGGGGCGGCGTGGTCCAGCCTGGGAGGTCCCTGAGACTCTCCT
GTGCAGCCTCTGGATTCACCTTCAGTAGCTATGGCATGCTCTGGGTCCGCCAGGCTCCAGGCAA
GGGGCTGGAGTGGGTGGCAGATATATCATATGATGGAAGTAATAAATACTATGCAGACTCCGTG
AAGGGCCGATTCACCATCTCCAGAGACAATTCCAAGAACACGCTGTATCTGCAAATGAACAGCC
TGAGAGCTGAGGACACGGCTGTGTTTTATTGTGCGAGAGACCGTATAGCAGTGGCTGACTACTG
GGGCCAGGGAACCCTGGTCACCGTCTCCTCA

Anti-IL8 mAb 1064 Vk (Seq. ID No: 38)
GAAATTGTGTTGACGCAGTCTCCAGGCACCCTGTCTTTGTCTCCAGGGGAAAGAGCCACCCTCT
CCTGCAGGGCCAGTCAGAGTGTTAGCAGCAGCTACTTAGCCTGGTACCAGCAGAGACCTGGCCA
GGCTCCCAGGCTCCTCATCTATGGTGCATACAGAAGGGCCACTGGCATCCCAGACAGGTTCAGT
GGCAGTGGGTCTGGGACAGACTTCACTCTCACCATCAGCAGACTGGAGCCTGAAGATTTTGCAG
TGTATTACTGTCAGCAGGATGGCAGCTCATTCACTTTCGGCCCTGGGACCAAAGTGGATATCAA
A

Anti-IL8 mAb 1064 Vh (Seq. ID No: 40)
CAGGTGCAGCTGGTGGAGTCTGGGGGAGGCGTGGTCCAGCCTGGGAGGTCCCTGAGACTCTCCT
GTGCAGCCTCTGGATTCACCTTCAGTACCTATGGCATGCACTGGGTCCGCCAGGCTCCAGGCAA
GGGGCTGGAGTGGGTGGCACTTATATCATATGATGGAAGTAATAAATACTATGCAGACTCCGTG
AAGGGCCGATTCACCATCTCCAGAGACAATTCCAAGAACACGCTGTATCTGCAAATGAACAGCC
TGAGAGCTGAGGACACGGCTGTGTATTACTGTGCGAGAGATCATATAGCAGTGGCTGACTACTG
GGGCCAGGGAACCCTGGTCACCGTCTCCTCA

FIG. 2D

Anti-IL8 mAb 1080 Vk (Seq. ID No: 42)
GACATCGTGATGACCCAGTCTCCAGACTCCCTGGCTGTGTCTCTGGGCGAGAGGGCCACCATCA
ACTGCAGGTCCAGCCAGAGTGTTTTATACAGTTCCAACAATAAGAACTACTTAGCTTGGTACCA
GCAGAAATCAGGACAGCCTCCTAAACTACTCATTTACTTGGCATCTATTCGGGAATCCGGGGTC
CCTGACCGATTCAGTGGCAGCGGGTCTGGGACAGATTTCGCTCTCACCATCAGCAACCTGCAGG
CTGAAGATGTGGCAGTTTATTACTGTCAGCAATATTATAGTACTCCGCTCACTTTCGGCGGTGG
GACCAAGGTGGAGATCAAA

Anti-IL8 mAb 1080 Vh (Seq. ID No: 44)
CAGGTGCAACTACAGCAGTGGGGCGCAGGACTGTTGAAGCCTTCGGAGTCCCTGTCCCTCACCT
GCGCTGTCTATGGTGGGTCCTTCTTCAGTGGTTACTACTGGAGTTGGATCCGCCAGCCCCCAGG
GAAGGGGCTGGAGTGGATTGGGGAAATCACTCATAGTGGAAACACCAACTACAACCCGTCCCTC
AAGAGTCGAGTCAGCATATCAGTTGACACGTCCACGAACCAGTTCTCCCTGAAGTTGAGCTCTG
TGACCGCCGCGGACACGGCTGTCTATTACTGTGGGAGAGGGGGAGCAGAAGTTGGTTTTGACTA
CTGGGGCCAGGGAACCCTGGTCACCGTCTCCTCA

Anti-IL8 mAb 1093 Vk (Seq. ID No: 46)
GACATCGTGATGACCCAGTCTCCAGACTCCCTGGTTGTGTCTCTGGGCGAGAGGGCCACCATCA
ACTGCAAGTCCAGCCAGAGTGTTTTGTACAGCTCCAACAATAAGAACTACTTAGCTTGGTACCA
GCAGAAACCAGGACAGCCTCCTAAGTTGCTCATTTACTGGGCATCTACCCGGGAATCCGGGGTC
CCTGACCGATTCAGTGGCAGCGGGTCTGGGACAGATTTCACTCTCACCATCAGCAGCCTGCAGG
CTGAAGATGTGGCAGTTTATTACTGTCAGCAATATTATGATACTCCGTTCACTTTCGGCGCAGG
GACCAAGGTGGAGATCAAA

Anti-IL8 mAb 1093 Vh (Seq. ID No: 48)
CAGGTGCAGCTACAGCAGTGGGGCGCAGGACTGTTGAAGCCTTCGGAAACCCTGTCCCTCACCT
GCGCTGTCTTTGGTGGGTCCTTCAGTGGTTACTACTGGACCTGGATCCGCCAGCCCCCAGGGAA
GGGACTGGAGTGGATTGGGGAAATCATCCATCATGGAAGCACCAACTACAGCCCGTCCCTCAAG
AGTCGAGTCACCATATCAGCAGACACGTCCAAGAGCCAGTTCTCCCTGAGGCTGAGCTCTGTGA
CCGCCGCGGACACGGCTGTGTATTACTGTGCGAGAGGGGGAGCAGCAGCTGGTCTTGACTCCTG
GGGCCAGGGAACCCTGGTCACCGTCTCCTCA

| Well | Single Cell | Chain ID | V Heavy/D/J | FR1 | CDR1 | FR2 | SEQ ID NO |
|---|---|---|---|---|---|---|---|
| | | Germline | | QVQLVQSGAEVKKPGASVKVSCKAS | GYTFTGYYMH | WVRQAPGQGLEWMG | 50 |
| 20G9 | 142 | 9140.3MA | 9140.3MA | ---------------------- | ---------- | -------------- | 7 |
| 1D11 | 203 | 9388.2MA | 9140.3MA | ---------------------- | -----I---- | -------------- | 11 |
| | | Germline | | EVQLLESGGGLVQPGGSLRLSCAAS | GFTFSSYAMS | WVRQAPGKGLEWVS | 51 |
| 54C6 | 469 | 10717.1MA | VH3-23/D3-3/JH6B | ---------------------- | -----V---- | -------------- | 19 |
| | | Germline | | QVQLVESGGGVVQPGRSLRLSCAAS | GFTFSSYGMH | WVRQAPGKGLEWVA | 52 |
| 43C3 | 215 | 3911.1MA | | ---------------------- | -----L---- | -------------- | 15 |
| 6G11 | 809 | 17290.5MA | VH3-30/D6-19/JH4B | ---------------------- | -----L---- | -------------- | 23 |
| 46G8 | 928 | 17889.6MA | | ---------------------- | ---------- | -------------- | 35 |
| 7E10 | 1064 | 22444.3MA | | ---------------------- | ----T----- | -------------- | 39 |
| | | Germline | | QVQLVESGGGVVQPGRSLRLSCAAS | GFTFSSYGMH | WVRQAPGKGLEWVA | 53 |
| 50B1 | 831 | 19690.2MA | VH3-33-D4-23/JH4B | QVQLQQWGAGLLKPSETLSLTTCAVY | -----N---- | WIRQPPGKGLEWIG | 31 |
| | | Germline | | QVQLQQWGAGLLKPSETLSLTTCAVY | GGSFSGYYWS | WIRQPPGKGLEWIG | 54 |
| 45E12 | 1093 | 23014.1MA | VH4-34/D1-26/JH5A | ----------------------F | -----T---- | -------------- | 47 |
| | | Germline | | QVQLQQWGAGLLKPSETLSLTTCAVY | GGSFSGYYWS | WIRQPPGKGLEWIG | 55 |
| DIR PLAQ | 33 | 8354.2MA | VH4-34/D1-26/JH5A | ---------------------- | --F------- | -------------- | 3 |
| | | Germline | | QVQLQQWGAGLLKPSETLSLTTCAVY | GGSFSGYYWS | WIRQPPGKGLEWIG | 56 |
| 36C6 | 837 | 17073.3MA | | ----------------------F | ----T----- | -------------- | 27 |
| 42E5 | 1080 | 23236.2MA | VH4-34/D6-13/JH4B | -----------------S---- | --F------- | -------------- | 43 |

| SEQ ID NO | CDR2 | FR3 | CDR3 | FR4 |
|---|---|---|---|---|
| 50 | WINPNSGGTNYAQKFQG | RVTMTRDTSISTAYMELSRLRSDDTAVYYCAR | XXXXXXXXXXXXXXX | WGQGTTVTVSS |
| 7 | ----S------------ | --------------V----------------S | GYSYGYRYYYYGMDV | ----------- |
| 11 | ----S--F--------- | --------------------------P----S | ---R----------- | ----------- |
| 51 | AISGSGGSTYYADSVKG | RFTISRDNSKNTLYLQMNSLRAEDTAVYYCAK | XXXXXXXXXXXXXXX | WGQGTTVTVSS |
| 19 | ----NN----D------ | -------------------------------- | EGRFLEWSLYGLDV | ----------- |
| 52 | VISYDGSNKYADSVKG | RFTISRDNSKNTLYLQMNSLRAEDTAVYYCAR | XXXXXXX | WGQGTMVTVSS |
| 15 | D--------------- | -------------------------------- | DRIAVLDY | ----------- |
| 23 | D--------------- | -------------F------------------ | -------- | ----------- |
| 35 | D--------------- | -------------------------------- | -------- | ----------- |
| 39 | L--------------- | -------------------------------- | -H------ | ----------- |
| 53 | VIWYDGSNKYYADSVKG | RFTISRDNSKNTLYLQMNSLRAEDTAVYYCAR | XXXXXXXX | WGQGTLVTVSS |
| 31 | --YFE----N------ | -----------------F-------------- | SPYGDYLDY | ----------- |
| 54 | EINHSGSTNYNPSLKS | RVTISVDTSKNQFSLKLSSVTAADTAVYYCAR | XXXXXXXX | WGQGTLVTVSS |
| 47 | ----I-H----S---- | ----A-----S------R-------------- | GGAAAGLDS | ----------- |
| 55 | EINHSGSTNYNPSLKS | RVTISVDTSKNQFSLKLSSVTAADTAVYYCAR | XXXXXXXX | WGQGTMVTVSS |
| 3 | -------------I-- | -------------------------------- | GSAAEAFDI | ----------- |
| 56 | GEINHSGSTNYNPSLK | RVTISVDTSKNQFSLKLSSVTAADTAVYYCAR | XXXXXXXX | WGQGTMVTVSS |
| 27 | -VI--H-----S---- | ----A-----S-T------R------------ | GGAAALDS | ----------- |
| 43 | ----T--N-------- | -------------------------------G | ---EVGF-Y | --------I-- |

| Well | Single Cell | Chain ID | V Kappa/J | FR1 | CDR1 | FR2 | SEQ ID NO |
|---|---|---|---|---|---|---|---|
|  |  | Germline |  | DIQMTQSPSSLSASVGDRVTITC | RASQGISNYLA | WYQQKPGKVPKLLIY | 57 |
| 20G9 | 142 | 9057.1MA | A20/JK4 | ---------------------- | -------S--- | -------N------- | 5 |
| 1D11 | 203 | 9359.2MA |  | ---------------------- | -------S--- | --------------- | 9 |
|  |  | Germline |  | EIVLTQSPGTLSLSPGERATLSC | RASQSVSSSYLA | WYQQKPGQAPRLLIY | 58 |
| 43C3 | 215 | 9297.1MA | A27/JK3 | ---------------------- | -----N------ | --------------- | 13 |
| 6G11 | 809 | 17246.3MA |  | ---------------------- | ------------ | --------------- | 21 |
| 46G8 | 928 | 18144.2MA |  | ---------------------- | -----F------ | --------------- | 33 |
| 7E10 | 1064 | 22597.5MA |  | ---------------------- | ------------ | ------R-------- | 37 |
|  |  | Germline |  | EIVLTQSPGTLSLSPGERATLSC | RASQSVSSSYLA | WYQQKPGQAPRLLIY | 59 |
| 50B1 | 861 | 19837.2MA | A27/JK4 | ---------------------- | ----TIDYN--H | --------------- | 29 |
|  |  | Germline |  | DIQMTQSPSSLSASVGDRVTITC | RASQGIRNDLG | WYQQKPGPPKLLIY | 60 |
| 54C1 | 469 | 10626.1MA | A30/JK1 | --------------------A- | ----------- | --------------- | 17 |
|  |  | Germline |  | DIVMTQSPDSLAVSLGERATINC | KSSQSVLYSSNNKNYLA | WYQQKPGQPPKLLIY | 61 |
| DIR PLAQ | 33 | 8318.2MA | B3/JK4 | ---------------------- | M-------L------- | --------------- | 1 |
| 36C6 | 837 | 17037.7MA |  | ----L----------------- | --------F---RK-- | -------T------- | 25 |
| 42F5 | 1080 | 23183.1MA |  | ----V----------------- | ----------------- | --------------- | 41 |
| 45E12 | 1093 | 23233.3MA |  | ----V----------------- | R---------------- | -------S------- | 45 |

| SEQ ID NO | CDR2 | FR3 | CDR3 | J |
|---|---|---|---|---|
| 57 | AASTLQS | GVPSRFSGSGSGTDFTLTISSLQPEDVATYYC | QKYNSAPLT | FGGGTKVEIK |
| 5 | ------- | -------------------------------- | QKYNSVPLT | ---------- |
| 9 | ------- | -------------------------------- | --------- | -------N- |
| 58 | GASSRAT | GIPDRFSGSGSGTDFTLTISRLEPEDFAVYYC | QQYGSSPFT | FGPGTKVDIK |
| 13 | ------- | -------------------------------- | QQYGSSFT  | ---------- |
| 21 | ------- | -------I------------------------ | --------- | ---------- |
| 33 | --YR--- | -------------------------------- | ---D----- | ---------- |
| 37 | ------- | -------------------------------- | ---D----- | ---------- |
| 59 | GASSRAT | GIPDRFSGSGSGTDFTLTISRLEPEDFAVYYC | QQYGSSPLT | FGGGTKVEIK |
| 29 | -TFI--- | V-----------------------I------- | QQFGRSPLT | ---------- |
| 60 | AASSLQS | GVPSRFSGSGSGTEFTLTISSLQPEDFATYYC | LQHNSYPWT | FGGGTKVEIK |
| 17 | ------- | -------G------------------------ | LQHNSYPRT | ---------- |
| 61 | WASTRES | GVPDRFSGSGSGTDFTLTISSLQAEDVAVYYC | QQYYSTPLT | FGGGTKVEIK |
| 1 | ------- | -------------------------------- | QQYYGTPLT | ---------- |
| 25 | ------- | -------------------------------- | -----F--- | ---------- |
| 41 | --L-I-- | ------------A-----N------------- | --------- | ---------- |
| 45 | ------- | -------------------------------- | ---D-F--- | ---------- |

*FIG. 4B Continued*

|  |  | SEQ ID NO: |
|---|---|---|
| IL-8 | YSKPFHPKFIKE | 49 |
|  | EGKPF-PTFLLRS | 65 |
|  | VWSKMM-PQFLTP | 66 |
|  | HAKPL-PHWMGHP | 67 |
|  | NGNVKPV-PKFLH | 68 |
|  | IGSPKPY-PHFLG | 69 |
|  | SQLNKPR-PIFLY | 70 |
|  | NPLQSKPI-PIFL | 71 |
|  | VPQKKF-PIFLNL | 72 |
|  | VPSKTM-PHFLLT | 73 |
|  | YEKPI-PHYLSQR | 74 |
| Consensus | KPX-PXF | 63 |

FIG. 5

| Peptide fragment: | | SEQ ID NO: |
|---|---|---|
| AVLPRSAKELRC | | 75 |
| LPRSAKELRCQC | | 76 |
| RSAKELRCQCIK | | 77 |
| AKELRCQCIKTY | | 78 |
| ELRCQCIKTYSK | Epitope for ABXha-IL-8 | 79 |
| RCQCIKTYSKPF | | 80 |
| QCIKTYSKPFHP | | 81 |
| IKTYSKPFHPKF | | 82 |
| YSKPFHPKFIKE | | 83 |
| KPFHPKFIKELR | *Epitope for ABX-IL-8* | 84 |
| FHPKFIKELRVI | | 85 |
| PKFIKELRVIES | | 86 |
| FIKELRVIESGP | | 87 |
| KELRVIESGPHC | | 88 |
| LRVIESGPHCAN | | 89 |
| IESGPHCANTEI | | 90 |
| SGPHCANTEIIV | | 91 |
| PHCANTEIIVKL | | 92 |
| CANTEIIVKLSD | | 93 |
| NTEIIVKLSDGR | | 94 |
| EIIVKLSDGREL | | 95 |
| IVKLSDGRELCL | | 96 |
| LSDGRELCLDPK | | 97 |
| DGRELCLDPKEN | | 98 |
| RELCLDPKENWV | | 99 |
| LCLDPKENWVQR | | 100 |
| LDPKENWVQRVV | | 101 |
| PKENWVQRVVEK | | 102 |
| ENWVQRVVEKFL | | 103 |
| VQRVVEKFLKRA | | 104 |
| VVEKFLKRAENS | | 105 |

FIG. 8

```
Panning against Ab 809
IL8           SAKELRCQCIKTYSKPFHPKFIKELRVIESGPHCANTEIIVKLSDGRELCLDPKENWVQRVVEK  (SEQ ID NO: 106)
Translation of 809-1        GYKSLPHSLPMI                                        (SEQ ID NO: 107)
Translation of 809-2        TPYKAFNHSLPL                                        (SEQ ID NO: 108)
Translation of 809-3           YKQPNHSMPMLS                                     (SEQ ID NO: 109)
         Consensus           YKAPNHS_PMI                                        (SEQ ID NO: 110)
```

FIG. 9

```
Panning against Ab 928
IL-8      SAKELRCQCIKTYSKPFHPKFIKELRVIESGPHCANTEIIVKLSDGRELCLDPKENWV  (SEQ ID NO: 111)
Translation of 928-1        SKHWHPLLYSQF                                  (SEQ ID NO: 112)
Translation of 928-2        YAHSLNSPPRLS                                  (SEQ ID NO: 113)
       Consensus            HSK  FHPKL                                    (SEQ ID NO: 114)
```

HIGH AFFINITY FULLY HUMAN MONOCLONAL ANTIBODIES TO INTERLEUKIN-8

REFERENCE TO RELATED APPLICATIONS

The present application is the U.S. national phase entry under 35 U.S.C. §371 of PCT/US2006/014440, filed Apr. 18, 2006, which claims priority to U. S. Provisional Application No: 60/673,452, filed Apr. 20, 2005, the entireties of both of which are incorporated herein by reference.

The present application is being filed along with a Sequence Listing in electronic format. The Sequence Listing is provided as a file entitled ABGENIX121NP.TXT, created Oct. 18, 2007, which is 58 Kb in size. The information in the electronic format of the Sequence Listing is incorporated herein by reference in its entirety.

FIELD

The present invention relates generally to novel antibodies to interleukin-8 (IL-8). More specifically, the invention relates to fully human monoclonal antibodies with high affinity towards interleukin-8 and epitopes that are bound by such antibodies.

BACKGROUND

Interleukin-8 (IL-8) is a member of the C—X—C chemokine family and acts as the primary chemoattractant for neutrophils. IL-8 is implicated in many inflammatory diseases. Although recruitment and activation of neutrophils are important in the normal inflammation response, excessive or continuous neutrophil recruitment often leads to acute inflammation (Matsumoto et al., *J. Leukoc. Biol.*, 62 (5): 581-7 (1997)). In addition, IL-8 is a potent angiogenic factor for endothelial cells and has been implicated in tumor angiogenesis.

Anti-IL-8 antibodies have been developed and used for treating bacterial pneumonia (U.S. Pat. No. 5,686,070), asthma (U.S. Pat. No. 5,874,080), and ulcerative colitis (U.S. Pat. No. 5,707,622). In addition, anti-IL-8 antibodies have been proposed for the treatment of Chronic Obstructive Pulmonary Disease (COPD), which is one of the most common chronic conditions and the fourth leading cause of death in the United States. COPD includes several related disorders that restrict the patient's ability to exhale. Accordingly, patients frequently experience dyspnea, or shortness of breath. Dyspnea typically causes patient discomfort, limits the patient's ability to engage in physical activity, and can induce further adverse health effects due to a diminished supply of oxygen. The two most common disorders associated with COPD are chronic bronchitis and emphysema, though patients suffering from COPD may also have chronic asthma, bronchiectasis, immunoglobulin deficiency, and cystic fibrosis.

Recently, it has been suggested that IL-8 may be a novel target for the treatment of diseases involving acute inflammation, such as gastrointestinal diseases (Ajuebor et al., *Immunology*, 105 (2):137-43 (2002)). IL-8 may also be a target for the treatment of cancer and tumors, such as melanoma (Singh et al., *Histol. Histopathol*, 15 (3):843-9 (2000) and systemic inflammatory syndrome (SIRS) (Dinarello et al., *JAMA*, 269 (14):1829-35 (1993)).

Other diseases associated with IL-8 include inflammatory diseases (Matsumoto et al., *J. Leukoc. Biol.*, 62 (5):581-7 (1997)) such as ARDS, glomerlonephritis, alcoholic hepatitis, repurfusion injury, psoriasis (Jiang et al., *Int J Dermatol*, 40 (11):699-703 (2001)), rheumatoid arthritis (Kraan et al., *J Invest Dermatol*, 116 (2):319-29 (2001)), and inflammatory bowel disease (Imada et al., *Scand J Gastroenterol*, 36 (8): 854-64 (2001)), pulmonary disorders, such as idiopathic pulmonary fibrosis (Lynch et al., *Am Rev Respir Dis.*, 145 (6): 1433-9 (1992)), tumor progression (Xie et al., *Cytokine Growth Factor Rev.*, 12 (4):375-91 (2001)) and cancer and tumors generally, such as malignant melanoma, head and neck cancer, breast cancer, non-small cell lung cancer, ovarian cancer and brain cancer.

ABX-IL-8, a fully human monoclonal antibody generated with XenoMouse® technology, has been shown to block the activity of interleukin-8 (Press Release, Abgenix, Inc., Jan. 3, 2002). ABX-IL-8 has been shown to have potent anti-inflammation activity. ABX-IL-8 binds with high affinity to IL-8, blocks IL-8 binding to neutrophils, and inhibits neutrophil activation and migration (Yang et al., *J. Leukoc. Biol.*, 66 (3):401-410 (1999)). Additional descriptions of human antibodies to IL-8 and methods of making them can be found in U.S. Pat. No. 6,150,584 (Kucherlapati et al.) and U.S. Pat. No. 6,713,610 (Kucherlapati et al.), incorporated by reference in their entireties.

High affinity antibodies to IL-8 can be desirable. However, it has been proposed that under physiological conditions, there is a ceiling on antibody affinity maturation in vivo for any antigen and that this ceiling is around 100 pM. (See generally, Foote, J. & Eisen, H. N., *PNAS USA*, 92:1254-6 (1995); Batista, F. D. & Neuberger, M. S., *Immunity*, 8:751-9 (1998); and Watts, C. & Davidson, H. W., EMBO J., 7:1937-45 (1998)). Moreover, even optimized antibodies, such as those that have been affinity matured in vitro by phage, yeast, or ribosome display, appear to have affinities that are limited to more than 10 pM. (See, "Demonstration of an in vivo generated sub-picomolar affinity fully human monoclonal antibody to interleukin-8," Rathanaswami et al., Biochem. Biophys. Res. Commun. 334:1004-13 (2005), incorporated in its entirety by reference).

SUMMARY OF THE INVENTION

In one aspect the present invention relates to high-affinity antibodies to IL-8. The antibodies preferably have a $K_d$ for IL-8 of less than 10 pM, more preferably less than 1 pM, yet more preferably less than 100 fM and still more preferably less than 10 fM. The antibodies are preferably human monoclonal antibodies and may bind to a conformational epitope or a linear epitope. In preferred embodiments, the antibodies neutralize at least one biological activity of IL-8, such as the ability to bind the IL-8 receptor.

In some aspects, the present invention relates to an antibody or antigen-binding portion thereof that binds to a peptide, wherein the peptide is ELRCQCIKTYSK (SEQ ID NO: 79). In some aspects, the present invention relates to an antibody or antigen-binding portion thereof that binds to a peptide, wherein the peptide is ELRCQCIKTYSK (SEQ ID NO: 79). In some aspects, the present invention relates to an antibody or antigen-binding portion thereof that binds to a peptide, wherein the peptide is LRCQCIKTYSKPFHPKFIKE (SEQ ID NO: 62) or ELRCQCIKTYSK (SEQ ID NO: 79).

In some aspects, the present invention relates to a method for treating a disease comprising administering to a subject an effective amount of an anti-IL-8 antibody, wherein said anti-IL-8 antibody binds to a peptide having the contiguous sequence ELRCQCIKTYSK (SEQ ID NO: 79).

In some aspects, the present invention relates to a method for treating a disease comprising administering to a subject an effective amount of an anti-IL-8 antibody, wherein said anti- IL-8 antibody binds to a peptide, wherein said peptide is ELRCQCIKTYSK (SEQ ID NO: 79).

In some aspects, the present invention relates to a method for treating a disease comprising administering to a subject an effective amount of an anti-IL-8 antibody, wherein said anti-IL-8 antibody binds to IL-8 with a $K_d$ of less than about 10 pM.

In some aspects, the present invention relates to a therapeutic composition comprising an antibody that immunoreacts with an IL-8 epitope, wherein said IL-8 epitope is amino acids ELRCQCIKTYSK (SEQ ID NO: 79), wherein said antibody prevents inflammation, and wherein the antibody has a $K_d$ that is less than about 10 pM.

In some aspects, the present invention relates to a use of a human monoclonal antibody to IL-8 in the preparation of a medicament for the treatment of an IL-8 related disorder, wherein the IL-8 related disorder is selected from the group consisting of: IL-8 malignant melanoma, pulmonary disorders, an inflammatory condition; chronic obstructive pulmonary disease (COPD), idiopathic pulmonary fibrosis, psoriasis, rheumatoid arthritis, and inflammatory bowel disease, and wherein the human monoclonal antibody has a $K_d$ for IL-8 that is less than about 10 pM.

In some aspects, the present invention relates to a use of the antibody or antigen-binding portion thereof that is described herein, in the preparation of a medicament for the treatment of an IL-8 related disorder, wherein the IL-8 related disorder is selected from the group consisting of: IL-8 malignant melanoma, pulmonary disorders, an inflammatory condition; chronic obstructive pulmonary disease (COPD), idiopathic pulmonary fibrosis, psoriasis, rheumatoid arthritis, and inflammatory bowel disease.

In another aspect the invention relates to an antibody selected from the group consisting of antibody numbers, disclosed below, 33, 142, 203, 215, 469, 809, 837, 861, 928, 1064, 1080 and 1093. In particular embodiments an antibody is selected from the group consisting of antibody numbers 809, 837, 861, 928, and 1064.

In some embodiments the high-affinity anti-IL-8 antibody comprises a heavy chain variable region amino acid sequence comprising an amino acid sequence that is at least 90%, more preferably at least 95% identical to SEQ ID NO: 3 and a light chain variable region amino acid sequence comprising an amino acid sequence that is at least 90%, more preferably at least 95% identical to SEQ ID NO: 1. In other embodiments the antibodies comprise heavy and light chain variable regions comprising amino acid sequences that are at least 90%, more preferably at least 95% identical to SEQ ID NOs: 7 and 5, 11 and 9, 15 and 13, 19 and 17, 23 and 21, 27 and 25, 31 and 29, 35 and 33, 39 and 37, 43 and 41, and 47 and 45, respectively.

In some embodiments, the heavy chain variable region of a high-affinity antibody to IL-8 comprises an amino acid sequence selected from the group consisting of SEQ ID NO: 3, 7, 11, 15, 19, 23, 27, 31, 35, 39, 43, and 47. The light chain variable region preferably comprises an amino acid sequence selected from the group consisting of SEQ ID NO: 1, 5, 9, 13, 17, 21, 25, 29, 33, 37, 41, and 45.

In other embodiments the high-affinity anti-IL-8 antibodies comprise heavy and light chain variable regions that are encoded by nucleic acids comprising nucleotide sequences that are at least 90%, more preferably at least 95% identical to SEQ ID NOs: 4 and 2, 8 and 6, 12 and 10, 16 and 14, 20 and 18, 24 and 22, 28 and 26, 32 and 30, 36 and 34, 40 and 38, 44 and 42, and 48 and 46, respectively.

In particular embodiments, an antibody is provided that specifically binds to IL-8 comprising a heavy chain amino acid sequence that is at least 90% identical to SEQ ID NO: 35, more preferably at least 95% identical. The antibody preferably comprises a light chain that is at least 90% identical to SEQ ID NO: 33, more preferably at least 95% identical to SEQ ID NO: 33. In one embodiment, the antibody is preferably antibody number 928.

In another particular embodiment, a monoclonal antibody that specifically binds to IL-8 with high affinity comprises a heavy chain amino acid sequence comprising amino acid residues 1-66 of SEQ ID NO: 35 and a light chain amino acid sequence comprising SEQ ID NO: 33. The antibody preferably has an affinity better than 1 pM.

Antibodies are also provided that specifically bind to IL-8 with high-affinity, wherein the heavy chain amino acid sequence comprises a CDR1, a CDR2, and a CDR3 sequence, the CDR1 sequence being independently selected from the group consisting of amino acid residues 26-35 of SEQ ID NO: 7, 11, 19, 15, 23, 35, 39, 31, 47, 3, 27, and 43; the CDR2 sequence being independently selected from the group consisting of amino acid residues 50-66 of SEQ ID NO: 7, 11, 19, 15, 23, 35, and 39 and amino acid residues 50-65 of SEQ ID NO: 31, 47, 3, 27, or 43; and the CDR3 sequence being independently selected from the group consisting of amino acid residues 99-113 of SEQ ID NO: 7 and 11, amino acid residues 99-112 of SEQ ID NO: 19, amino acid residues 99-106 of SEQ ID NO: 15, 23, 35, and 39, and amino acid residues 98-106 of SEQ ID NO: 31, 47, 3, 27, or 43.

In other embodiments antibodies are provided that specifically bind IL-8 with high-affinity, wherein the light chain amino acid sequence comprises a CDR1, a CDR2, and a CDR3 sequence, the CDR1 sequence being independently selected from the group consisting of amino acid residues 24-34 of SEQ ID NO: 5, 9, 13, 21, 33, 37, 29, and 17, and amino acid residues 24-40 of SEQ ID NO: 1, 25, 41, and 45; the CDR2 sequence being independently selected from the group consisting of amino acid residues 50-56 of SEQ ID NO: 5, 9, 13, 21, 33, 37, 29, and 17, and amino acid residues 56-62 of SEQ ID NO: 1, 25, 41, and 45; and the CDR3 sequence being independently selected from the group consisting of amino acid residues 89-97 of SEQ ID NO: 5, 29, and 17, amino acid residues 89-98 of SEQ ID NO: 9, amino acid residues 89-96 of SEQ ID NO: 13, 21, 33, and 37, amino acid residues 95-103 of SEQ ID NO: 1, 25, and 41, and amino acid residues 95-102 of SEQ ID NO: 45. In one embodiment, the antibody preferably has a binding affinity for IL-8 of at least about 10 pM.

In a particular embodiment, a monoclonal antibody that specifically binds IL-8 with high-affinity comprises a light chain CDR1 sequence, CDR2 sequence and CDR3 sequence, comprising amino acid residues 24-34, 50-56 and 89-96 of SEQ ID NO: 33.

In another aspect, the invention relates to an antibody that binds to the same epitope on IL-8 as an antibody comprising a heavy chain amino acid sequence comprising SEQ ID NO: 35 and a light chain amino acid sequence comprising SEQ ID NO: 33.

In another aspect the invention provides a therapeutic composition comprising a high-affinity anti-IL-8 antibody in combination with a pharmaceutically acceptable carrier. In some embodiments the antibody is may be linked to a radioisotope or toxin.

In another aspect, the invention provides a method for the treatment of a disease or disorder, comprising administering to the patient an effective amount of a high-affinity anti-IL-8 antibody. The patient is preferably a mammalian patient, more preferably a human patient. In one embodiment the patient is suffering from an inflammatory disorder. In other embodiments the disease to be treated is a cancer, such as malignant melanoma. In particular embodiments, one or more high-affinity anti-IL-8 antibodies are used to treat a disease or disorder selected from the group consisting of bacterial pneumonia, asthma, ulcerative colitis, COPD, chronic bronchitis, emphysema, bronchiectasis, immunoglobulin deficiency, and cystic fibrosis.

Other embodiments provide an system for the detection of IL-8 in mammalian tissues, fluids or cells. The assay may be used to screen patients for a disease or disorder associated with changes in levels of IL-8, such as bacterial pneumonia, asthma, ulcerative colitis, COPD, chronic bronchitis, emphysema, bronchiectasis, immunoglobulin deficiency, cystic fibrosis, or other diseases associated with changes in levels and/or activity of IL-8. The system preferably comprises a package containing, in an amount sufficient to perform at least one assay, a composition containing a high-affinity anti-IL-8 antibody. This antibody composition can be, for example, in liquid solution or attached to a solid-phase matrix. The system also contains a detectable label for indicating the presence of antibody molecules in any immunoreaction products formed upon contacting a sample from a patient with the antibody composition.

BRIEF DESCRIPTION OF THE DRAWINGS

The invention will be better understood from the Detailed Description and from the appended drawings, which are meant to illustrate and not to limit the invention, and wherein:

FIG. 1A is a sequence listing of examples of the light and heavy chain amino acid sequences of particular antibodies directed to IL-8.

FIG. 1B is a continued sequence listing of examples of the light and heavy chain amino acid sequences of particular antibodies directed to IL-8.

FIG. 1C is a continued sequence listing of examples of the light and heavy chain amino acid sequences of particular antibodies directed to IL-8.

FIG. 2A is a sequence listing of examples of the light and heavy chain nucleic acid sequences that encode particular antibodies directed to IL-8.

FIG. 2B is a continued sequence listing of examples of the light and heavy chain nucleic acid sequences that encode particular antibodies directed to IL-8.

FIG. 2C is a continued sequence listing of examples of the light and heavy chain nucleic acid sequences that encode particular antibodies directed to IL-8.

FIG. 2D is a continued sequence listing of examples of the light and heavy chain nucleic acid sequences that encode particular antibodies directed to IL-8.

FIG. 2E is a continued sequence listing of examples of the light and heavy chain nucleic acid sequences that encode for antibodies directed to IL-8.

FIG. 4A is an alignment of the amino acid sequences of the heavy chain of several anti-IL-8 antibodies.

FIG. 4B is an alignment of the amino acid sequences of the light chain of several anti-IL-8 antibodies.

FIG. 5 shows the alignment of Filamentous phage-displaying peptides with an IL-8 epitope and the consensus sequence among these peptides.

FIG. 8 depicts various peptides of IL-8 and identifies the peptides that bound to ABXha-IL-8 and ABX-IL-8.

FIG. 9 displays sequences that are bound by 809 ABXha-IL-8, but not by ABX-IL-8.

FIG. 10 displays sequences that are bound by 928 ABXha-IL-8, but not by ABX-IL-8.

DETAILED DESCRIPTION

Figure 3:
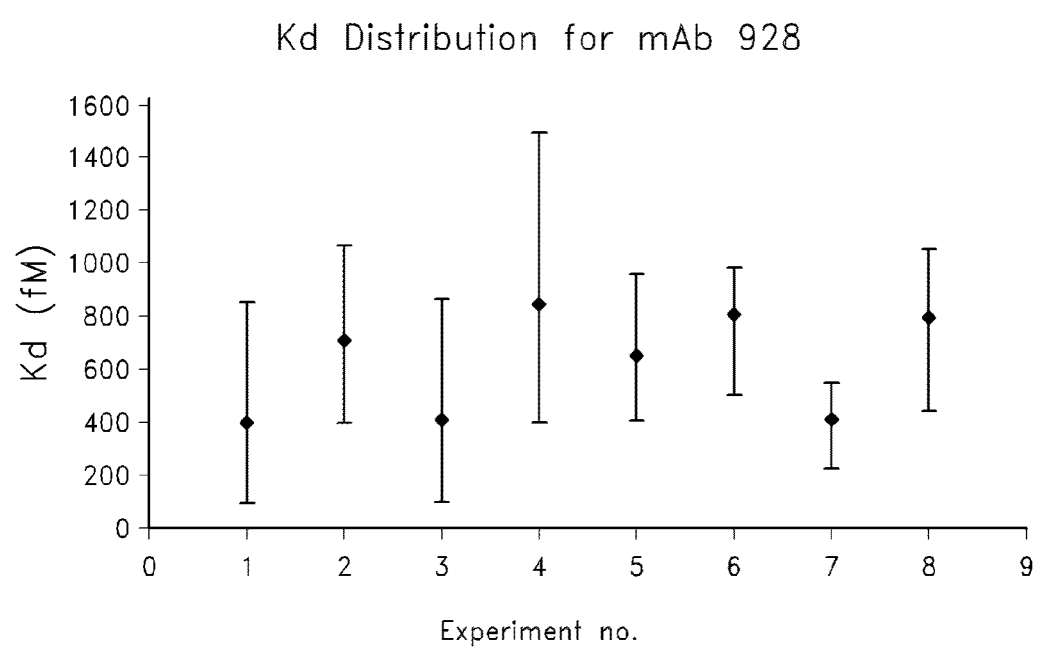
FIG. 3 is a graph displaying the distribution of Kds for various experiments examining the affinity of mAb 928 for IL-8.

Improvements in mAb affinity can provide improvements in potency. Thus, it is desirable to identify antibodies that recognize IL-8 with high affinity (a low "$K_d$"). The creation of such antibodies is described herein. In some embodiments, binding of these antibodies or fragments thereof prevents the interaction of IL-8 with other molecules, such as the IL-8 receptor, and thereby reduces the biological activity of IL-8. As a result, the antibodies can be used to treat diseases or disorders related to IL-8 activity. They may also be used, for example, to identify changes in the levels of IL-8 in a subject and thus can be used to diagnose disorders associated with such changes. In some embodiments, the antibodies of interest are those that can bind to IL-8 with a $K_d$ of less than 10 pM, preferably less than 1 pM, and more preferably less than 500 fM. These antibodies can have an especially high affinity for IL-8.

The diseases involving IL-8 that can be treated and/or diagnosed with the high-affinity IL-8 antibodies disclosed herein include, without limitation, bacterial pneumonia, asthma, ulcerative colitis, COPD, chronic bronchitis, emphysema, bronchiectasis, immunoglobulin deficiency, psoriasis and cystic fibrosis. In association with such diagnosis and/or treatment, articles of manufacture comprising the anti-IL-8 antibodies described herein are also provided.

Particular epitopes of IL-8 bound by the antibodies are also identified. For example, the epitope comprising the amino acid sequence LRCQCIKTYSKPFHPKFIKE (SEQ ID NO: 62), as well as subparts thereof, are recognized by some of the IL-8 antibodies described below. Additional antibodies can be created that are directed against these epitopes and used to diagnose and treat IL-8 associated diseases and disorders. For example, in some embodiments, the antibody of interest binds to IL-8 through one of the disclosed peptide fragments or "antigenic fragements", e.g., LRCQCIKTYSKPFHPK-FIKE (SEQ ID NO: 62), KPXPXF (SEQ ID NO: 63), and/or KPFHPKF (SEQ ID NO: 64). In some embodiments, the antibodies that bind to one or more of these fragments have a high affinity for IL-8 as well. These antibodies can have a $K_d$ that is less than 10 pM, 1 pM, 0.5 pM, and 0.1 pM.

Definitions:

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. See e.g. Singleton et al., *Dictionary of Microbiology and Molecular Biology* 2nd ed., J. Wiley & Sons (New York, N.Y. 1994); Sambrook et al. *Molecular Cloning: A Laboratory Manual* (2d ed., Cold Spring Harbor Laboratory Press, Cold Spring Harbor, N.Y. (1989)), which is incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As used herein, the terms "IL-8," and "IL8" refer to human interleukin-8, which is also known in the art as neutrophil-activating protein, neutrophil chemotactic factor (NCF) and T-cell chemotactic factor.

The term "ABX-IL-8 antibody" refers to a particular human anti-IL-8 antibody developed by Abgenix, Inc. of Fremont, Calif. In particular, it is the fully human monoclonal antibody generated with XenoMouse® technology, discussed in a Press Release from Abgenix, Inc., on Jan. 3, 2002, and further discussed in Yang et al., *J. Leukoc. Biol.*, 66 (3):401-410 (1999). "ABXha-IL-8 antibody" refers to a "high affinity" anti-IL-8 antibody, which is described herein.

The term "ABXha-IL-8 epitope" when used herein refers to an epitope on the IL-8 antigen that is capable of specifically binding to the ABXha-IL-8 antibody. The "ABXha-IL-8 epitope" preferably comprises the proline at amino acid position 16 of IL-8, more preferably the amino acid sequence KPXPXF (SEQ ID NO: 63) which corresponds to amino acid residues 15 to 21 of IL-8 and most preferably the amino acid sequence "LRCQCIKTYSKPFHPKFIKE" (SEQ ID NO: 62). The epitope may be linear or conformational. As noted below additional epitopes are also relevant.

As used herein, a "high-affinity" antibody is an antibody with a $K_d$ for IL-8 of less than 100 pM, even more preferably less than 10 pM, still more preferably less than 1 pM, yet more preferably less than 100 fM and even more preferably less than 10 fM.

Many of the particular antibodies described herein possess high affinity for IL-8. For example, antibody 809 has a $K_d$ of about 2.23 pM, antibody 837 has a $K_d$ of about 10.9 pM, antibody 861 has a $K_d$ of about 2.89 pM and antibody 928 has a $K_d$ of about 0.06 pM. These are high-affinity antibodies that have not undergone affinity maturation.

An antibody with a "low $K_d$" is one that will bind with high affinity to an antigen.

"Polymerase chain reaction" or "PCR" refers to a procedure or technique in which minute amounts of a specific piece of nucleic acid, RNA and/or DNA, are amplified as described, for example, in U.S. Pat. No. 4,683,195. Oligonucleotide primers can be designed; these primers will be identical or similar in sequence to a portion of the opposite strands of the template to be amplified. The 5' terminal nucleotides of the two primers can coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.* 51:263 (1987); Erlich, ed., *PCR Technology* (Stockton Press, NY, 1989). As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

"Native antibodies and immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains (Chothia et al. *J. Mol. Biol.* 186:651 (1985; Novotny and Haber, *Proc. Natl. Acad. Sci. U.S.A.* 82:4592 (1985); Chothia et al., *Nature* 342:877-883 (1989)).

The term "antibody" is used herein in the broadest sense and covers, without limitation, intact monoclonal antibodies, polyclonal antibodies, multispecific antibodies (e.g. bispecific antibodies) formed from at least two intact antibodies, antibody fragments including Fab and F(ab')2, so long as they exhibit the desired biological activity and antibody sequence variants. The "light chains" of antibodies (immunoglobulins) from any vertebrate species can be assigned to one of two clearly distinct types, called κ and λ, based on the amino acid sequences of their constant domains. Binding fragments of an antibody can be produced by recombinant DNA techniques, or by enzymatic or chemical cleavage of intact antibodies. Binding fragments include Fab, Fab', $F(ab')_2$, Fv, and single-chain antibodies. An antibody other than a "bispecific" or "bifunctional" antibody is understood to have each of its binding sites identical. An antibody substantially inhibits adhesion of a receptor to a counterreceptor when an excess of antibody reduces the quantity of receptor bound to counter-receptor by at least about 20%, 40%, 60% or 80%, and more usually greater than about 85% (as measured in an in vitro competitive binding assay).

Depending on the amino acid sequence of the constant domain of their heavy chains, intact antibodies can be assigned to different "classes." There are five major classes of intact antibodies: IgA, IgD, IgE, IgG, and IgM, and several of these can be further divided into "subclasses" (isotypes), e.g., IgG1, IgG2, IgG3, IgG4, IgA1, and IgA2. The heavy-chain constant domains that correspond to the different classes of antibodies are called α, δ, ε, γ, and μ, respectively. The subunit structures and three-dimensional configurations of different classes of immunoglobulins are well known.

The term "mAb" refers to a monoclonal antibody. The term "monoclonal antibody" as used herein refers to an antibody obtained from a population of substantially homogeneous antibodies, i.e., the individual antibodies comprising the population are identical except for possible naturally occurring mutations that can be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they can be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention can be made by the hybridoma method first described by Kohler et al., Nature, 256:495 (1975), or can be made by recombinant DNA methods (see, e.g., U.S. Pat. No. 4,816,567 and U.S. Pat. No. 5,627,052). The "monoclonal antibodies" can also be isolated from phage antibody libraries, for example by using the techniques described in Clackson et al, Nature, 352:624-628 (1991) and Marks et al., J. Mol. Biol., 222:581-597 (1991).

An "isolated" antibody is one which has been identified and separated and/or recovered from a component of its natural environment. Contaminant components of its natural environment are materials which would interfere with diagnostic or therapeutic uses for the antibody, and can include enzymes, hormones, and other proteinaceous or nonproteinaceous solutes. In preferred embodiments, the antibody will be purified (1) to greater than 95% by weight of antibody as determined by the Lowry method, and terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

A "neutralizing antibody" is an antibody molecule which is able to eliminate or significantly reduce a biological activity of a target antigen to which is binds. Accordingly, a "neutralizing" IL-8 antibody is capable of eliminating or significantly reducing an IL-8 activity. For example, a neutralizing IL-8 antibody can reduce or eliminate binding to the IL-8 receptor. In another example a neutralizing IL-8 antibody can reduce or prevent chemotaxis by binding to IL-8 and clearing IL-8 from a site of inflammation.

"Antibody-dependent cell-mediated cytotoxicity" and "ADCC" refer to a cell-mediated reaction in which non-specific cytotoxic cells that express Ig Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcRs expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. Nos. 5,500,362, or 5,821,337 can be performed. Useful effector cells for such assays include peripheral blood mononuclear cells (PBMC) and Natural Killer (NK) cells. Alternatively, or additionally, ADCC activity of the molecule of interest can be assessed in vivo, e.g., in a animal model such as that disclosed in Clynes et al. PNAS (USA) 95:652-656 (1988).

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the Ig light-chain and heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al. (1991). The constant domains are not involved directly in binding an antibody to an antigen, but exhibit various effector functions, such as participation of the antibody in antibody-dependent cellular toxicity.

Digestion of antibodies with the enzyme papain results in two identical antigen-binding fragments, known also as "Fab" fragments, and a "Fc" fragment, having no antigen-binding activity but having the ability to crystallize. Digestion of antibodies with the enzyme pepsin results in the $F(ab')_2$ fragment in which the two arms of the antibody molecule remain linked and comprise two-antigen binding sites. The $F(ab')_2$ fragment has the ability to crosslink antigen.

"Fab" when used herein refers to a fragment of an antibody which comprises the constant domain of the light chain and the CH1 domain of the heavy chain.

"Fv" when used herein refers to the minimum fragment of an antibody that retains both antigen-recognition and antigen-binding sites. In a two-chain Fv species, this region consists of a dimer of one heavy- and one light-chain variable domain in tight, non-covalent association. In a single-chain Fv species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The term "hypervariable region" when used herein refers to the amino acid residues of an antibody which are responsible for antigen-binding. The hypervariable region generally comprises amino acid residues from a "complementarity determining region" or "CDR" (e.g. residues 24-34 (L1), 50-62 (L2), and 89-97 (L3) in the light chain variable domain and 31-55 (H1), 50-65 (H2) and 95-102 (H3) in the heavy chain variable domain; Kabat et al., Sequences of Proteins of Immunological Interest, $5^{th}$ Ed. Public Health Service, National Institutes of Health, Bethesda, Md. (1991)) and/or those residues from a "hypervariable loop" (e.g. residues 26-32 (L1), 50-52 (L2) and 91-96 (L3) in the light chain variable domain and 26-32 ((H1), 53-55 (H2) and 96-101 (H3) in the heavy chain variable domain; Chothia and Lesk J. Mol. Biol. 196:901-917 (1987)). "Framework Region" or "FR" residues are those variable domain residues other than the hypervariable region residues as herein defined.

"Complementarity determining regions" or "CDRs" are parts of immunological receptors, such as antibodies, that make contact with a specific ligand and determine its specificity. The CDRs of immunological receptors are the most variable part of the receptor protein, giving receptors their diversity, and are carried on six loops at the distal end of the receptor's variable domains, three loops coming from each of the two variable domains of the receptor.

The term "epitope" is used to refer to binding sites for immunological receptors, particularly antibodies, on protein antigens. Epitopic determinants usually consist of chemically active surface groupings of molecules such as amino acids or sugar side chains and usually have specific three dimensional structural characteristics, as well as specific charge characteristics. An antibody is said to be specific, bind specifically, bind preferentially or similar such term, when its ability to bind the specific or preferential target is greater than its ability to bind another molecule.

The term "antigenic fragment" denotes a protein fragment, in this case an IL-8 protein fragment, 8 to 20 amino acids in length, more preferably 10 to 16 amino acids and most preferably 12 amino acids. The antigenic fragments disclosed herein can be especially useful for developing antibodies with very small $K_D$S to IL-8.

The term "amino acid" or "amino acid residue," as used herein, refers to naturally occurring L amino acids or to D amino acids as described further below with respect to variants. The commonly used one and three-letter abbreviations for amino acids are used herein (Bruce Alberts et al., *Molecular Biology of the Cell*, Garland Publishing, Inc., New York (3d ed. 1994)).

The term "XENOMAX®" refers to use of the "Selected Lymphocyte Antibody Method" (Babcook et al., *Proc. Natl. Acad. Sci. USA*, i93:7843-7848 (1996) and discussed in the Examples below), when used in conjunction with XENOMOUSE® animals. The generation of the first XenoMouse mouse strains were described in Green et al. (Nature Genetics 7:13-21 (1994)). The XenoMouse strains were engineered with yeast artificial chromosomes (YACs) containing 245 kb and 190 kb-sized germline configuration fragments of the human heavy chain locus and kappa light chain locus, respectively, which contained core variable and constant region sequences. Id. The human Ig containing YACs proved to be compatible with the mouse system for both rearrangement and expression of antibodies and were capable of substituting for the inactivated mouse Ig genes. This was demonstrated by their ability to induce B-cell development, to produce an adult-like human repertoire of fully human antibodies, and to generate antigen-specific human mAbs. These results also suggested that introduction of larger portions of the human Ig loci containing greater numbers of V genes, additional regulatory elements, and human Ig constant regions might recapitulate substantially the full repertoire that is characteristic of the human humoral response to infection and immunization. The work of Green et al. was recently extended to the introduction of greater than approximately 80% of the human antibody repertoire through introduction of megabase sized, germline configuration YAC fragments of the human heavy chain loci and kappa light chain loci, respectively. (See Mendez et al. Nature Genetics 15:146-156 (1997) and U.S. patent application Ser. No. 08/759,620, filed Dec. 3, 1996, the disclosures of which are hereby incorporated by reference).

The production of the XenoMouse mice is further discussed and delineated in U.S. patent application Ser. Nos. 07/466,008, filed Jan. 12, 1990, 07/610,515, filed Nov. 8, 1990, 07/919,297, filed Jul. 24, 1992, 07/922,649, filed Jul. 30, 1992, filed 08/031,801, filed Mar. 15, 1993, 08/112,848, filed Aug. 27, 1993, 08/234,145, filed Apr. 28, 1994, 08/376, 279, filed Jan. 20, 1995, 08/430, 938, Apr. 27, 1995, 08/464, 584, filed Jun. 5, 1995, 08/464,582, filed Jun. 5, 1995, 08/463, 191, filed Jun. 5, 1995, 08/462,837, filed Jun. 5, 1995, 08/486, 853, filed Jun. 5, 1995, 08/486,857, filed Jun. 5, 1995, 08/486, 859, filed Jun. 5, 1995, 08/462,513, filed Jun. 5, 1995, 08/724, 752, filed Oct. 2, 1996, and 08/759,620, filed Dec. 3, 1996 and U.S. Pat. Nos. 6,162,963, 6,150,584, 6,114,598, 6,075,181, and 5,939,598 and Japanese Patent Nos. 3 068 180 B2, 3 068 506 B2, and 3 068 507 B2. See also Mendez et al. *Nature Genetics* 15:146-156 (1997) and Green and Jakobovits *J. Exp. Med.* 188:483-495 (1998). See also European Patent No., EP 0 463 151 B1, grant published Jun. 12, 1996, International Patent Application No. WO 94/02602, published Feb. 3, 1994, International Patent Application No. WO 96/34096, published Oct. 31, 1996, WO 98/24893, published Jun. 11, 1998, WO 00/6310, published Dec. 21, 2000, WO 03/47336. The disclosures of each of the above-cited patents, applications, and references are hereby incorporated by reference in their entirety.

The term "SC" refers to single cell and a particular XENOMAX® derived antibody can be referred to as SC followed by three digits, or just three digits, referring to the single cell number from which the antibody was derived herein.

The term "SLAM®" refers to the "Selected Lymphocyte Antibody Method" (Babcook et al., *Proc. Natl. Acad. Sci. USA*, i93:7843-7848 (1996), and Schrader, U.S. Pat. No. 5,627,052), both of which are incorporated by reference in their entireties. SLAM is described in more detail below. In brief, SLAM is an approach to the generation of monoclonal antibodies based on the molecular cloning and expression of immunoglobulin variable region cDNAs generated from single lymphocytes that were selected for the production of specific antibodies. Single cells can be selected using an antigen specific hemolytic plaque assay. Next, heavy and light-chain variable region cDNAs are rescued from single cells by reverse transcriptase-PCR and expressed in the context of human immunoglobulin constant regions. These recombinant monoclonal antibodies will replicate the target specificities of the original antibody-forming cells."

The term "disease state" refers to a physiological state of a cell or of a whole mammal in which an interruption, cessation, or disorder of cellular or body functions, systems, or organs has occurred.

The term "symptom" means any physical or observable manifestation of a disorder, whether it is generally characteristic of that disorder or not. The term "symptoms" can mean all such manifestations or any subset thereof.

"Inflammation" as used herein is a general term for the local accumulation of fluid, plasma proteins, and white blood cells that is initiated by physical injury, infection, or a local immune response. Many different forms of inflammation are associated with different diseases. ""Inflammation-associated" diseases include, for example, psoriasis, rheumatoid arthritis, and inflammatory bowel disease. Other inflammation-associated diseases are discussed herein.

"Tumor", as used herein, refers to abnormal growth both in rate and structure that arises from normal tissue, but serves no apparent function.

"Cancer" when used herein refers to the condition in mammals that is characterized by the uncontrolled growth and spread of abnormal cells. Examples of "cancer" include malignant melanoma, head and neck cancer, breast cancer, non-small cell lung cancer, ovarian cancer and brain cancer.

A "disorder" or "disease" as used herein refers to an abnormal condition that affects one or more of the body processes. Such a "disease" or "disorder" can be prevented or its severity reduced with treatment. Some examples of disorders or diseases that may be treated using the disclosed antibodies include, without limitation, tumors, in particular malignant tumor, malignant melanoma, renal cell carcinoma (RCC), head and neck cancer, breast cancer, non-small cell lung cancer, ovarian cancer and brain cancer and esophageal tumors; inflammatory diseases, in particular psoriasis, rheumatoid arthritis, and inflammatory bowel disease; and pulmonary disorders, such as chronic obstructive pulmonary disease (COPD) and idiopathic pulmonary fibrosis; and acute inflammatory diseases, such as gastrointestinal diseases. These are examples of "IL-8 related diseases" or disorders. An "IL-8 related disorder" or disease is a disorder or disease that results from the over expression of IL-8 and/or increased activity of IL-8 or a receptor of IL-8.

As used herein, "antineoplastic agent" refers to agents that have the functional property of inhibiting a development or progression of a neoplasm in a human, particularly a malignant (cancerous) lesion, such as a melanoma, carcinoma, sarcoma, lymphoma, or leukemia. Inhibition of metastasis is frequently a property of antineoplastic agents.

The terms "treat" and "treatment" refer to both therapeutic treatment and prophylactic or preventative measures, wherein the object is to prevent or slow down (lessen) an undesired physiological change or disorder, such as the development or spread of cancer or an inflammatory disease. In some embodiments, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The term "patient" includes humans, mammals, and veterinary subjects.

The term "body fluid" includes any fluid which at some point is or has been in a body. This can include, for example and without limitation, blood, bile, stomach acid, mucus, urine, and cerebrospinal fluid.

"Administer," for purposes of treatment, means to deliver to a patient. Such delivery can be by any known means, for example intravenous, intraperitoneal, by inhalation, intramuscular, subcutaneous, oral, topical, transdermal, or surgical.

"Therapeutically effective amount," for purposes of treatment, means an amount such that an observable change in the patient's condition and/or symptoms could result from its administration, either alone or in combination with other treatment.

A "pharmaceutically acceptable" carrier for the purposes of treatment, is a physical embodiment that can be administered to a patient. Pharmaceutically acceptable carriers, or vehicles, can be, but are not limited to, pills, capsules, caplets, tablets, orally administered fluids, injectable fluids, sprays, aerosols, lozenges, neutraceuticals, creams, lotions, oils, solutions, pastes, powders, vapors, or liquids. One example of a pharmaceutically acceptable vehicle is a buffered isotonic solution, such as phosphate buffered saline (PBS).

"Neutralize," for purposes of treatment, means to partially or completely suppress chemical and/or biological activity.

"Down-regulate," for purposes of treatment, means to lower the level of a particular target composition.

The term "polypeptide" is used herein as a generic term to refer to native protein, fragments, or analogs of a polypeptide sequence. Hence, native protein, fragments, and analogs are species of the polypeptide genus. Preferred polypeptides comprise the human heavy chain immunoglobulin molecules represented in FIGS. 1A, 1B, 1C, 4A, and 4B and the human kappa light chain immunoglobulin molecules represented by FIGS. 1A, 1B, 1C, 4A, and 4B, (e.g., odd SEQ ID NO: 1-47) as well as antibody molecules formed by combinations comprising the heavy chain immunoglobulin molecules with light chain immunoglobulin molecules, such as the kappa light chain immunoglobulin molecules, and vice versa, as well as variants, fragments and analogs thereof.

The term "isolated protein" as used herein means a protein of cDNA, recombinant RNA, or synthetic origin or some combination thereof, which by virtue of its origin, or source of derivation, the "isolated protein" (1) is not associated with proteins found in nature, (2) has been separated from one or more other proteins from the same source, e.g., free of murine proteins, (3) is expressed by a cell from a different species, or (4) does not occur in nature.

The term "oligonucleotide" referred to herein includes naturally occurring, and modified nucleotides linked together by naturally occurring, and non-naturally occurring oligonucleotide linkages. Oligonucleotides are a polynucleotide subset generally comprising a length of 200 bases or fewer. Preferably, oligonucleotides are 10 to 60 bases in length and most preferably 12, 13, 14, 15, 16, 17, 18, 19, or 20 to 40 bases in length. Oligonucleotides are usually single stranded, e.g., for probes; although oligonucleotides can be double stranded, e.g., for use in the construction of a gene mutant. Oligonucleotides can be either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phosphoraniladate, phosphoroamidate, and the like. See e.g., LaPlanche et al. *Nucl. Acids Res.* 14:9081 (1986); Stec et al. *J. Am. Chem. Soc.* 106:6077 (1984); Stein et al. *Nucl. Acids Res.* 16:3209 (1988); Zon et al. *Anti-Cancer Drug Design* 6:539 (1991); Zon et al. *Oligonucleotides and Analogues: A Practical Approach*, pp. 87-108 (F. Eckstein, Ed., Oxford University Press, Oxford England (1991)); Stec et al. U.S. Pat. No. 5,151,510; Uhlmann and Peyman *Chemical Reviews* 90:543 (1990), the disclosures of which are hereby incorporated by reference. An oligonucleotide can include a label for detection, if desired.

The term "polynucleotide" as referred to herein means a polymeric form of nucleotides of at least 10 bases in length, either ribonucleotides or deoxynucleotides or a modified form of either type of nucleotide. The term includes single and double stranded forms of DNA.

The nucleic acids described herein, and fragments and variants thereof, can be used, by way of nonlimiting example, (a) to direct the biosynthesis of the corresponding encoded proteins, polypeptides, fragments and variants as recombinant or heterologous gene products, (b) as probes for detection and quantification of the nucleic acids disclosed herein, (c) as sequence templates for preparing antisense molecules, and the like. Such uses are described more fully below.

The term "naturally-occurring" as used herein refers to the fact that an object can be found in nature. For example, a polypeptide or polynucleotide sequence that can be isolated from a source in nature and which has not been intentionally modified by man in the laboratory or otherwise is naturally-occurring.

The term "isolated polynucleotide" as used herein shall mean a polynucleotide of genomic, cDNA, or synthetic origin or some combination thereof, which (1) is not associated with all or a portion of one or more polynucleotides in which the "isolated polynucleotide" is found in nature or with which it is associated in nature, (2) is operably linked to a polynucleotide which it is not linked to in nature, or (3) does not occur in nature.

The term "operably linked" as used herein refers to positions of components so described that are in a relationship permitting them to function in their intended manner. For example, a control sequence "operably linked" to a coding sequence is connected in such a way that expression of the coding sequence is achieved under conditions compatible with the control sequences.

The term "selectively hybridize" referred to herein means to detectably and specifically bind. Polynucleotides, oligonucleotides and fragments thereof selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, or antibody fragments and a nucleic acid sequence of interest will be at least 80%, and more typically with preferably increasing homologies of at least 85%, 90%, 95%, 99%, and 100%.

Two amino acid sequences are "homologous" if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least about 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in *Atlas of Protein Sequence and Structure*, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program.

The term "corresponds to" is used herein to mean that a polynucleotide sequence is homologous (i.e., is identical, not strictly evolutionarily related) to all or a portion of a reference polynucleotide sequence, or that a polypeptide sequence is identical to all or a portion of a reference polypeptide sequence.

In contradistinction, the term "complementary to" is used herein to mean that the complementary sequence is homologous to all or a portion of a reference polynucleotide or polypeptide sequence. For illustration, the nucleotide sequence "TATAC" corresponds to a reference sequence "TATAC" and is complementary to a reference sequence "GTATA".

The following terms are used to describe the sequence relationships between two or more polynucleotide or amino acid sequences: "reference sequence", "comparison window", "sequence identity", "percentage of sequence identity", and "substantial identity". A "reference sequence" is a defined sequence used as a basis for a sequence comparison. A reference sequence can be a subset of a larger sequence, for example, as a segment of a full-length cDNA or gene sequence given in a sequence listing or can comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences can each (1) comprise a sequence (i.e., a portion of the complete polynucleotide or amino acid sequence) that is similar between the two molecules, and (2) can further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least about 18 contiguous nucleotide positions or about 6 amino acids wherein the polynucleotide sequence or amino acid sequence is compared to a reference sequence of at least 18 contiguous nucleotides or 6 amino acid sequences and wherein the portion of the polynucleotide sequence in the comparison window can include additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window can be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci.* (*U.S.A.*) 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), GENEWORKS™, or MACVECTOR® software packages), or by inspection, and the best alignment (i.e., resulting in the highest percentage of homology over the comparison window) generated by the various methods is selected.

By "contiguous," it is meant that the parts (e.g., individual amino acids, nucleic acids, or antibody segments such as CDRs and FRs) are immediately abutting each other without anything significant blocking or intervening in their association.

The term "control sequence" as used herein refers to polynucleotide sequences which are necessary to effect the expression and processing of coding sequences to which they are connected. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

As used herein, the twenty conventional amino acids and their abbreviations follow conventional usage. See Immunology—A Synthesis (2nd Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as alpha-, alpha-disubstituted amino acids, N-alkyl amino acids, lactic acid, and other unconventional amino acids can also be suitable components for polypeptides in some embodiments. Examples of unconventional amino acids include, without limitation, 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U, or I) or amino acid residue occurs in both sequences to yield the number of matched positions, dividing the number of matched positions by the total number of positions in the comparison window (i.e., the window size), and multiplying the result by 100 to yield the percentage of sequence identity.

The term "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more preferably at least 99 percent sequence identity, as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which can include deletions or additions which total 20 percent or less of the reference sequence over the comparison window. The reference sequence can be a subset of a larger sequence. Preferably, residue positions which are not identical differ by conservative amino acid substitutions. Preferred antibody variants comprise amino acid sequences that are substantially identical to those disclosed herein.

Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences."

Antibody "variants," comprising variations in the amino acid sequences of antibodies or immunoglobulin molecules are contemplated as being encompassed by the present embodiments. Variations in the amino acid sequence maintain at least 75%, more preferably at least 80%, 90%, 95%, and most preferably 99% sequence identity compared to the naturally occurring sequence. In particular, conservative amino acid replacements are contemplated. Conservative replacements are those that take place within a family of amino acids that are related in their side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Those of skill in the art can recognize sequence motifs and structural conformations that can be used to define structural and functional domains.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) can be made in the naturally-occurring sequence. In some embodiments, these substitutions are preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. Nature 354:105 (1991), which are each incorporated herein by reference.

The term "polypeptide fragment" as used herein refers to a polypeptide that has an amino-terminal and/or carboxy-terminal deletion, but where the remaining amino acid sequence is identical to the corresponding positions in the naturally-occurring sequence deduced, for example, from a full-length cDNA sequence. Fragments typically are at least 5, 6, 8 or 10 amino acids long, preferably at least 14 amino acids long, more preferably at least 20 amino acids long, usually at least 50 amino acids long, and even more preferably at least 70 amino acids long.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In certain situations, the label or marker can also be therapeutic. Various methods of labeling polypeptides and glycoproteins are known in the art and can be used. Examples of labels for polypeptides include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

The term "pharmaceutical agent or drug" as used herein refers to a chemical compound or composition capable of inducing a desired therapeutic effect when properly administered to a patient. Other chemistry terms herein are used according to conventional usage in the art, as exemplified by The McGraw-Hill Dictionary of Chemical Terms (Parker, S., Ed., McGraw-Hill, San Francisco (1985)), incorporated herein by reference).

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

Antibody Structure

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety). The variable regions of each light/heavy chain pair form the antibody binding site.

Thus, an intact antibody has two binding sites. Except in bifunctional or bispecific antibodies, the two binding sites are the same.

The chains all exhibit the same general structure of relatively conserved framework regions (FR) joined by three hyper variable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987); Chothia et al. Nature 342:878-883 (1989).

A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann Clin. Exp. Immunol. 79: 315-321 (1990), Kostelny et al. J. Immunol. 148:1547-1553 (1992). Production of bispecific antibodies can be a relatively labor intensive process compared with production of conventional antibodies and yields and degree of purity are generally lower for bispecific antibodies. Bispecific antibodies do not exist in the form of fragments having a single binding site (e.g., Fab, Fab', and Fv).

Human Antibodies and Humanization of Antibodies

Human antibodies avoid some of the problems associated with antibodies that possess murine or rat variable and/or constant regions. The presence of such murine or rat derived proteins can lead to the rapid clearance of the antibodies or can lead to the generation of an immune response against the antibody by a patient. In order to avoid the utilization of murine or rat derived antibodies, fully human antibodies can be generated through the introduction of human antibody function into a rodent so that the rodent produces fully human antibodies.

One method for generating fully human antibodies is through the use of XENOMOUSE® strains of mice which have been engineered to contain 245 kb and 190 kb-sized germline configuration fragments of the human heavy chain locus and kappa light chain locus. See Green et al. Nature Genetics 7:13-21 (1994). The XENOMOUSE® strains are available from Abgenix, Inc. (Fremont, Calif.).

The production of the XENOMOUSE® is further discussed and delineated in U.S. patent application Ser. Nos. 07/466,008, filed Jan. 12, 1990, 07/610,515, filed Nov. 8, 1990, 07/919,297, filed Jul. 24, 1992, 07/922,649, filed Jul. 30, 1992, filed 08/031,801, filed Mar. 15, 1993, 08/112,848, filed Aug. 27, 1993, 08/234,145, filed Apr. 28, 1994, 08/376, 279, filed Jan. 20, 1995, 08/430, 938, Apr. 27, 1995, 08/464, 584, filed Jun. 5, 1995, 08/464,582, filed Jun. 5, 1995, 08/463, 191, filed Jun. 5, 1995, 08/462,837, filed Jun. 5, 1995, 08/486, 853, filed Jun. 5, 1995, 08/486,857, filed Jun. 5, 1995, 08/486, 859, filed Jun. 5, 1995, 08/462,513, filed Jun. 5, 1995, 08/724, 752, filed Oct. 2, 1996, and 08/759,620, filed Dec. 3, 1996 and U.S. Pat. Nos. 6,162,963, 6,150,584, 6,114,598, 6,075,181, and 5,939,598 and Japanese Patent Nos. 3 068 180 B2, 3 068 506 B2, and 3 068 507 B2. See also Mendez et al. Nature Genetics 15:146-156 (1997) and Green and Jakobovits J. Exp. Med. 188:483-495 (1998). See also European Patent No., EP 0 463 151 B1, grant published Jun. 12, 1996, International Patent Application No. WO 94/02602, published Feb. 3, 1994, International Patent Application No. WO 96/34096, published Oct. 31, 1996, WO 98/24893, published Jun. 11, 1998, WO 00/76310, published Dec. 21, 2000. The disclosures of each of the above-cited patents, applications, and references are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and a second constant region (preferably a gamma constant region) are formed into a construct for insertion into an animal. This approach is described in U.S. Pat. No. 5,545,807 to Surani et al. and U.S. Pat. Nos. 5,545,806, 5,625,825, 5,625,126, 5,633,425, 5,661, 016, 5,770,429, 5,789,650, 5,814,318, 5,877,397, 5,874,299, and 6,255,458 each to Lonberg and Kay, U.S. Pat. Nos. 5,591, 669 and 6,023.010 to Krimpenfort and Berns, U.S. Pat. Nos. 5,612,205, 5,721,367, and 5,789,215 to Berns et al., and U.S. Pat. No. 5,643,763 to Choi and Dunn, and GenPharm International U.S. patent application Ser. Nos. 07/574,748, filed Aug. 29, 1990, 07/575,962, filed Aug. 31, 1990, 07/810,279, filed Dec. 17, 1991, 07/853,408, filed Mar. 18, 1992, 07/904, 068, filed Jun. 23, 1992, 07/990,860, filed Dec. 16, 1992, 08/053,131, filed Apr. 26, 1993, 08/096,762, filed Jul. 22, 1993, 08/155,301, filed Nov. 18, 1993, 08/161,739, filed Dec. 3, 1993, 08/165,699, filed Dec. 10, 1993, 08/209,741, filed Mar. 9, 1994, the disclosures of which are hereby incorporated by reference. See also European Patent No. 0 546 073 B1, International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884 and U.S. Pat. No. 5,981,175, the disclosures of which are hereby incorporated by reference in their entirety. See further Taylor et al., 1992, Chen et al., 1993, Tuaillon et al., 1993, Choi et al., 1993, Lonberg et al., (1994), Taylor et al., (1994), and Tuaillon et al., (1995), Fishwild et al., (1996), the disclosures of which are hereby incorporated by reference in their entirety.

Kirin has also demonstrated the generation of human antibodies from mice in which, through microcell fusion, large pieces of chromosomes, or entire chromosomes, have been introduced. See European Patent Application Nos. 773 288 and 843 961, the disclosures of which are hereby incorporated by reference in their entireties.

Human anti-mouse antibody (HAMA) responses have also led the industry to prepare chimeric or otherwise humanized antibodies. While chimeric antibodies have a human constant region and a murine variable region, it is expected that certain human anti-chimeric antibody (HACA) responses will be observed, particularly in chronic or multi-dose utilizations of the antibody.

Preparation of Antibodies

Fully human, high-affinity monoclonal antibodies to IL-8 can be prepared using the XENOMOUSE® technology (Abgenix Inc., Freemont, Calif.). Such mice are capable of producing human immunoglobulin molecules and antibodies and are deficient in the production of murine immunoglobulin molecules and antibodies. Essentially, XENOMOUSE® lines of mice are immunized with an antigen of interest (e.g., IL-8). The antigen may be, for example and without limitation, full length IL-8 or a fragment of IL-8. In other embodiments the antigen is a fusion protein comprising at least a portion of IL-8. Immunization may be repeated multiple times as desired. Following immunization, lymphatic cells (such as B-cells) are recovered from mice that express antibodies, and the recovered cell lines are fused with a myeloid-type cell line to prepare immortal hybridoma cell lines. These hybridoma cell lines are screened and selected to identify hybridoma cell lines that produced antibodies specific to the antigen of interest and that have the desired properties.

In other embodiments, instead of being fused to myeloma cells to generate hybridomas, the cells isolated from immunized XENOMOUSE® lines of mice are screened further for antibodies that are reactive against the initial antigen, preferably IL-8. Such screening can include, for example, ELISA with IL-8, a competition assay with known antibodies that bind IL-8, and in vitro studies of the ability to neutralize IL-8.

Single B cells secreting antibodies of interest can then be isolated, for example by using an IL-8-specific hemolytic plaque assay (see, e.g., Babcook et al., *Proc. Natl. Acad. Sci. USA*, i93:7843-7848 (1996), describing "SLAM"). Cells targeted for lysis are preferably sheep red blood cells (SRBCs) coated with IL-8 antigen.

In the presence of a B cell culture secreting the immunoglobulin of interest and complement, the formation of a plaque indicates specific IL-8-mediated lysis of the target cells. The single antigen-specific plasma cell in the center of the plaque can be isolated and the genetic information that encodes the specificity of the antibody is isolated from the single plasma cell. Using reverse-transcriptase PCR, the DNA encoding the variable region of the antibody secreted can be cloned. Such cloned DNA can then be inserted into a suitable expression vector, such as pcDNA (Invitrogen), more preferably a vector containing the constant domains of immunoglobulin heavy and light chains. The generated vector can then be transfected into host cells, such as CHO cells.

Regardless of their initial source, anti-IL-8 antibodies can be produced in cell lines other than hybridoma cell lines. Sequences encoding particular antibodies, preferably in a vector, can be used for transformation of a suitable mammalian host cell. Transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740, 461, and 4,959,455 (which are hereby incorporated herein by reference). The transformation procedure used depends upon the host to be transformed. Methods for introducing heterologous polynucleotides into mammalian cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), human embryonic kidney cells (HEK) and other cell lines known in the art.

Transformed host cells are cultured in the appropriate nutrient media to produce the desired antibodies, which can be purified from the media using conventional techniques. The skilled artisan will be able to select the nutrient media and purification techniques depending on the particular circumstances. Further, as will be recognized by the skilled artisan, the media may be modified as appropriate for inducing promoters, selecting transformants, or amplifying the genes encoding the desired sequences.

The anti-IL-8 antibodies disclosed herein can be isotype switched to provide them with desirable properties. For example, in some embodiments, particularly in the context of therapeutic antibodies, the anti-IL-8 antibodies are preferably capable of fixing complement and participating in complement-dependent cytotoxicity (CDC). A number of isotypes of antibodies are capable of fixing complement, including, without limitation, murine IgM, murine IgG2a, murine IgG2b, murine IgG3, human IgM, human IgG1, and human IgG3. In other embodiments the isotype may be switched to provide properties such as extended half-life and slower clearance.

If desired, a human antibody possessing the desired affinity to IL-8 could be readily isotype switched to generate a human IgM, human IgG1, or human IgG3 isotype, while still possessing the same variable region. Such an antibody would then be capable of fixing complement and participating in CDC.

Thus, the anti-IL-8 antibodies that are generated need not initially possess the desired isotype but can be isotype switched using conventional techniques that are well known in the art. Such techniques include, without limitation, the use of direct recombinant techniques (see e.g., U.S. Pat. No. 4,816,397), cell-cell fusion techniques (see e.g., U.S. Pat. Nos. 5,916,771 and 6,207,418), among others. These techniques are well known in the art.

Briefly, in the cell-cell fusion technique, a myeloma or other cell line is prepared that possesses a heavy chain with a desired isotype and another myeloma or other cell line is prepared that possesses the light chain. Such cells are fused and a cell line expressing an intact antibody of the desired isotype can be isolated.

Accordingly, as antibody candidates are generated that meet desired "structural" attributes, they can be provided with certain "functional" attributes through isotype switching if desired.

Sequence Listing

The heavy chain and light chain variable region nucleotide and amino acid sequences of representative human anti-IL-8 antibodies, identified as described in the Examples below, are provided in the attached sequence listing, the contents of which are summarized in Table 1. The sequences themselves are displayed in FIGS. 1A-2E.

TABLE 1

| mAb ID No.: | Sequence | SEQ ID NO: |
|---|---|---|
| 33 | Amino acid sequence encoding the variable region of the heavy chain | 3 |
| | Nucleotide sequence encoding the variable region of the heavy chain | 4 |
| | Amino acid sequence encoding the variable region of the light chain | 1 |
| | Nucleotide sequence encoding the variable region of the light chain | 2 |
| 142 | Amino acid sequence encoding the variable region of the heavy chain | 7 |
| | Nucleotide sequence encoding the variable region of the heavy chain | 8 |
| | Amino acid sequence encoding the variable region of the light chain | 5 |
| | Nucleotide sequence encoding the variable region of the light chain | 6 |
| 203 | Amino acid sequence encoding the variable region of the heavy chain | 11 |
| | Nucleotide sequence encoding the variable region of the heavy chain | 12 |
| | Amino acid sequence encoding the variable region of the light chain | 9 |
| | Nucleotide sequence encoding the variable region of the light chain | 10 |
| 215 | Amino acid sequence encoding the variable region of the heavy chain | 15 |
| | Nucleotide sequence encoding the variable region of the heavy chain | 16 |
| | Amino acid sequence encoding the variable region of the light chain | 13 |
| | Nucleotide sequence encoding the variable region of the light chain | 14 |
| 469 | Amino acid sequence encoding the variable region of the heavy chain | 19 |
| | Nucleotide sequence encoding the variable region of the heavy chain | 20 |
| | Amino acid sequence encoding the variable region of the light chain | 17 |
| | Nucleotide sequence encoding the variable region of the light chain | 18 |
| 809 | Amino acid sequence encoding the variable region of the heavy chain | 23 |
| | Nucleotide sequence encoding the variable region of the heavy chain | 24 |
| | Amino acid sequence encoding the variable region of the light chain | 21 |
| | Nucleotide sequence encoding the variable region of the light chain | 22 |
| 837 | Amino acid sequence encoding the variable region of the heavy chain | 27 |
| | Nucleotide sequence encoding the variable region of the heavy chain | 28 |
| | Amino acid sequence encoding the variable region of the light chain | 25 |
| | Nucleotide sequence encoding the variable region of the light chain | 26 |
| 861 | Amino acid sequence encoding the variable region of the heavy chain | 31 |
| | Nucleotide sequence encoding the variable region of the heavy chain | 32 |
| | Amino acid sequence encoding the variable region of the light chain | 29 |
| | Nucleotide sequence encoding the variable region of the light chain | 30 |
| 928 | Amino acid sequence encoding the variable region of the heavy chain | 35 |
| | Nucleotide sequence encoding the variable region of the heavy chain | 36 |
| | Amino acid sequence encoding the variable region of the light chain | 33 |
| | Nucleotide sequence encoding the variable region of the light chain | 34 |
| 1064 | Amino acid sequence encoding the variable region of the heavy chain | 35 |
| | Nucleotide sequence encoding the variable region of the heavy chain | 40 |
| | Amino acid sequence encoding the variable region of the light chain | 37 |
| | Nucleotide sequence encoding the variable region of the light chain | 38 |
| 1080 | Amino acid sequence encoding the variable region of the heavy chain | 43 |
| | Nucleotide sequence encoding the variable region of the heavy chain | 44 |
| | Amino acid sequence encoding the variable region of the light chain | 41 |
| | Nucleotide sequence encoding the variable region of the light chain | 42 |
| 1093 | Amino acid sequence encoding the variable region of the heavy chain | 47 |
| | Nucleotide sequence encoding the variable region of the heavy chain | 48 |
| | Amino acid sequence encoding the variable region of the light chain | 45 |
| | Nucleotide sequence encoding the variable region of the light chain | 46 |

The above light and heavy chain sequences are combined as indicated above in the antibodies with the mAb identification numbers indicated in the table. For example, SEQ ID NO: 35 and SEQ ID NO: 33 together comprise the heavy and light chain variable regions for antibody #928. In other embodiments, however, the light and heavy chains may be mixed or combined differently to generate antibodies with different properties.

Variants, including variants that are substantially homologous to the above antibodies are also contemplated. In some embodiments, antibody variants differ in their germline sequence from the disclosed antibodies. One way of identifying such variants is by aligning the various antibody sequences as shown in FIG. 4A and FIG. 4B. In that Figure, the various germline sequences are compared to the presently identified sequences. In one embodiment, an antibody variant has at least one mutation in the germline that makes the antibody more similar to one of the other presently disclosed antibodies. For example, an "I" at position 34 of SEQ ID NO: 50 will result in a variant of SEQ ID NO: 50 that will now be more similar to SEQ ID NO: 11.

Alterations of the non-germline antibodies to create variants is also contemplated. Thus, variants that are 50-60, 60-70, 70-80, 80-90, 90-95, 95-99, and 99-100% identical to the disclosed non-germline antibodies are also contemplated. Preferably, variant antibodies have high affinity for IL-8, and some degree of selectivity. Thus, alterations to the above non-germline sequences which either enhance the affinity or do not significantly reduce the affinity are contemplated.

Antibody Therapeutics

It is expected that the antibodies described herein will have therapeutic effect in treatment of symptoms and conditions resulting from the activity of IL-8. In specific embodiments, the antibodies and methods herein relate to the treatment of bacterial pneumonia, asthma, ulcerative colitis, COPD, chronic bronchitis, emphysema, bronchiectasis, immunoglobulin deficiency, psoriasis or cystic fibrosis.

Anti-IL-8 will have therapeutic effects in treating symptoms and conditions resulting from IL-8 activity. In addition, the high affinity antibodies can be used to identify diseases or disorders associated with changes in the levels of IL-8 in the body.

In preferred embodiments one or more high-affinity anti-IL-8 antibodies are used to treat an inflammatory disease. In specific embodiments, the antibodies and methods herein are used in the treatment of one or more diseases or disorders selected from the group consisting of acute inflammation, ARDS, glomerlonephritis, alcoholic hepatitis, psoriasis, reperfusion injury, rheumatoid arthritis, inflammatory bowel disease, bacterial pneumonia, asthma, ulcerative colitis, COPD, chronic bronchitis, emphysema, bronchiectasis, immunoglobulin deficiency or cystic fibrosis. In other embodiments the antibodies are used to treat cancer, such as a cancer selected from the group consisting of malignant melanoma, head and neck cancer, breast cancer, non-small cell lung cancer, ovarian cancer and brain cancer.

Therapeutic Administration and Formulations

Antibodies that bind IL-8 with high-affinity can be used therapeutically to treat a disease or disorder by reducing the activity of IL-8. Anti-IL-8 antibodies preferably possess adequate affinity to suppress IL-8 activity enough to have a therapeutic effect at the desired dosage. Preferably, antibodies for therapeutic use are in a sterile pharmaceutical preparation, as discussed in more detail below.

When used for in vivo administration, the antibody formulation is preferably sterile. This is readily accomplished, for example, by filtration through sterile filtration membranes, prior to or following optional lyophilization and reconstitution. The antibody ordinarily will be stored in lyophilized form or in solution. Therapeutic antibody compositions generally are placed into a container having a sterile access port, for example, an intravenous solution bag or vial having an adapter that allows retrieval of the formulation, such as a stopper pierceable by a hypodermic injection needle.

Antibodies, as described herein, can be prepared in a mixture with a pharmaceutically acceptable carrier. This therapeutic composition can be administered intravenously as a liquid or powder aerosol (lyophilized). The composition can also be administered parenterally or subcutaneously as desired. When administered systemically, the therapeutic composition should be sterile, pyrogen-free and in a parenterally acceptable solution having due regard for pH, isotonicity, and stability. These conditions are known to those skilled in the art. Briefly, dosage formulations of the compounds described herein are prepared for storage or administration by mixing the compound having the desired degree of purity with physiologically acceptable carriers, excipients, or stabilizers. Such materials are non-toxic to the recipients at the dosages and concentrations employed, and include buffers such as TRIS HCl, phosphate, citrate, acetate and other organic acid salts; antioxidants such as ascorbic acid; low molecular weight (less than about ten residues) peptides such as polyarginine, proteins, such as serum albumin, gelatin, or immunoglobulins; hydrophilic polymers such as polyvinylpyrrolidinone; amino acids such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium and/or nonionic surfactants such as TWEEN, PLURONICS or polyethyleneglycol.

Sterile compositions for injection can be formulated according to conventional pharmaceutical practice as described in *Remington: The Science and Practice of Pharmacy* (20$^{th}$ ed, Lippincott Williams & Wilkens Publishers (2003)). For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants and the like can be incorporated according to accepted pharmaceutical practice.

The antibodies can also be administered in and released over time from sustained-release preparations. Suitable examples of sustained-release preparations include semipermeable matrices of solid hydrophobic polymers containing the antibody, which matrices are in the form of shaped articles, films or microcapsules. Examples of sustained-release matrices include polyesters, hydrogels (e.g., poly(2-hydroxyethyl-methacrylate), for example, as described by Langer et al., *J. Biomed Mater. Res.*, (1981) 15:167-277 and Langer, *Chem. Tech.*, (1982) 12:98-105, or poly(vinylalcohol)), polylactides (U.S. Pat. No. 3,773,919, EP 58,481), copolymers of L-glutamic acid and gamma ethyl-L-glutamate (Sidman et al., *Biopolymers*, (1983) 22:547-556), non-degradable ethylene-vinyl acetate (Langer et al., supra), degradable lactic acid-glycolic acid copolymers such as the LUPRON Depot™ (injectable microspheres composed of lactic acid-glycolic acid copolymer and leuprolide acetate), and poly-D-(−)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through disulfide interchange, stabilization can be achieved by modifying sulfhydryl residues, lyophilizing from acidic solutions, controlling moisture content, using appropriate additives, and developing specific polymer matrix compositions.

Sustained-released compositions also include preparations of crystals of the antibody suspended in suitable formulations capable of maintaining crystals in suspension. These preparations when injected subcutaneously or intraperitonealy can produce a sustained release effect. Other compositions also include liposomally entrapped antibodies. Liposomes containing such antibodies are prepared by known methods, for example, as described in U.S. Pat. No. DE 3,218,121; Epstein et al., *Proc. Natl. Acad. Sci. USA*, (1985) 82:3688-3692; Hwang et al., *Proc. Natl. Acad. Sci. USA*, (1980) 77:4030-4034; EP 52,322; EP 36,676; EP 88,046; EP 143,949; 142,641; Japanese patent application 83-118008; U.S. Pat. Nos. 4,485,045 and 4,544,545; and EP 102,324.

The route of antibody administration can be, for example and without limitation, by injection or infusion by intravenous, intraperitoneal, intracerebral, intramuscular, intraocular, intraarterial, intrathecal, inhalation or intralesional routes, or by sustained release systems as noted below. The antibody is preferably administered continuously by infusion or by bolus injection.

The dosage of the antibody formulation for a given patient can be determined by the attending physician talking into consideration various factors known to modify the action of drugs including severity and type of disease, body weight, sex, diet, time and route of administration, other medications and other relevant clinical factors. Therapeutically effective dosages can be determined by either in vitro or in vivo methods.

An effective amount of the antibodies, described herein, to be employed therapeutically can depend, for example, upon the therapeutic objectives, the route of administration, and the condition of the patient. Accordingly, it is preferred for the therapist to titer the dosage and modify the route of administration as required to obtain the optimal therapeutic effect. A typical daily dosage might range from about 0.001 mg/kg to up to 100 mg/kg or more, more preferably from about 1 mg/kg to about 10 mg/kg, depending on the particular circumstances, including, for example, the factors mentioned above. Typically, the clinician will administer the therapeutic antibody until a dosage is reached that achieves the desired effect. The progress of this therapy is easily monitored by conventional assays or as described herein. The antibodies may be administered in a single dosage. Preferably, however, the antibodies are administered one or more times daily over an extended period of time. The dosage regimen may include a booster administration at a certain time after the last regular dose.

Therapeutic antibodies are preferably administered with suitable carriers, excipients, and other agents that are incorporated into formulations to provide improved transfer, delivery, tolerance, and the like. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures can be appropriate in treatments and therapies in accordance with some of the embodiments, provided that the active ingredient in the formulation is not inactivated by the formulation and the formulation is physiologically compatible and tolerable with the route of administration. See also Baldrick P. "Pharmaceutical excipient development: the need for preclinical guidance." *Regul. Toxicol. Pharmacol.* 32 (2):210-8 (2000), Wang W. "Lyophilization and development of solid protein pharmaceuticals." *Int. J. Pharm.* 203 (1-2):1-60 (2000), Charman W N "Lipids, lipophilic drugs, and oral drug delivery—some emerging concepts." *J Pharm Sci* 0.89 (8):967-78 (2000), Powell et al. "Compendium of excipients for parenteral formulations" *PDA J Pharm Sci Technol.* 52:238-311 (1998) and the citations therein for additional information related to formulations, excipients and carriers well known to pharmaceutical chemists.

Anti-IL-8 antibodies can be administered individually. In some embodiments, however, more than one antibody is preferably administered. The antibodies may be administered simultaneously or in sequence. For example, two or more high-affinity anti-IL-8 antibodies can be administered to a patient in a single formulation. In other embodiments the antibodies are administered together with another therapeutic. Other therapeutics include, without limitation, antibodies to a different target, chemotherapeutic agents and other compositions known to be beneficial in the treatment of the disease or disorder.

As mentioned above, at periodic times during treatment, patients are monitored to determine the efficacy of the treatment and to adjust the dosage if necessary. The methods of determining the efficacy of a particular dosing regimen will be known to the skilled practitioner. For example, the efficacy of high affinity anti-IL-8 antibodies in treating psoriasis can be measured by psoriasis area severity index (PASI), total body surface area (BSA), Physician's Global Assessment (PGA), and plaque photographs. PASI analysis is a widely accepted measure of drug response in psoriasis patients. Psoriatic patients treated with anti-IL-8 antibodies have an improved PASI score compared to psoriatic patients that are not treated with anti-IL-8 antibodies.

The efficacy of the use of the anti-IL-8 antibody as a treatment for rheumatoid arthritis can be measured by American College of Rheumatology 20% responder criteria (ACR20), also referred to as minimum improvement of 20% in the patient's rheumatoid arthritis. An ACR20 response requires a greater than 20% reduction in swollen joint count, a greater than 20% reduction in tender joint count and a greater than 20% improvement in three out of five of the following: patient's assessment of pain, patient's assessment of disease activity, investigator's assessment of disease activity, acute phase reactant (CRP) and patient's assessment of functional status (HAQ score). Patients with rheumatoid arthritis that are treated with anti-IL-8 antibodies have an ACR20 response while patients with rheumatoid arthritis that are not treated with anti-IL-8 antibodies do not experience an ACR20 response.

In the treatment of cancer with anti-IL-8 antibodies, efficacy can be measured by the level of tumor growth, angiogenesis and metastasis. Further, an increase in the number of cells undergoing apoptosis may be used as a measure of efficacy in tumor patients that are administered anti-IL-8 antibodies.

In a particular embodiment, a patient suffering from COPD is identified. A dosage of about 5 mg/kg of a high-affinity anti-IL-8 antibody is administered by intravenous injection to the patient. A booster administration is given three weeks later, and every three weeks thereafter. The antibody causes a partial or complete inhibition of neutrophil chemotaxis in the inflamed respiratory tissues. This inhibition of neutrophil chemotaxis reduces the severity of tissue damage to the lungs and air passages. Additional descriptions and guidance regarding methods of treating an IL-8 related disorder (e.g., COPD) can be found in U.S. Pub. No. 20030232048, filed Mar. 18, 2003, to Yang et al. (incorporated by reference in its entirety). Additional information and guidance can be found regarding the treatment of bacterial pneumonia (U.S. Pat. No. 5,686,070), asthma (U.S. Pat. No. 5,874,080), and ulcerative colitis (U.S. Pat. No. 5,707,622), all incorporated by reference in their entireties.

As will be appreciated by one of skill in the art, the formulations can be used in the preparations of medicaments for the treatment of the relevant IL-8 related or dependent disorders.

IL-8 Diagnostics

High affinity antibodies to IL-8 can be used in assays for the detection of IL-8 in mammalian tissues, fluids or cells. The assays may be used, for example, to screen patients for a disease or disorder associated with changes in levels of IL-8, such as bacterial pneumonia, asthma, ulcerative colitis, COPD, chronic bronchitis, emphysema, bronchiectasis, immunoglobulin deficiency, and cystic fibrosis. An assay system preferably comprises a package containing, in an amount sufficient to perform at least one assay, a composition containing a high-affinity anti-IL-8 antibody. This antibody composition can be, for example, in liquid solution or attached to a solid-phase matrix. The system also preferably includes a detectable label for indicating the presence of antibody molecules in any immunoreaction products formed upon contacting a sample from a patient with the antibody composition. The levels of IL-8 identified in a sample can be compared to a control sample to determine if elevated IL-8 levels are present.

Identification of Epitopes Bound by Anti-IL-8 Antibodies

The following discussion describes several exemplary methods for identifying and characterizing the epitope on IL-8 bound by particular antibodies. Other methods that can be used will be apparent to those of skill in the art.

IL-8 can be subjected to SDS-PAGE and analyzed by immunoblotting with the desired anti-IL-8 antibody. The SDS-PAGE can be performed either in the absence or presence of a reducing agent. Accordingly, it is possible to determine whether antibodies against IL-8 bind to a linear epitope on IL-8 or a conformational epitope.

Epitope mapping can also be performed using surface-enhanced laser desorption/ionization (SELDI). SELDI ProteinChip® arrays (Ciphergen Biosystems, Fremont, Calif.) are used to define sites of protein-protein interaction. Briefly, antigens are specifically captured on antibodies covalently immobilized onto the Protein Chip array surface by an initial incubation and wash. The bound antigens can be detected by a laser-induced desorption process and analyzed directly to determine their mass. Fragments of the antigen that bind are used to identify the epitope bound by the antibody.

The epitope bound by an anti-IL-8 antibody can also be determined by phage display. Phage display describes a selection technique in which a peptide is expressed as a fusion with a coat protein of a bacteriophage, resulting in display of the fused protein on the surface of the virion. Panning is carried out by incubation of a library of phage displayed peptide with a plate or tube coated with the target, washing away the unbound phage, and eluting the specifically bound phage. The eluted phage is then amplified and taken through additional binding and amplification cycles to enrich the pool in favor of binding sequences. After three or four rounds, individual clones binding are further tested for binding by phage ELISA assays performed on antibody-coated wells and characterized by specific DNA sequencing of positive clones.

After multiple rounds of such panning against an antibody the bound phage can be eluted and subjected to further studies for the identification and characterization of the bound peptide.

In some instances it may be desirable to generate additional antibodies that bind to a particular epitope of IL-8. For example, if an antibody has particularly desirable attributes, additional antibodies made to that epitope may maintain those features but have other features, such as a higher affinity. The antigen used to generate such antibodies would comprise the desired epitope. In some embodiments the antigen may consist of a peptide with the sequence of the desired epitope. In other embodiments, the antigen may be a peptide that comprises the epitope sequence, such as a fusion protein.

Human antibodies to particular epitopes are generated using Xenomouse technology, as described herein, or using other known methods for generating fully human monoclonal antibodies. While human antibodies are preferred for therapeutic applications, in other situations the use of human antibodies is not necessary. Thus, in some embodiments, monoclonal antibodies can be generated using other methods, such as the hybridoma method first described by Kohler et al., *Nature* 256: 495 (1975), or can be made by recombinant DNA methods as described in U.S. Pat. No. 4,816,567, which is incorporated by reference in its entirety.

In the hybridoma method, a mouse or other appropriate host animal, such as a hamster or macaque monkey, is immunized as herein above described to elicit lymphocytes that produce or are capable of producing antibodies that will specifically bind to the protein used for immunization. Alternatively, lymphocytes can be immunized in vitro. Lymphocytes or more preferably, lymphocytes enriched for B cells then are fused with myeloma cells by an electrocell fusion process or by using a suitable fusing agent, such as polyethylene glycol, to form a hybridoma cell (Goding, *Monoclonal Antibodies: Principles and Practice*, pp. 59-103, [Academic Press, 1996]).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOP-21 and MC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.* 133: 3001 (1984); Brodeur et al., *Monoclonal Antibody Production Techniques and Applications*, pp. 51-63, Marcel Dekker, Inc., New York, [1987]).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis of Munson et al., *Anal. Biochem.* 107: 220 (1980).

After hybridoma cells are identified that produce antibodies of the desired specificity, affinity, and/or activity, the cells can be subcloned by limiting dilution procedures and grown by standard methods (Goding, *Monoclonal Antibodies: Principles and Practice*, pp. 59-103, Academic Press, 1996). Suitable culture media for this purpose include, for example, DMEM or RPMI-1640 medium. In addition, the hybridoma cells can be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA can be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by covalently joining to the immunoglobulin coding sequence all or part of the coding sequence for a non-immunoglobulin polypeptide. In that manner, "chimeric" or "hybrid" antibodies are prepared that have the binding specificity of an anti-IL-8 monoclonal antibody herein.

Typically such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for IL-8 and another antigen-combining site having specificity for a different antigen.

Chimeric or hybrid antibodies also can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

To confirm that antibodies immunoreact specifically with the desired epitope, the ability of the antibodies to bind IL-8 with a mutation in the epitope can be tested. A mutation in the epitope would be expected to result in the inability of the antibody against the epitope to bind to IL-8. Such binding of an antibody to IL-8 can be detected by subjecting the mutant IL-8 to SDS-PAGE gel electrophoresis followed by immunoblot analysis.

EXAMPLES

The following examples, including the experiments conducted and results achieved, are provided for illustrative purposes only and are not to be construed as limiting.

Except as otherwise indicated protocols were carried out conventionally and commercially available reagents were used according to the manufacturers instructions.

Example 1

Antibody Generation

Immunization

Human monoclonal antibodies against human IL-8 were developed by sequentially immunizing XENOMOUSE® mice (XenoMouse® XMG2, Abgenix, Inc. Fremont, Calif.).

Cohorts of XMG2 XENOMOUSE® mice were immunized with recombinant human Interleukin-8 (rhIL-8). The initial BIP (base of the tail by subcutaneous injection and intraperitoneum) immunization was with 50 ug of rhIL-8 mixed 1:1 v/v with Complete Freund's Adjuvant (CFA) per mouse. Subsequent boosts were made with 50 ug of rhIL-8 mixed 1:1 v/v with Incomplete Freund's Adjuvant (IFA) per mouse. The animals were immunized on days 0, 14, 28, and day 42. Then immunizations were continued for some mice with 50 ug of rhIL-8 in Titermax gold adjuvant ip (on days 146, 160, and day 181) and then with 10 ug of rhIL-8 in PBS ip on day 205. A final boost was done with 10 ug of rhIL-8 in PBS ip on day 226 (for two mice) and on day 234 (for two mice). Serum was collected just before the final boost and anti-hIL8 titer was determined by ELISA.

Selection of Animals for Harvest

Anti-IL-8 antibody titers were determined by ELISA. For ELISA, biotinylated human IL-8 was bound to streptavidin plates at 0.25 ug/mL for 1 hour at room temperature on 96-well plates. Each plate was washed 5 times with dH2O, before 90 µL of 1% milk in PBS with 0.05% sodium azide were added to the plate. XENOMOUSE® sera from either the IL-8 immunized animals, or naïve XENOMOUSE® animals was titrated in 1% milk/PBS at 1:2 dilution in duplicate from a 1:100 initial dilution. The last well was left blank. After 1 hour at room temperature the plates were again washed 5 times with dH2O. A goat anti-human IgG Fc-specific horseradish peroxidase (HRP, Pierce, Rockford, Ill.) conjugated antibody was added at a final concentration of 1 µg/mL for 1 hour at room temperature. The plates were washed five times with dH2O. The plates were developed with the addition of TMB chromogenic substrate (Gaithersburg, Md.) for 30 minutes and the ELISA was stopped by the addition of 1 M phosphoric acid. The specific antibody titers of individual XENOMOUSE® animals was determined from the optical density at 450 nm and ranged between 1:32,000 and 1:256,000. The titer represents the reciprocal dilution of the serum and therefore the higher the number the greater the humoral immune response to IL-8.

XENOMOUSE® animals with high anti-IL-8 titers were selected for harvest and the generation of monoclonal antibodies

Example 2

Anti-Human IL-8 Antibodies

Culture and Selection of B Cells

B-cells from the animals were harvested and cultured in plates. Wells were screened by ELISA as described above to identify B-cells producing IL-8-specific antibodies, 1063 wells were identified as being positive for IL-8 binding.

Limited Antigen Assay

The IL-8-specific antibodies were then affinity ranked by limited antigen analysis as described before (See, e.g., PCT Publication WO/03048730A2 entitled "IDENTIFICATION OF HIGH AFFINITY MOLECULES BY LIMITED DILUTION SCREENING" published on Jun. 12, 2003).

Isolation of IL-8-Specific B cells by Hemolytic Plaque Assay

Single B cells secreting antibodies of interest were then isolated using a rhIL8-specific hemolytic plaque assay (Babcook et al., *Proc. Natl. Acad. Sci. USA*, 93:7843-7848, 1996), using sheep red blood cells (SRBCs) coated with the rhIL-8 antigen. B cells secreting the immunoglobulin of interest are identified by specific anti-rhIL8-mediated lysis of the SRBCs in the presence of complement. The single hIL8-specific plasma cell in the center of the plaque was isolated by micromanipulation.

Expression of Recombinant Anti-IL-8 Antibodies

After isolation of the single plasma cells, mRNA was extracted and reverse transcriptase PCR was conducted to generate cDNA encoding the variable heavy and light chains. The human variable heavy chain region was cloned into an IgG2 expression vector. This vector was generated by cloning the constant domain of human IgG2 into the multiple cloning site of pcDNA3.1+/Hygro (Invitrogen, Burlington, ON). The human variable light chain region was cloned into an IgK expression vector. These vectors were generated by cloning the constant domain of human IgK into the multiple cloning site of pcDNA3.1+/Neo (Invitrogen, Burlington, ON). The heavy chain and the light chain expression vectors were then co-lipofected into a 60 mm dish of 70% confluent human embryonal kidney 293 cells and the transfected cells were allowed to secrete a recombinant antibody with the identical specificity as the original plasma cell for 24-72 hours. The supernatant was harvested from the HEK 293 cells and the secretion of an intact antibody was demonstrated with a sandwich ELISA to specifically detect human IgG. Specificity was assessed through binding of the recombinant antibody to rhIL-8 using ELISA as described above.

Purification of Recombinant Anti-IL-8 Antibodies

For larger scale production, heavy and light chain expression vectors (2.5 µg of each chain/dish) were lipofected into ten 100 mm dishes that were 70% confluent with HEK 293 cells. The transfected cells were incubated at 37° C. for 4 days, the supernatant (6 mL) was harvested and replaced with 6 mL of fresh media. At day 7, the supernatant was removed and pooled with the initial harvest (120 mL total from 10 plates). Each antibody was purified from the supernatant using a Protein-A Sepharose (Amersham Biosciences, Piscataway, N.J.) affinity chromatography (1 mL). The antibody was eluted from the Protein-A column with 500 mcL of 0.1 M Glycine pH 2.5. The eluate was dialysed in PBS pH 7.4 and filter sterilized. The antibody was analyzed by non-reducing SDS-PAGE to assess purity and yield. Concentration was also measured by UV analysis at OD 280 and ELISA.

Example 3

Kinetic Analysis

Kinetic measurements of the anti-IL-8 antibodies were performed using the KinExA® method. This method provides a solution-based determination of formal affinity at equilibrium.

Preparation of Antigen Coated Beads

Fifty µg of rhIL-8 was coupled to CNBr-activated Sepharose 4B. Alternatively, 25 µg/ml or 100 µg/ml of rhIL-8 was coupled to NHS-activated Sepharose. The remaining active groups on the beads were blocked as recommended by the manufacturer. The beads were then finally blocked with 10 mg/ml BSA in 1 M Tris and stored in the blocking solution.

KinExA Equilibrium Assays

The experiments with KinExA were performed using an automated flow immunoassay system, KinExA 3000 [Ohmura et al., Anal. Chem. 73:3392, 2001] in which rhIL-8-coupled beads served as the solid phase. A constant amount of antibody between 0.67 and 5000 pM active binding site concentration was incubated with titrating concentrations of rhIL-8 antigen starting at 100 nM in sample buffer (PBS with 0.1% BSA) to reduce nonspecific binding. Antigen/antibody complexes were incubated at RT for 36 h to 144 h to allow equilibrium to be reached. The mixture was drawn through the rhIL-8-coupled beads to accumulate unbound antibody. The captured anti-hIL-8 mAb is directly proportional to the remaining free binding sites and was detected using solutions containing Cy5-conjugated anti-human secondary antibody in sample buffer. The concentrations, volumes, and flow rates of the secondary antibody solutions were varied to optimize the signal to noise ratio in each experiment. The bound signals were converted into relative values as a proportion of control in the absence of rhIL-8. The equilibrium dissociation constant ($K_d$) was obtained from nonlinear regression analysis of the data using a one-site homogeneous binding model contained within the software [Blake et Al., Anal. Biochem. 272:123, 1999; Jones et al., Bioconjug Chem 13:408, 2002]. The software calculates the $K_d$ and determines the 95% confidence interval by fitting the data points to a theoretical $K_d$ curve. The 95% confidence interval is given as $K_d$ low and $K_d$ high.

To determine the $K_d$ data in Table 3, serial dilutions of rhIL-8 were mixed with the respective anti-hIL-8 mAbs and allowed to reach equilibrium for 36 hrs. A proportionate amount of free mAb present in the equilibrium mixture was measured by flowing 0.25 ml to 3 ml of the sample on rhIL-8 coupled to CNBr-activated Sepharose beads and detected using 1.0 ml of 1.7 µg/ml of Cy5-labeled goat anti-human IgG Fcγ fragment-specific secondary antibody. Each sample was run in triplicate. The $K_d$ was calculated by the KinExA software and the 95% confidence interval is given as the $K_d$ range.

TABLE 3

| Anti-hIL-8 mAb | $K_d$ (pM) | $K_d$ (pM) Range | mAb conc. (pM) |
|---|---|---|---|
| 33 | 280 | 150-420 | 10 |
| 142 | 400 | 190-680 | 25 |
| 203 | 190 | 64-340 | 25 |
| 215 | 360 | 230-450 | 50 |
| 469 | 870 | 640-1010 | 200 |
| 809 | 2.2 | 0.36-4.8 | 23 |
| 837 | 11 | 0.054-31 | 90 |
| 861 | 2.9 | 0.010-8.2 | 25 |
| 928 | 0.057 | <0.010-1.8 | 20 |
| 1064 | 54 | 29-72 | 50 |
| 1080 | 630 | 160-980 | 25 |
| 1093 | 200 | 76-300 | 100 |

Signal Determination

In order to make an accurate $K_d$ measurement by KinExA, the active antibody binding site concentration should be near or below the actual $K_d$. To measure antibodies with very high affinities (very low $K_d$s), it is necessary to work at low picomolar antibody binding site concentrations. At these low antibody concentrations the sensitivity of the assay needs to be further optimized. To increase the detection sensitivity of free antibodies, bead coating concentrations, sampling parameters, as well as different labels, were examined.

Adjustment of Bead Coating and Labeled Secondary Antibody

Immobilization of certain antigens to beads can alter their ability to bind antibodies due to steric hindrance by passive coating or destruction of epitopes by side chain reactive coupling. To increase the signal in the bead pack, IL-8 was coupled to NHS-Sepharose beads and tested bead saturation, as described (Ohmura et al., *Anal. Chem.*, 73:3392-9, (2001)). It was determined that there was no signal gain above a coupling concentration of 100 μg/ml of antigen. At 25 μg/ml of antigen, approximately 70% of the maximum signal was observed. The beads were coupled with 100 μg/ml of rhIL-8 for the low antibody concentration ($K_d$ controlled) experiments. NHS-Sepharose beads were coupled with 25 μg/ml of rhIL-8 for the high concentration of mAb experiments and kinetic experiments to conserve antigen.

Different Cy5-labeled anti-human secondary antibodies were checked to identify one that would give the highest signal to noise ratio. A 100 pM solution of anti-hIL-8 mAb with various secondary labels (goat anti-human IgG (H+L)-specific, Fcγ fragment-specific or mouse anti-human Fab-specific) was examined. The highest signal to noise ratio was generated using the Fcγ-specific label (9.9 times higher than background). This Fcγ fragment-specific goat anti-human secondary antibody was used for subsequent equilibrium and kinetic measurements.

Determination of Sample Volume and Flow Rate

Since the initial equilibrium analysis of a few anti-hIL-8 mAbs showed low picomolar to sub-picomolar $K_d$s with broader 95% confidence intervals (Table 3; mAb 809, 837, 861, 928), the sample volume and flow rates were then manipulated. 100 pM of anti-hIL-8 mAb 928 was signal tested either flowing 0.5 ml at 0.25 ml/min or 3.0 ml at 1.5 ml/min for 120 sec. It was determined that increasing the sample volume and flow rate gave about 20% higher signal. The concentration of anti-hIL-8 mAb 928 was then lowered to 2 pM and a signal test was performed by flowing 30 ml at 1.5 ml/min for 1200 sec. A good signal was obtained.

Time to Reach Equilibrium and Sample Viability

The antibody binding site concentration was lowered to 1 pM, to measure the $K_d$ of low to sub-picomolar mAbs. At this very low concentration of antibody, the samples require a longer period of time to reach equilibrium. Using the $K_d$ curve obtained at a low mAb concentration and the measured $k_{on}$ from the kinetic experiment, it was estimated that the minimum time needed to reach equilibrium would be six days, using the kinetic theory curve software from Sapidyne Instruments Inc. Otherwise, one could experimentally determine whether the antigen-antibody mixture reached equilibrium by measuring the free mAb left in solution, which should remain constant during triplicate measurements, if equilibrium has been achieved. The viability of 1 pM anti-hIL-8 mAb 928 at 0, 3 and 6 day incubation times was then checked and it was found that the antibody activity had not decreased during this period at room temperature. Subsequently, all equilibrium reactions were allowed to take place for 6 days.

Equilibrium Measurements of mAbs Having Low Picomolar Affinity

The $K_d$ measurements were repeated using KinExA for the mAbs which had $K_d$s below 20 pM and broad 95% confidence intervals with improved parameters for bead coupling, sample volume, flow rate and secondary antibody-label. To determine the $K_d$ data in Table 4, serial dilutions of rhIL-8 were mixed with the respective anti-hIL-8 mAbs in the binding site concentrations shown in Table 4 and allowed to reach equilibrium for 36 hrs for the high binding site concentration of each mAb, or for 144 hrs for the low binding site concentration of each mAb. A proportionate amount of free mAb present in the equilibrium mixture was measured in KinExA under optimized conditions. For example, for the mixtures containing the low concentration of mAb, 18-36 ml of the sample was flown through rhIL-8 coupled to NHS-activated Sepharose beads and detected using 1-2 ml of 2.0 μg/ml of Cy5-labeled goat anti-human IgG Fcγ fragment-specific secondary antibody. The $K_d$ was calculated using KinExA software by using the "n-curve analysis" selection. This "n-curve analysis" selection allows one to obtain a precise $K_d$ value (Table 4) by fitting all of the given curves to a single $K_d$ value simultaneously and the 95% confidence interval is given as the $K_d$ range. The n-curve analysis produced a precise $K_d$ value.

TABLE 4

| Anti-hIL-8 mAb | $K_d$ (pM) | $K_d$ (pM) Range | mAb conc. (pM) |
|---|---|---|---|
| 809 | 3.29 | 1.9-5.2 | 4.6, 27 |
| 837 | 15.7 | 9.3-24.6 | 18, 120 |
| 861 | 3 | 2-4.2 | 1.3, 13 |
| 928 | 0.613 | 0.38-0.93 | 0.68, 2.0, 13.7 |

A number of experiments were performed for n-curve analysis of mAb 928. In these experiments mAb 928 was used either near the $K_d$ concentration, or at a concentration of about 15-20 fold higher than the $K_d$. By n-curve analysis, the $K_d$ of mAb 928 was determined to be 613 fM ($K_d$ high=935 fM and $K_d$ low=380 fM), which is very close to the $K_d$ determined by low mAb concentration experiments analyzed in single curves (590±220 fM). The $K_d$ distribution of individual measurements of mAb 928 are given in FIG. 3.

KinExA Kinetic Assays

For measuring the association rate constant using KinExA, the same rhIL-8-coupled beads were used as the probe and the "Kinetics, Direct" method was used. The "Kinetics, Direct" experiments by KinExA are identical to KinExA equilibrium assays with respect to bead column height, antibody capture, antibody concentration and antibody detection. Briefly, the mAb was mixed with an amount of antigen that bound approximately 80% of the mAb in the equilibrium experiments and the free antibody present in the sample was probed repeatedly, pre-equilibrium. Since the binding signals are proportional to the concentration of free antibody in the solution, the signals decrease over time until the solution has equilibrated. The volumes and flow rates of the antigen-mAb mixtures and the Cy5-labeled secondary antibody were varied depending upon the mAb tested. Data was analyzed utilizing the KinExA analysis software that comes with the KinExA 3000 instrument. This software graphically represents the decrease in binding signals over time, and fits the collected data points to an exact solution of the kinetic differential equations for binding. From this curve, an optimal solution for the $k_{on}$ is determined. The $k_{off}$ is indirectly calculated from solutions for the $k_{on}$ and $K_d$.

On-Rate Measurements of High Affinity mAbs

The on-rate measurement by KinExA is not limited by the mAb concentration used in the experiment. Therefore, the measurements of $k_{on}$ for the very high affinity antibodies did not require further optimizations. The measured $k_{on}$ and the calculated $k_{off}$ are given in Table 5. The concentration of mAb used for on-rate experiments was the same as those used in equilibrium binding experiments. An amount of IL-8 that bound 80% of the mAb in equilibrium binding experiments was mixed with the mAb. The amount of free mAb left in the mixture was measured in KinExA by flowing 1 ml of the mixture repeatedly through rhIL-8 coupled to NHS-activated Sepharose beads and detected using 1 ml of 2.0 μg/ml of Cy5-labeled goat anti-human IgG Fcγ fragment-specific secondary antibody. The $k_{on}$ was measured using the KinExA software by the "Kinetic, Direct" method and the 95% confidence intervals are given as $k_{on}$ range. The $k_{off}$ for the mAb was calculated from the measured $k_{on}$ and $K_d$ of the respective mAb.

TABLE 5

| Anti-hIL-8 mAb | $k_{on}$ (M$^{-1}$S$^{-1}$) | $k_{on}$ range (M$^{-1}$S$^{-1}$) | $k_{off}$(S$^{-1}$) |
|---|---|---|---|
| 809 | 4.8E+6 | 4.5E+6-5.5E+6 | 1.6E−5 |
| 837 | 1.1E+6 | 1.08E+6-1.17E+6 | 1.9E−5 |
| 861 | 4.4E+6 | 4.0E+6-5.0E+6 | 1.3E−5 |
| 928 | 6.0E+6 | 5.6E+6-6.4E+6 | 3.7E−6 |

Example 4

Structural Analysis of Antibodies

The variable heavy chains and the variable light chains for the antibodies shown in Table 3 above were sequenced to determine their DNA sequences. The complete sequence information for these anti-IL-8 antibodies are shown in the sequence listing submitted herewith, including nucleotide and amino acid sequences.

FIG. 4A is a comparison showing various XENOMAX® derived antibody heavy chain regions to a particular germ line heavy chain region. FIG. 4B is a comparison showing various XENOMAX® derived antibody light chain regions to a particular germ line light chain region.

Example 5

Identification of the Epitope Bound by ABX-IL-8

Phage Display

To determine the epitope bound by ABX-IL-8, a combinatorial library of random peptide 12-mers from the IL-8 protein was displayed on filamentous phage.

Panning was carried out in immunotubes (Nunc Cat. No. 470319). The ABX-IL-8 (10 μg/ml) antibody suspended in an ELISA coating buffer was used to coat the immunotubes with gentle agitation overnight at 4° C. The tubes were then blocked for 1 hour with TBS, 2% skim milk, and 2×10$^{12}$ phage (Ph.D.-12 Phage Display Peptide Library kit from New England Biolabs, Inc.) were panned in a total volume of 3 ml of TBS containing 2% skim milk and rocked gently for 1 hour at room temperature. Non-binding phage were removed with 20 washes containing TBS, 0.1% Tween-20. Phage bound to ABX-IL-8 antibody coated immunotubes were eluted with 1 ml 0.1M glycine-HCL buffer (pH 2.2). Further, the eluate was neutralized with 150 ml 1M Tris-HCl (pH 9.1) and used to infect E. coli E 738 cells for further amplification of the phage. After three selection rounds of panning, specific binding of epitope-displaying phage clones to ABX-IL-8 antibodies was confirmed by a phage ELISA assay performed on the antibody-coated wells. Automated DNA sequencing was performed to identify the amino acid sequence of positive clones interacting with ABX-IL-8 antibody coated tubes. The sequences were then aligned to residues 15 to 21 of the IL-8 protein. The consensus amino acid sequence among these sequences that was identified was KPXPXF (SEQ ID NO. 63; FIG. 5). The dash in FIG. 5 does not denote a conserved sequence and merely denotes the absence of an amino acid.

Mass Spectrometry

In addition, mass spectrometry was performed on fragments of the IL-8 antigen that were able to bind to immobilized ABX-IL-8 antibodies.

For immobilization of ABX-IL-8 antibodies, 3 μg of the ABX-IL-8 antibody was spotted on a PS2 chip (Ciphergen Biosystems, Fremont, Calif.) and incubated overnight in a shaking humid chamber at 4° C. Residual active sites were then blocked with 1 M ethanolamine, pH 8.0. The chips were washed two times with PBS containing 0.5% Triton-X 100 for 5 minutes at room temperature. The washed chip was incubated with 0.1M Tris, pH 8.0 for 30 minutes. The chip was further incubated with 0.5M NaCl in PBS for 5 minutes and further with three washes containing PBS.

Preparation of IL-8 protein for mass spectrometry analysis included a number of steps to ensure optimal digestion of the protein by Glu-C. IL-8 protein was subjected to denaturation, reduction, and methylation which prevented the formation of disulfide bonds between cysteine residues in the protein. Accordingly, IL-8 protein was denatured by mixing 10 μg of IL-8 (1 μg/μl) with 8 M guanidine HCl and reduced by adding 20 mM DTT to the IL-8 mixture. For proper mixing of the reagents, the mixture was then shaken at 75 RPM for 30 minutes at 37° C. For methylation of IL-8, iodoacetic acid in 12.5% NaOH was added to the IL-8 mixture. The mixture was vortexed gently and incubated in the shaker at 75 RPM for 30 minutes at 37° C. in the dark. The reaction was quenched with 100 mM DTT and vortexed gently. To remove the denaturation, reduction and methylation reagents, the IL-8 mixture was dialyzed against 50 mM ammonium bicarbonate, pH 7.8 in minidialyzer MWCO 3500 for 3-4 hours. 5 μg of the denatured, reduced, and methylated IL-8 was digested with 500 ng Glu-C at a ratio of GluC to protein of 1:10. 10 μL of 0.1 μg/μl Glu-C was added to 5 μg of IL-8 protein in a final volume of 60 μl. The mixture was incubated overnight in a 25° C. waterbath with gently shaking at 50 RPM. The enzyme digestion reaction was stopped by incubating the mixture at 55° C. for 10 minutes.

The digested, methylated IL-8 was then spotted onto ABX-IL-8-immobilized PS2 chips. For the binding, 5 μl of methylated and digested IL-8 protein was spotted onto the chip and incubated in a shaking humid chamber for 3-4 hours at room temperature. The spots were not washed to get the entire peptide map, while some spots were washed with PBS containing 0.16% Triton-X100, followed by washes with HPLC washes in order to identify the sequence of the fragment that specifically bound to the ABX-IL-8 antibodies. Once immobilized on the chip, the IL-8 antigen was digested with Glu-C, an endoprotease that specifically cleaves peptide bonds on the carboxy-terminal side of glutamic acid (E) amino acid residues. The chip was washed with 3 washes with PBST to remove any unbound product. Further, bound IL-8 fragments were analyzed and identified by SELDI based on their molecular weight.

SELDI-Based Analysis of IL-8 Bound to Immobilized ABX-IL-8 Antibodies

After the IL-8 fragments were incubated with the ABX-IL-8 bound PS2 chips, spots were either not washed or washed with 0.16% Triton-X100 in PBS followed by HPLC water wash. Spots that were not washed were used for identifying the entire peptide map of the IL-8 fragments. Spots that were washed were used for identifying the IL-8 fragment or epitope that specifically interacted with the ABX-IL-8 antibodies. Further, 5 mg of energy absorbing molecule-1 (EAM-1) was dissolved in 0.25 ml of 50% CH3CN containing 0.5% TFA. A 1:25 dilution of the EAM-1 solution was made in 10% CH3CN containing 0.5% TFA, and 0.5 μL of the diluted EAM-1 solution was spotted onto the IL-8 spots and allowed to dry. The IL-8 peptide fragments were analyzed by mass spectrometry at 190 and 200 intensity.

Figure 6:
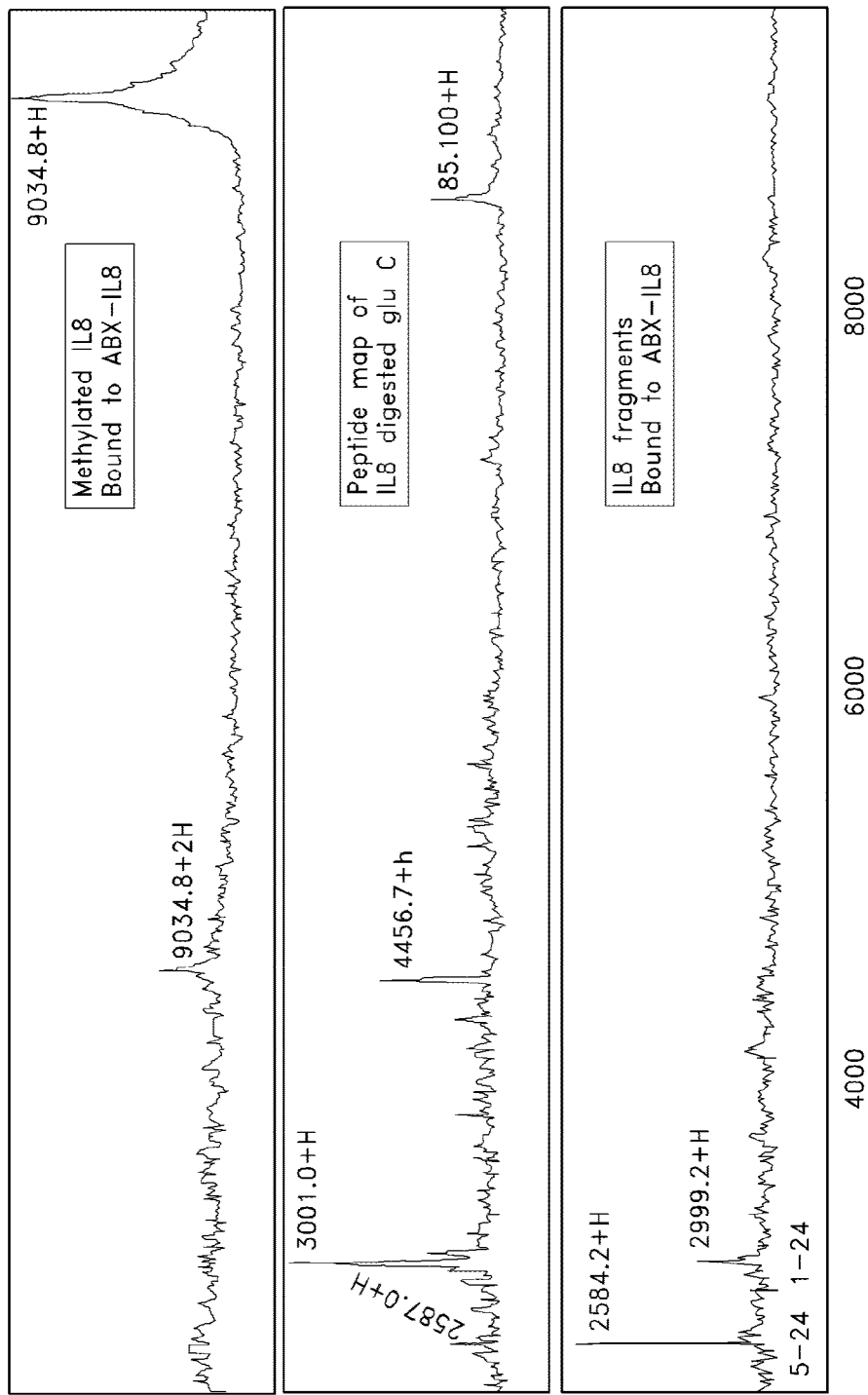
FIG. 6 shows mass spectrometry analysis of IL-8 fragments that specifically bind to ABXha-IL-8 antibodies, immobilized on PS2 chips.

A 20 amino acid sequence, located at residues 5 to 24 of the IL-8 protein, with a molecular mass of 2466.315 and the sequence "LRCQCIKTYSKPFHPKFIKE" (SEQ ID NO: 62) was identified as the fragment that most tightly bound to the ABX-IL-8 antibody. The mass spectrophotometry analysis of this fragment is shown in FIG. 6. Another related fragment KPFHPKFIKELR (SEQ ID NO: 84), which contains several amino acids in common with SEQ ID NO: 62 was also found to bind to the ABX-IL-8 antibody.

Site-Directed Mutagenesis of IL-8

To determine whether the specific amino acids of the IL-8 protein were necessary for interaction between IL-8 and the ABX-IL-8 antibody, IL-8 was mutated by site directed mutagenesis and further analyzed by immunoblotting for the ability to bind to the ABX-IL-8 antibody. For example, the proline at amino acid position 16 of IL-8 was found to be necessary for binding of ABX-IL-8 antibodies to IL-8.

A glutathione-S-transferase (GST) fusion containing IL-8 mutated at amino acid position 16 was generated. A GST fusion containing wild-type IL-8 was also generated and used as a positive control for binding studies. The fusions were each expressed in *E. coli*. The *E. Coli* cells expressing the GST fusions were lysed and the GST fusions were affinity purified with glutathione-Sepharose and further, subjected to SDS-PAGE and immunoblotting. The primary antibodies used for detecting of IL-8 were either anti-GST antibody or ABX-IL-8 antibody, and the secondary antibodies used were coupled to horseradish peroxidase.

Figure 7:
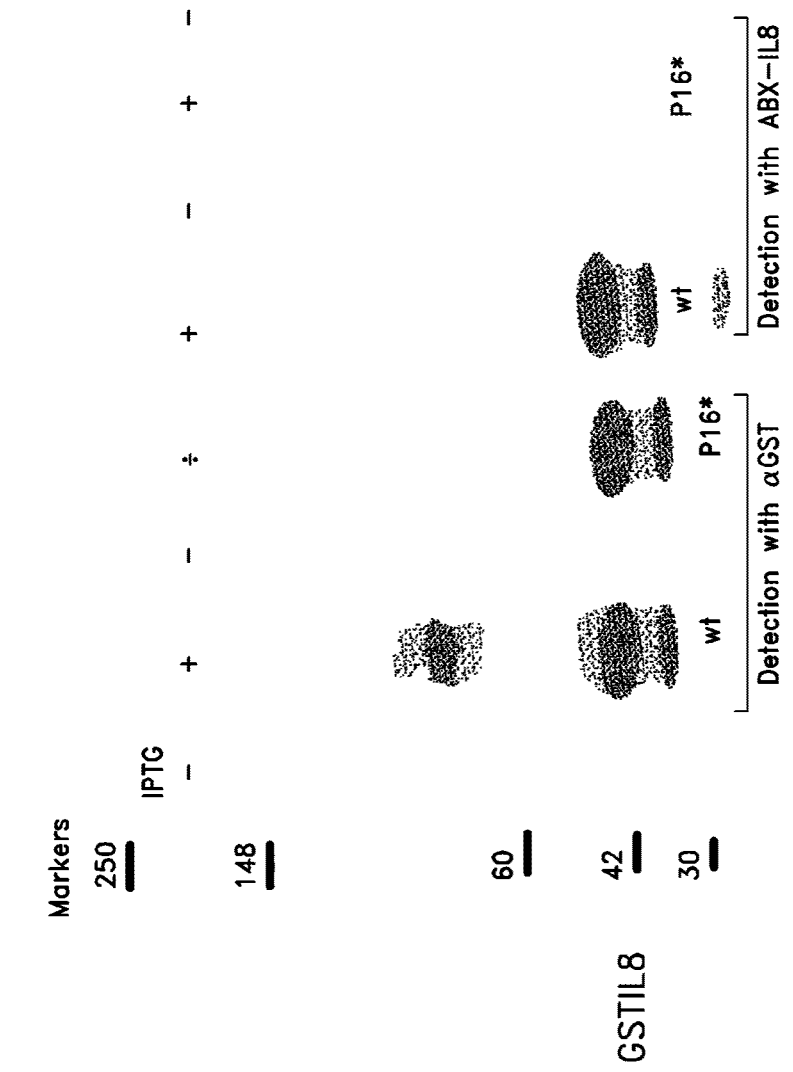
FIG. 7 shows a gel indicating a lack of binding of ABXha-IL-8 antibodies to IL-8 antigen having a mutation in the proline at amino acid position 16.

The results from the immunoblotting (FIG. 7) show that mutation of the proline at amino acid position 16 of IL-8 abolishes binding of ABX-IL-8 antibodies to IL-8. Detection with alpha-GST resulted in bands for both the wild-type and the proline mutant. However, detection with ABX-IL-8 resulted in bands only for the wild-type IL-8, and no band for the IL-8 proline mutant at position 16. The binding of GST antibodies to the GST-IL-8 fusions were not affected by the mutation of the proline. Accordingly, the epitope for the ABX-IL-8 antibody likely contains the proline at amino acid position 16 of IL-8.

Example 6

Identification of the Epitope Bound by Several ABXHA-IL-8 Antibodies

The epitope for several of the ABXha-IL-8 antibodies was also determined. The results are depicted in Table 6 below. Briefly, overlapping IL-8 peptides, which were each two amino acids c-terminal to the previous peptide (as shown in FIG. 8) were prepared and attached to a membrane. Antibodies were then added and allowed to bind to the peptides.

As can be seen from the results in Table 6, antibodies 809, 837, and 928 bound to a different epitope than the antibodies described in Example 5 (or the epitope that is contained within SEQ ID NO: 84). Thus, it appears that there are alternative epitopes and that the peptide sequence ELRCQCIK-TYSK (SEQ ID NO: 79) has an especially high affinity epitope(s).

In addition to determining that the ABX-IL-8 antibodies and the ABXha-IL-8 antibodies bind to relatively different peptides, and thus epitopes, whether or not the various antibodies compete with one another was also determined. It was determined that mAb 837 competes with K221, while mAbs 809 and 928 compete with ABX-IL-8. Thus, there are a number of relatively distinct binding epitopes for these antibodies within these peptides.

The specificity and uniqueness of two of the antibodies was further examined by determining if peptides that bound to particular antibodies (928 and 809) would also be bound by ABX-IL-8. It was determined that there are a number of peptides which can be bound by mAbs 809 and 928 (ABXha-IL-8), but not by ABX-IL-8. FIG. 9 depicts several peptides that can be bound by Ab 809, which are inhibited by IL-8, but are not bound by ABX-IL-8. FIG. 10 depicts two peptides (and a consensus sequence) that can be bound by Ab 928, which are inhibited by IL-8, but are not bound by ABX-IL-8. Thus, the epitopes between ABX-IL-8 and ABXha-IL-8 appear to be relatively distinct.

Example 7

ABXHA-IL-8 Antibody Binding to Wild-Type IL-8 and Mutant IL-8

In addition to the above examples, the location of the various epitopes can be examined in an alternative manner. For example, altering an amino acid and seeing how it impacts the binding of the various antibodies can indicate not only if that amino acid is involved in the epitope, but if various antibodies share the same epitope. It is believed that the 928 and 809 antibodies, while likely very sensitive to the proline mutation (due to possible conformational changes in the epitope), could retain some small amount of binding ability, even with a proline deleted IL-8. However, it is believed that the 837 antibody should be less influenced by a proline mutation, as it is believed to bind to another epitope that is further from the ABX-IL-8 epitope.

TABLE 6

| Clone | SC/mAb No. | Germline genes used | | | Recognized epitope |
|---|---|---|---|---|---|
| | | V | D | J | |
| 6G11 | 809 | Vh VH3; V3-30 | D6-19 | JH4b | ELRCQCIKTYSK |
| | | Vk VK3; A27 | | JK3 | SEQ ID NO: 79 |
| 36C6 | 837 | Vh VH4-34; VH5/4d76 | D6-13 | JH4b | ELRCQCIKTYSK |
| | | Vk VK4; B3/DPK24 | | JK4 | SEQ ID NO: 79 |
| 46GB | 928 | Vh VH3; V3-30 | D6-19 | JH4b | ELRCQCIKTYSK |
| | | Vk VK3; A27 | | JK3 | SEQ ID NO: 79 |
| | 18K.2.2.2 | | | | KPFHPKFIKELR |
| | | | | | SEQ ID NO: 84 |

Example 8

Inhibition of Neutrophil Chemotactic Activity in Sputums of COPD Patients by Anti-IL-8 Antibodies The example will demonstrate that the antibodies will work in the inhibition of neutrophils chemotactic activity in sputums from patients having COPD. Sputum samples from patients having COPD are obtained. Neutrophils are then isolated from the peripheral blood of normal donors using previously established methods. (See Ferrante, A. & Thong, Y. H. A Rapid One-step Procedure for Purification of Mononuclear and Polymorphonuclear Leukocytes from Human Blood Using a Modification of the Hypaque-Ficoll Technique, J. Immunol. Methods 24:389-393 (1978)). Briefly, blood is collected in heparin and layered over Ficoll. Neutrophils are isolated and washed four times prior to use. Cells are then resuspended at $4\times10^6$/ml in RPMI medium containing 0.5% bovine serum albumin.

The chemotactic activity of neutrophils in the sputum is determined using a Boyden chamber. Two dilutions of sputum (1:10 and 1:100) are utilized and placed (in triplicate) into the lower chambers. A 50 µL suspension of $4\times10^6$ neutrophils/ml is placed into the upper chambers. Each dilution of sputum is tested alone and in the presence of 25 µg/ml of the human anti-IL-8 antibody, an amount is determined (for other IL-8 antibodies) to neutralize >90% of the chemotactic activity generated with 10 nM IL-8. A polycarbonate filter with 5 µl pore size is used to separate the chambers.

After 45 minutes at 37° C., non-migrating cells from the upper surface of the filter are removed by scraping and the underside of the filter is stained with Diff-Quik™ stain. The number of migrating cells is counted by light microscopy. Absolute migration is determined by subtracting out any random migration observed from those wells not containing any sputum.

The results provide data to demonstrate neutrophil chemotaxis as a function of the concentration of the antibody (µg/mL) for various concentrations of IL-8, (1 nM and 10 nM). This also demonstrates the concentration required to neutralize the neutrophil chemotactic activity.

Example 9

Inhibition of Lung Inflammation by In Vivo Administration of IL-8 Antibodies To evaluate the potential utility of systemic administration of IL-8 antibodies (or "anti-IL-8 antibodies") as a treatment for COPD, a rat model of IL-8 induced lung inflammation can be established by intratracheal (i.t.) administration of human IL-8. Rats will receive a vehicle control (PBS+0.1% low endotoxin bovine serum albumin), 0.3 micrograms of human IL-8, 1 microgram of human IL-8, and 3 micrograms of human IL-8 intratracheally. Four hours post i.t. instillation, bronchoalveolar lavage (BAL) will be performed using 3×5 mL aliquots of saline. BAL fluid will be analyzed for total and differential while blood cell counts. Intratracheal administration of human IL-8 (0.3, 1, and 3 micrograms) will trigger dose dependent neutrophil migration into the airways of rats even though rats do not express IL-8. Based on these results, a dose of human IL-8 will be selected for the later studies because this dosage will result in the highest level of neutrophil migration into the lungs. Intravenous administration of 5 mg/kg of an IL-8 antibody will result in significant inhibition of IL-8-induced airway neutrophil migration and accumulation indicating that systemic exposure to the IL-8 antibody will neutralize airway IL-8 and inhibit lung and airway inflammation.

Example 10

Treatment of COPD in Humans

A patient suffering from COPD is identified. A dosage of 5 mg/kg of the anti-IL-8 antibody is administered by intravenous injection to the patient. A booster administration is given three weeks later, and every three weeks thereafter. The anti-IL-8 antibody causes a partial or complete inhibition of neutrophil chemotaxis in the inflamed respiratory tissues. This inhibition of neutrophil chemotaxis reduces the severity of tissue damage to the lungs and air passages caused by the patient's immune response.

Example 11

Treatment of Chronic Bronchitis in Humans

A patient suffering from COPD characterized by chronic bronchitis is identified. A dosage of 5 mg/kg of the anti-IL-8 antibody is administered by intravenous injection to the patient. A booster administration is given three weeks later, and every three weeks thereafter. The anti-IL-8 antibody causes a partial or complete inhibition of neutrophil chemotaxis in the inflamed respiratory tissues. This inhibition of neutrophil chemotaxis reduces the severity of tissue damage to the lungs and air passages caused by the patient's immune response.

Example 12

Treatment of Emphysema in Humans

A patient suffering from COPD characterized by emphysema is identified. A dosage of 5 mg/kg of the anti-IL-8 antibody is administered by intravenous injection to the patient. A booster administration is given three weeks later, and every three weeks thereafter. The anti-IL-8 antibody causes a partial or complete inhibition of neutrophil chemotaxis in the inflamed respiratory tissues. This inhibition of neutrophil chemotaxis reduces the severity of tissue damage to the lungs and air passages caused by the patient's immune response.

Example 13

Treatment of "Irreversible" Asthma in Humans

A patient suffering from COPD characterized by late-stage or "irreversible" asthma is identified. A dosage of 5 mg/kg of the anti-IL-8 antibody is administered by intravenous injection to the patient. A booster administration is given three weeks later, and every three weeks thereafter. The anti-IL-8 antibody causes a partial or complete inhibition of neutrophil chemotaxis in the inflamed respiratory tissues. This inhibition of neutrophil chemotaxis reduces the severity of tissue damage to the lungs and air passages caused by the patient's immune response.

Example 14

Treatment of Bacterial Pneumonia

Neutrophils migrate into the lung in response to a variety of stimuli, including infection by *Streptococcus pneumoniae*. To determine whether the anti-IL-8 antibodies of the instant invention can inhibit such neutrophil migration, thereby ameliorating inflammation in the lung, a rabbit pneumonia model can be used. Briefly, anesthetized New Zealand white rabbits can be given intrabronchial installations of *Streptococcus pneumoniae, Escherichia coli,* or *Pseudomonas aeruginosa* ($3 \times 10^9$ organisms/ml) combined with either IL-8 antibody or a control IgG (final concentration 0.5 mg/ml) and colloidal carbon (5%) in a total volume of 0.5 ml.

After 3 hours and 50 min, the rabbits can receive an intravenous injection of radiolabeled microspheres to measure pulmonary blood flow. At 4 hours, the heart and lungs can be removed and the lungs can be separated. The pneumonic region (usually the left lower lobe) and the corresponding region in the contralateral lung can be lavaged using phosphate-buffered saline. Total leukocyte counts can be obtained using a hemacytometer on the lavage fluid and differential counts can be performed on Wright-stained cytospin preparations.

Treatment with anti-IL-8 antibodies (e.g., IL-8 antibodies) can significantly reduce the number of neutrophils present in the BAL fluid compared to animals that can be treated with isotype control mouse IgG. Thus, anti-IL-8 antibodies can effectively reduce neutrophil emigration in the pneumonic lung.

The foregoing written specification is considered to be sufficient to enable one skilled in the art to practice the invention. The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

All references cited herein, including patents, patent applications, papers, text books, and the like, and the references cited therein, to the extent that they are not already, are hereby incorporated herein by reference in their entirety.

What is claimed is:

1. An isolated monoclonal antibody, or antigen-binding portion thereof, that specifically binds to interleukin-8 (IL-8) comprising:
a heavy chain polypeptide comprising the CDR1, CDR2, and CDR3 sequences of SEQ ID NO: 23, and a light chain polypeptide comprising the CDR1, CDR2, and CDR3 sequences of SEQ ID NO: 21.

2. The monoclonal antibody or antigen-binding portion thereof of claim 1,
wherein the light chain CDR1 sequence is residues 24-34 of SEQ ID NO: 21,
wherein the light chain CDR2 sequence is residues 50-56 of SEQ ID NO): 21; and
wherein the light chain CDR3 sequence is residues 89-96 of SEQ ID NO: 21.

3. The monoclonal antibody or antigen-binding portion thereof of claim 2, wherein the heavy chain variable region comprises a heavy chain CDR1 sequence, a heavy chain CDR2 sequence, and a heavy chain CDR3 sequence,
wherein the heavy chain CDR1 sequence is residues 26-35 of SEQ ID NO: 23;
wherein the heavy chain CDR2 sequence is residues 50-66 of SEQ ID NO: 23; and
wherein the heavy chain CDR3 sequence is residues 99-106 of SEQ ID NO: 23.

4. The monoclonal antibody of claim 1, wherein the light chain comprises SEQ ID NO:21.

5. The monoclonal antibody claim 1, wherein the heavy chain comprises SEQ ID NO:23.

6. The monoclonal antibody of claim 5, wherein the light chain comprises SEQ ID NO:21.

7. The antibody of claim 1, wherein the antibody reduces chemotaxis of neutrophils.

* * * * *

SEQUENCE LISTING

```
<160> NUMBER OF SEQ ID NOS: 114

<210> SEQ ID NO 1
<211> LENGTH: 113
<212> TYPE: PRT
<213> ORGANISM: Homo sapiens

<400> SEQUENCE: 1

Asp Ile Val Met Thr Gln Ser Pro Asp Ser Leu Ala Val Ser Leu Gly
  1               5                  10                  15

Glu Arg Ala Thr Ile Asn Cys Met Ser Ser Gln Ser Leu Leu Tyr Ser
                 20                  25                  30

Ser Asn Asn Lys Asn Tyr Leu Ala Trp Tyr Gln Gln Lys Pro Gly Gln
             35                  40                  45

Pro Pro Lys Leu Leu Ile Tyr Trp Ala Ser Thr Arg Glu Ser Gly Val
         50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Gly Thr Pro Leu Thr Phe Gly Gly Gly Thr Lys Val Glu Ile
                100                 105                 110

Lys

<210> SEQ ID NO 2
<211> LENGTH: 339
<212> TYPE: DNA
<213> ORGANISM: Homo sapiens

<400> SEQUENCE: 2
gacatcgtga tgacccagtc tccagactcc ctggctgtgt ctctgggcga gagggccacc      60
atcaactgca tgtccagcca gagtctttta tacagctcca acaataagaa ctacttagct     120
tggtaccagc agaaaccagg acagcctcct aagctgctca tttactgggc atctacccgg     180
gaatccgggg tccctgaccg attcagtggc agcgggtctg gacagatt cactctcacc      240 atcagcagcc tgcaggctga agatgtggca gtttattact gtcagcaata ttatggtact     300
cctctcactt tcggcggagg gaccaaggtg gagatcaaa                            339
```

```
<210> SEQ ID NO 3
<211> LENGTH: 117
<212> TYPE: PRT
<213> ORGANISM: Homo sapiens

<400> SEQUENCE: 3
```

| Gln | Val | Gln | Leu | Gln | Gln | Trp | Gly | Ala | Gly | Leu | Leu | Lys | Pro | Ser | Glu |
|---|---|---|---|---|---|---|---|---|---|---|---|---|---|---|---|
| 1 | | | | 5 | | | | | 10 | | | | | 15 | |

| Thr | Leu | Ser | Leu | Thr | Cys | Ala | Val | Tyr | Gly | Gly | Phe | Phe | Ser | Gly | Tyr |
|---|---|---|---|---|---|---|---|---|---|---|---|---|---|---|---|
| | | | 20 | | | | | 25 | | | | | 30 | | |

| Tyr | Trp | Ser | Trp | Ile | Arg | Gln | Pro | Pro | Gly | Lys | Gly | Leu | Glu | Trp | Ile |
|---|---|---|---|---|---|---|---|---|---|---|---|---|---|---|---|
| | | 35 | | | | | 40 | | | | | 45 | | | |

| Gly | Glu | Ile | Asn | His | Ser | Gly | Ser | Thr | Asn | Tyr | Asn | Pro | Ser | Leu | Lys |
|---|---|---|---|---|---|---|---|---|---|---|---|---|---|---|---|
| | 50 | | | | | 55 | | | | | 60 | | | | |

| Ser | Arg | Val | Thr | Ile | Ser | Val | Asp | Thr | Ser | Lys | Asn | Gln | Phe | Ser | Leu |
|---|---|---|---|---|---|---|---|---|---|---|---|---|---|---|---|
| 65 | | | | | 70 | | | | | 75 | | | | | 80 |

| Lys | Leu | Ile | Ser | Val | Thr | Ala | Ala | Asp | Thr | Ala | Val | Tyr | Tyr | Cys | Ala |
|---|---|---|---|---|---|---|---|---|---|---|---|---|---|---|---|
| | | | | 85 | | | | | 90 | | | | | 95 | |

| Arg | Gly | Ser | Ala | Ala | Glu | Ala | Phe | Asp | Ile | Trp | Gly | Gln | Gly | Thr | Met |
|---|---|---|---|---|---|---|---|---|---|---|---|---|---|---|---|
| | | | 100 | | | | | 105 | | | | | 110 | | |

| Val | Thr | Val | Ser | Ser |
|---|---|---|---|---|
| | | | 115 | |

```
<210> SEQ ID NO 4
<211> LENGTH: 351
<212> TYPE: DNA
<213> ORGANISM: Homo sapiens

<400> SEQUENCE: 4
caggtgcagc tacaacagtg gggcgcagga ctattgaagc cttcggagac cctgtccctc      60
acctgcgctg tctatggtgg gttcttcagt ggttactact ggagctggat ccgccagccc     120
ccagggaagg ggctggagtg gattggggaa atcaatcata gtggaagcac caactacaac     180
ccgtccctca agagtcgagt caccatatca gtagacacgt ccaagaacca gttctccctg     240
aagttgatct ctgtgaccgc cgcggacacg gctgtgtatt actgtgcgag aggatcagca     300
gccgaggctt ttgatatctg gggccaaggg acaatggtca ccgtctcttc a              351

<210> SEQ ID NO 5
<211> LENGTH: 107
<212> TYPE: PRT
<213> ORGANISM: Homo sapiens

<400> SEQUENCE: 5
```

| Asp | Ile | Gln | Met | Thr | Gln | Ser | Pro | Ser | Ser | Leu | Ser | Ala | Ser | Val | Gly |
|---|---|---|---|---|---|---|---|---|---|---|---|---|---|---|---|
| 1 | | | | 5 | | | | | 10 | | | | | 15 | |

| Asp | Arg | Val | Thr | Ile | Thr | Cys | Arg | Ala | Ser | Gln | Gly | Ile | Ser | Asn | Ser |
|---|---|---|---|---|---|---|---|---|---|---|---|---|---|---|---|
| | | | 20 | | | | | 25 | | | | | 30 | | |

| Leu | Ala | Trp | Tyr | Gln | Gln | Lys | Pro | Gly | Lys | Val | Pro | Asn | Leu | Leu | Ile |
|---|---|---|---|---|---|---|---|---|---|---|---|---|---|---|---|
| | | 35 | | | | | 40 | | | | | 45 | | | |

| Tyr | Ala | Ala | Ser | Thr | Leu | Gln | Ser | Gly | Val | Pro | Ser | Arg | Phe | Ser | Gly |
|---|---|---|---|---|---|---|---|---|---|---|---|---|---|---|---|
| | 50 | | | | | 55 | | | | | 60 | | | | |

| Ser | Gly | Ser | Gly | Thr | Asp | Phe | Thr | Leu | Thr | Ile | Ser | Ser | Leu | Gln | Pro |
|---|---|---|---|---|---|---|---|---|---|---|---|---|---|---|---|
| 65 | | | | | 70 | | | | | 75 | | | | | 80 |

| Glu | Asp | Val | Ala | Thr | Tyr | Tyr | Cys | Gln | Lys | Tyr | Asn | Ser | Val | Pro | Leu |
|---|---|---|---|---|---|---|---|---|---|---|---|---|---|---|---|
| | | | | 85 | | | | | 90 | | | | | 95 | |

| Thr | Phe | Gly | Gly | Gly | Thr | Lys | Val | Glu | Ile | Lys |
|---|---|---|---|---|---|---|---|---|---|---|
| | | | 100 | | | | | 105 | | |

<210> SEQ ID NO 6
<211> LENGTH: 321
<212> TYPE: DNA
<213> ORGANISM: Homo sapiens

<400> SEQUENCE: 6

```
gacatccaga tgacccagtc tccatcctcc ctgtctgcat ctgtaggaga cagagtcacc      60
atcacttgcc gggcgagtca gggcattagc aattctttag cctggtatca gcagaaacca     120
gggaaagttc ctaacctcct gatctatgct gcgtccactt tgcaatctgg ggtcccatct     180
cggtttagtg gcagtggatc tgggacagat ttcactctca ccatcagcag cctgcagcct     240
gaagatgttg caacttatta ctgtcaaaaa tataacagtg tcccgctcac cttcggcgga     300
gggaccaagg tggagatcaa a                                               321
```

<210> SEQ ID NO 7
<211> LENGTH: 124
<212> TYPE: PRT
<213> ORGANISM: Homo sapiens

<400> SEQUENCE: 7

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Gly Tyr
                 20                  25                  30

Tyr Met His Trp Val Arg Gln Ala Pro Gly Gln Gly Leu Glu Trp Met
             35                  40                  45

Gly Trp Ile Asn Ser Asn Ser Gly Gly Thr Asn Tyr Ser Gln Lys Phe
         50                  55                  60

Gln Gly Arg Val Thr Met Thr Arg Asp Thr Ser Ile Ser Thr Val Tyr
 65                  70                  75                  80

Met Glu Leu Ser Arg Leu Arg Ser Asp Asp Thr Ala Val Tyr Tyr Cys
                 85                  90                  95

Ala Ser Gly Tyr Ser Tyr Gly Tyr Arg Tyr Tyr Tyr Gly Met Asp
            100                 105                 110

Val Trp Gly Gln Gly Thr Thr Val Thr Val Ser Ser
            115                 120
```

<210> SEQ ID NO 8
<211> LENGTH: 372
<212> TYPE: DNA
<213> ORGANISM: Homo sapiens

<400> SEQUENCE: 8

```
caggtgcagc tggtgcagtc tggggctgag gtgaagaagc ctggggcctc agtgaaggtc      60
tcctgcaagg cttctggata caccttcacc ggctactata tgcactgggt gcgacaggcc     120
cctggacaag gcttgagtg gatgggatgg atcaactcta acagtggtgg cacaaactat     180
tcacagaagt tccagggcag ggtcaccatg accagggaca cgtccatcag cacagtctac     240
atggagctga gcaggctgag atctgacgac acggccgtgt attactgtgc gagtggatac     300
agctatggtt accgctacta ctactacggt atggacgtct ggggccaagg gaccacggtc     360
accgtctcct ca                                                        372
```

<210> SEQ ID NO 9
<211> LENGTH: 107
<212> TYPE: PRT
<213> ORGANISM: Homo sapiens

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Ser
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Val Pro Leu
                85                  90                  95

Thr Phe Gly Gly Gly Thr Lys Val Glu Ile Asn
            100                 105

<210> SEQ ID NO 10
<211> LENGTH: 321
<212> TYPE: DNA
<213> ORGANISM: Homo sapiens

<400> SEQUENCE: 10
gacatccaga tgacccagtc tccatcctcc ctgtctgcat ctgtaggaga cagagtcacc      60
atcacttgcc gggcgagtca gggcattagc aattctttag cctggtatca gcagaaacca     120
gggaaagttc ctaagctcct gatctatgct gcatccactt tgcaatcagg ggtcccatct     180
cggtttagtg gcagtggatc tgggacagat ttcactctca ccatcagcag cctgcagccg     240
gaagatgttg caacttatta ctgtcaaaag tataacagtg tcccgctcac tttcggcgga     300
gggaccaagg tggagatcaa t                                              321

<210> SEQ ID NO 11
<211> LENGTH: 124
<212> TYPE: PRT
<213> ORGANISM: Homo sapiens

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Ile His Trp Val Arg Gln Ala Pro Gly Gln Gly Leu Glu Trp Met
        35                  40                  45

Gly Trp Ile Asn Ser Asn Ser Gly Gly Thr Asn Phe Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Pro Asp Asp Thr Ala Val Tyr Tyr Cys
                85                  90                  95

Ala Ser Gly Tyr Arg Tyr Gly Tyr Arg Tyr Tyr Tyr Gly Met Asp
            100                 105                 110

Val Trp Gly Gln Gly Thr Thr Val Thr Val Ser Ser
        115                 120

<210> SEQ ID NO 12
<211> LENGTH: 372
<212> TYPE: DNA

<213> ORGANISM: Homo sapiens

<400> SEQUENCE: 12

```
caggtgcagc tggtgcagtc tggggctgag gtgaagaagc ctggggcctc agtgaaggtc      60
tcctgcaagg cttctggata taccttcacc ggctactata tacattgggt gcgacaggcc     120
cctggacaag gcttgagtg gatgggatgg atcaactcta acagtggtgg cacaaacttt     180
gcacagaagt ttcagggcag ggtcaccatg accaggaca cgtccatcag cacagcctac     240
atggagctga gcaggctgag acctgacgac acggccgtgt attactgtgc gagtggatat     300
agatatggct accgctacta ctactacggt atggacgtct ggggccaagg gaccacggtc     360
accgtctcct ca                                                          372
```

<210> SEQ ID NO 13
<211> LENGTH: 107
<212> TYPE: PRT
<213> ORGANISM: Homo sapiens

<400> SEQUENCE: 13

```
Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Asn Val Ser Ser Ser
            20                  25                  30
Tyr Leu Ala Trp Tyr Gln Gln Lys Pro Gly Gln Ala Pro Arg Leu Leu
        35                  40                  45
Ile Tyr Gly Ala Ser Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Gly Ser Ser Phe
                85                  90                  95
Thr Phe Gly Pro Gly Thr Lys Val Asp Ile Lys
            100                 105
```

<210> SEQ ID NO 14
<211> LENGTH: 321
<212> TYPE: DNA
<213> ORGANISM: Homo sapiens

<400> SEQUENCE: 14

```
gaaattgtgt tgacgcagtc tccaggcacc ctgtctttgt ctccagggga aagagccacc      60
ctctcctgca gggccagtca gaatgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcattcac tttcggccct     300
gggaccaaag tggatatcaa a                                                 321
```

<210> SEQ ID NO 15
<211> LENGTH: 117
<212> TYPE: PRT
<213> ORGANISM: Homo sapiens

<400> SEQUENCE: 15

```
Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Ser Tyr
            20                  25                  30
```

Gly Met His Trp Val Arg Gln Ala Pro Gly Lys Gly Leu Glu Trp Val
         35                  40                  45

Ala Asp Ile Ser Tyr Asp Gly Ser Asn Lys Tyr Tyr Ala Asp Ser Val
 50                  55                  60

Lys Gly Arg Phe Thr Ile Ser Arg Asp Asn Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Ile Ala Val Leu Asp Tyr Trp Gly Gln Gly Thr Leu
             100                 105                 110

Val Thr Val Ser Ser
        115

<210> SEQ ID NO 16
<211> LENGTH: 351
<212> TYPE: DNA
<213> ORGANISM: Homo sapiens

<400> SEQUENCE: 16
caggtgcagc tggtggagtc tgggggaggc gtggtccagc ctggagggtc cctgagactc      60
tcctgtgcag cctctggatt caccttcagt agctatggca tgcactgggt ccgccaggct     120
ccaggcaagg ggctggagtg ggtggcagat atatcatatg atggaagtaa taaatactat     180
gcagactccg tgaagggccg attcaccatc tccagagaca attccaagaa cacgctgtat     240
ctgcaaatga acagcctgag agctgaggac acggctgtgt attactgtgc gagagaccgt     300
atagcagtgt tggactactg gggccaggga accctggtca ccgtctcctc a              351

<210> SEQ ID NO 17
<211> LENGTH: 107
<212> TYPE: PRT
<213> ORGANISM: Homo sapiens

<400> SEQUENCE: 17

Asp Ile Gln Met Thr Gln Ser Pro Ser Ser Leu Ser Ala Ser Val Gly
  1               5                  10                  15

Asp Arg Val Thr Ile Ala Cys Arg Ala Ser Gln Gly Ile Arg Asn Asp
             20                  25                  30

Leu Gly Trp Tyr Gln Gln Lys Pro Gly Lys Ala Pro Lys Arg Leu Ile
         35                  40                  45

Tyr Ala Ala Ser Ser Leu Gln Ser Gly Val Pro Ser Arg Phe Gly Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Arg
                 85                  90                  95

Thr Phe Gly Gln Gly Thr Lys Val Glu Ile Lys
             100                 105

<210> SEQ ID NO 18
<211> LENGTH: 321
<212> TYPE: DNA
<213> ORGANISM: Homo sapiens

<400> SEQUENCE: 18
gacattcaga tgacccagtc tccatcctcc ctgtctgcat ctgtgggaga cagagtcacc      60
atcgcttgcc gggcaagtca gggcattaga aatgatttag gctggtatca gcagaagcca     120

```
gggaaagccc ctaaacgcct gatctatgct gcatccagtt tacaaagtgg ggtcccatca    180
aggttcggcg gcagtggatc tgggacagaa ttcactctca caatcagcag cctgcagcct    240
gaagattttg caacttatta ctgtctacag cataatagtt accctcggac gttcggccaa    300
ggaaccaagg tggaaatcaa a                                              321
```

<210> SEQ ID NO 19
<211> LENGTH: 123
<212> TYPE: PRT
<213> ORGANISM: Homo sapiens

<400> SEQUENCE: 19

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Val Met Ser Trp Val Arg Gln Ala Pro Gly Lys Gly Leu Glu Trp Val
        35                  40                  45

Ser Ala Ile Asn Asn Ser Gly Gly Ser Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Gly Arg Phe Leu Glu Trp Ser Tyr Gly Leu Asp Val
            100                 105                 110

Trp Gly Gln Gly Thr Thr Val Thr Val Ser Ser
        115                 120
```

<210> SEQ ID NO 20
<211> LENGTH: 370
<212> TYPE: DNA
<213> ORGANISM: Homo sapiens

<400> SEQUENCE: 20

```
gaagtgcagc tgttggagtc ggggggaggc ttggtacagc ctggggggtc cctgagactc     60
tcctgtgcag cctctggatt cacctttagc agctatgtca tgagctgggt ccgccaggct    120
ccagggaagg gctggagtg gtctcagct attaataata gtggtggtag cacagactac    180
gcagactccg tgaagggccg gttcaccatc tccagagaca attccaagaa cacgctgtat    240
ctgcaaatga acagcctgag agccgaggac acggccgtat attactgtgc gaaagaggga    300 cgattttttgg agtggtccct ctacggtttg acgtctgggg ccaagggac cacggtcacc    360 gtctcctcag                                                           370
```

<210> SEQ ID NO 21
<211> LENGTH: 107
<212> TYPE: PRT
<213> ORGANISM: Homo sapiens

<400> SEQUENCE: 21

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
```

```
              50                  55                  60
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Phe
                 85                  90                  95

Thr Phe Gly Pro Gly Thr Lys Val Asp Ile Lys
                100                 105

<210> SEQ ID NO 22
<211> LENGTH: 321
<212> TYPE: DNA
<213> ORGANISM: Homo sapiens

<400> SEQUENCE: 22
gaaattgtgt tgacgcagtc tccaggcacc ctgtctttgt ctccagggga aagagccacc     60
ctctcctgca gggccagtca gagtgttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcattcac tttcggccct   300
gggaccaaag tggatatcaa a                                             321

<210> SEQ ID NO 23
<211> LENGTH: 117
<212> TYPE: PRT
<213> ORGANISM: Homo sapiens

<400> SEQUENCE: 23

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                 20                  25                  30

Gly Met Leu Trp Val Arg Gln Ala Pro Gly Lys Gly Leu Glu Trp Val
             35                  40                  45

Ala Asp Ile Ser Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                 85                  90                  95

Ala Arg Asp Arg Ile Ala Val Ala Asp Tyr Trp Gly Gln Gly Thr Leu
                100                 105                 110

Val Thr Val Ser Ser
        115

<210> SEQ ID NO 24
<211> LENGTH: 480
<212> TYPE: DNA
<213> ORGANISM: Homo sapiens

<400> SEQUENCE: 24
tgtccagtgt caggtgcagc tggtggagtc tgggggaggc gtggtccagc ctgggaggtc     60
cctgagactc tcctgtgcag cctctggatt caccttcagt agctatggca tgctctgggt   120
ccgccaggct ccaggcaagg ggctggagtg ggtggcagat atatcatatg atggaagtaa   180
taaatactat gcagactccg tgaagggccg attcaccatc tccagagaca attccaagaa   240
cacgctgttt ctgcaaatga acagcctgag agctgaggac acggctgtgt attactgtgc   300
```

```
gagagaccgt atagcagtgg ctgactactg gggccaggga accctggtca ccgtctcctc    360
agcctccacc aagggcccat cggtcttccc cctggcgccc tgctctagaa gcacctccga    420
gagcacagcg gcccttggct gcctggtcaa ggactacttc cccgaaccgg tgacggtgtc    480
```

<210> SEQ ID NO 25
<211> LENGTH: 113
<212> TYPE: PRT
<213> ORGANISM: Homo sapiens

<400> SEQUENCE: 25

```
Asp Ile Val Leu Thr Gln Ser Pro Asp Ser Leu Val Val Ser Leu Gly
 1               5                  10                  15

Glu Arg Ala Thr Ile Asn Cys Lys Ser Ser Gln Ser Val Leu Phe Ser
            20                  25                  30

Ser Asn Asn Arg Lys Tyr Leu Ala Trp Tyr Gln Gln Lys Thr Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Phe Thr Phe Gly Gly Gly Thr Lys Val Glu Ile
            100                 105                 110

Lys
```

<210> SEQ ID NO 26
<211> LENGTH: 339
<212> TYPE: DNA
<213> ORGANISM: Homo sapiens

<400> SEQUENCE: 26

```
gacatcgtgc tgacccagtc tccagactcc ctggttgtgt ctctgggcga gagggccacc     60
atcaactgca gtccagcca gagtgttttg ttcagctcca acaataggaa atatttagct    120
tggtaccagc agaaaacagg acagcctcct aagttgctca tttactgggc atctacccgg    180
gaatccgggg tccctgaccg attcagtggc agcgggtctg ggacagattt cactctcacc    240
atcagcagcc tgcaggctga agatgtggca gtttattact gtcagcaata ttatagtact    300
ccgttcactt tcggcggagg gaccaaggtg gagatcaaa                           339
```

<210> SEQ ID NO 27
<211> LENGTH: 117
<212> TYPE: PRT
<213> ORGANISM: Homo sapiens

<400> SEQUENCE: 27

```
Gln Val Gln Leu Gln Gln Trp Gly Ala Gly Leu Leu Lys Pro Ser Glu
 1               5                  10                  15

Thr Leu Ser Leu Thr Cys Ala Val Phe Gly Gly Thr Phe Ser Gly Tyr
            20                  25                  30

Tyr Trp Thr Trp Ile Arg Gln Pro Pro Gly Lys Gly Leu Glu Trp Ile
        35                  40                  45

Gly Glu Val Ile His His Gly Ser Thr Asn Tyr Ser Pro Ser Leu Lys
    50                  55                  60

Ser Arg Val Thr Ile Ser Ala Asp Thr Ser Lys Ser Gln Phe Ser Leu
65                  70                  75                  80
```

Arg Leu Ser Ser Val Thr Ala Ala Asp Thr Ala Val Tyr Tyr Cys Ala
                85                  90                  95

Arg Gly Gly Ala Ala Ala Ala Leu Asp Ser Trp Gly Gln Gly Thr Leu
            100                 105                 110

Val Ile Val Ser Ser
            115

<210> SEQ ID NO 28
<211> LENGTH: 351
<212> TYPE: DNA
<213> ORGANISM: Homo sapiens

<400> SEQUENCE: 28
caggtgcaac tacagcagtg gggcgcagga ctgttgaagc cttcggaaac cctgtccctc      60
acctgcgctg tctttggtgg gaccttcagt ggttactact ggacctggat ccgccagccc    120
ccagggaagg gactggagtg gattggggaa gtcatccatc atggaagcac caactacagc    180
ccgtccctca agagtcgagt caccatatca gcagacacgt ccaagagcca gttctccctg    240
aggctgagct ctgtgaccgc cgcggacacg gctgtgtatt actgtgcgag aggggggagca    300 gcagctgctc ttgactcctg gggccaggga accctggtca tcgtctcctc a             351

<210> SEQ ID NO 29
<211> LENGTH: 108
<212> TYPE: PRT
<213> ORGANISM: Homo sapiens

<400> SEQUENCE: 29

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Thr Ile Asp Tyr Asn
            20                  25                  30

Tyr Leu His Trp Tyr Gln Gln Lys Pro Gly Gln Ala Pro Arg Leu Leu
        35                  40                  45

Ile Tyr Gly Thr Phe Ile Arg Ala Thr Val Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Ile Ala Val Tyr Tyr Cys Gln Gln Phe Gly Arg Ser Pro
                85                  90                  95

Leu Thr Phe Gly Gly Gly Thr Lys Val Glu Ile Lys
            100                 105

<210> SEQ ID NO 30
<211> LENGTH: 324
<212> TYPE: DNA
<213> ORGANISM: Homo sapiens

<400> SEQUENCE: 30
gaaattgtgt tgacgcagtc tccaggcacc ctgtctttgt ctccagggga aagagccacc      60
ctctcctgca gggccagtca gaccattgac tacaactatt tgcattggta ccagcagaaa    120
cctggccagg ctcccaggct cctcatatat ggtacattca tcaggccacg tgtcatccca    180
gacaggttca gtggcagtgg gtctgggaca gacttcactc tcaccatcag cagactggag    240
cctgaagata ttgcagtgta ttactgtcag cagtttggta ggtcaccgct cactttcggc    300
ggagggacca aggtggagat caaa                                            324

<210> SEQ ID NO 31
<211> LENGTH: 118
<212> TYPE: PRT
<213> ORGANISM: Homo sapiens

<400> SEQUENCE: 31

Gln Val Gln Leu Val Glu Ser Gly Gly Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Tyr Phe Glu Gly Ser Asn Lys Tyr Asn Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Pro Tyr Gly Asp Tyr Leu Asp Tyr Trp Gly Gln Gly Thr
            100                 105                 110

Leu Val Thr Val Ser Ser
            115

<210> SEQ ID NO 32
<211> LENGTH: 354
<212> TYPE: DNA
<213> ORGANISM: Homo sapiens

<400> SEQUENCE: 32

```
caggtgcagc tggtggagtc tgggggaggc gtggtccagc ctgggaggtc cctgagactc    60
tcctgtgcag cgtctggatt caccttcagt aactatggca tgcactgggt ccgccaggct   120
ccaggcaagg gctggagtg gtggcggtt atttattttg aaggaagtaa caaatacaat    180
gcagactccg tgaagggccg attcaccatc tccagagaca attccaagaa cacgctgtat   240
ctgcaaatga acagcctgag agccgaggac acggctgtgt attactgtgc gagatccccc   300
tacggtgact accttgacta ctggggccag ggaaccctgg tcaccgtctc ctca         354
```

<210> SEQ ID NO 33
<211> LENGTH: 107
<212> TYPE: PRT
<213> ORGANISM: Homo sapiens

<400> SEQUENCE: 33

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Ile Leu Thr Ile Ser Arg Leu Glu
65                  70                  75                  80

Pro Glu Asp Phe Ala Val Tyr Tyr Cys Gln Gln Tyr Asp Ser Ser Phe
                85                  90                  95

Thr Phe Gly Pro Gly Thr Lys Val Asp Ile Lys
            100                 105

<210> SEQ ID NO 34
<211> LENGTH: 321
<212> TYPE: DNA
<213> ORGANISM: Homo sapiens

<400> SEQUENCE: 34

```
gaaattgtgt tgacgcagtc tccaggcacc ctgtctttgt ctccagggga aagagccacc      60
ctctcctgca gggccagtca gagtgttagc agtagtttct tagcctggta ccagcagaaa     120
cctggccagg ctcccaggct cctcatctat ggtgcatcca gcagggccac tggcatccca     180
gacaggttca gtggcagtgg gtctgggaca gacttcattc tcaccatcag cagactggag     240
cctgaagatt ttgcagtgta ttactgtcag cagtatgata gctcattcac tttcggccct     300
gggaccaaag tggatatcaa a                                               321
```

<210> SEQ ID NO 35
<211> LENGTH: 117
<212> TYPE: PRT
<213> ORGANISM: Homo sapiens

<400> SEQUENCE: 35

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Gly Met Leu Trp Val Arg Gln Ala Pro Gly Lys Gly Leu Glu Trp Val
         35                  40                  45

Ala Asp Ile Ser Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Phe Tyr Cys
                 85                  90                  95

Ala Arg Asp Arg Ile Ala Val Ala Asp Tyr Trp Gly Gln Gly Thr Leu
            100                 105                 110

Val Thr Val Ser Ser
        115
```

<210> SEQ ID NO 36
<211> LENGTH: 351
<212> TYPE: DNA
<213> ORGANISM: Homo sapiens

<400> SEQUENCE: 36

```
caggtgcagc tggtggagtc tgggggcggc gtggtccagc ctgggaggtc cctgagactc      60
tcctgtgcag cctctggatt caccttcagt agctatggca tgctctgggt ccgccaggct     120
ccaggcaagg ggctggagtg gtggcagat atatcatatg atggaagtaa taatactat      180
gcagactccg tgaagggccg attcaccatc tccagagaca attccaagaa cacgctgtat     240
ctgcaaatga acagcctgag agctgaggac acggctgtgt tttattgtgc gagagaccgt     300
atagcagtgg ctgactactg gggccaggga accctggtca ccgtctcctc a              351
```

<210> SEQ ID NO 37
<211> LENGTH: 107
<212> TYPE: PRT
<213> ORGANISM: Homo sapiens

<400> SEQUENCE: 37

-continued

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Arg Pro Gly Gln Ala Pro Arg Leu Leu
        35                  40                  45

Ile Tyr Gly Ala Tyr Arg Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Asp Gly Ser Ser Phe
                85                  90                  95

Thr Phe Gly Pro Gly Thr Lys Val Asp Ile Lys
            100                 105

<210> SEQ ID NO 38
<211> LENGTH: 321
<212> TYPE: DNA
<213> ORGANISM: Homo sapiens

<400> SEQUENCE: 38
gaaattgtgt tgacgcagtc tccaggcacc ctgtctttgt ctccagggga aagagccacc      60
ctctcctgca gggccagtca gagtgttagc agcagctact tagcctggta ccagcagaga     120
cctggccagg ctcccaggct cctcatctat ggtgcataca aaggggccac tggcatccca     180
gacaggttca gtggcagtgg gtctgggaca gacttcactc tcaccatcag cagactggag     240
cctgaagatt ttgcagtgta ttactgtcag caggatggca gctcattcac tttcggccct     300
gggaccaaag tggatatcaa a                                                321

<210> SEQ ID NO 39
<211> LENGTH: 117
<212> TYPE: PRT
<213> ORGANISM: Homo sapiens

<400> SEQUENCE: 39

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Leu Ile Ser Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp His Ile Ala Val Ala Asp Tyr Trp Gly Gln Gly Thr Leu
            100                 105                 110

Val Thr Val Ser Ser
115

<210> SEQ ID NO 40
<211> LENGTH: 351
<212> TYPE: DNA
<213> ORGANISM: Homo sapiens

<400> SEQUENCE: 40

```
caggtgcagc tggtggagtc tgggggaggc gtggtccagc ctggggaggtc cctgagactc    60 tcctgtgcag cctctggatt caccttcagt acctatggca tgcactgggt ccgccaggct   120
ccaggcaagg gctggagtg gtggcactt atatcatatg atggaagtaa taaatactat   180
gcagactccg tgaagggccg attcaccatc tccagagaca attccaagaa cacgctgtat   240
ctgcaaatga acagcctgag agctgaggac acggctgtgt attactgtgc gagagatcat   300
atagcagtgg ctgactactg gggccaggga accctggtca ccgtctcctc a            351
```

<210> SEQ ID NO 41
<211> LENGTH: 113
<212> TYPE: PRT
<213> ORGANISM: Homo sapiens

<400> SEQUENCE: 41

```
Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Val Leu Tyr Ser
            20                  25                  30

Ser Asn Asn Lys Asn Tyr Leu Ala Trp Tyr Gln Gln Lys Ser Gly Gln
        35                  40                  45

Pro Pro Lys Leu Leu Ile Tyr Leu Ala Ser Ile Arg Glu Ser Gly Val
    50                  55                  60

Pro Asp Arg Phe Ser Gly Ser Gly Ser Gly Thr Asp Phe Ala Leu Thr
65                  70                  75                  80

Ile Ser Asn Leu Gln Ala Glu Asp Val Ala Val Tyr Tyr Cys Gln Gln
                85                  90                  95

Tyr Tyr Ser Thr Pro Leu Thr Phe Gly Gly Gly Thr Lys Val Glu Ile
            100                 105                 110

Lys
```

<210> SEQ ID NO 42
<211> LENGTH: 339
<212> TYPE: DNA
<213> ORGANISM: Homo sapiens

<400> SEQUENCE: 42

```
gacatcgtga tgacccagtc tccagactcc ctggctgtgt ctctgggcga gagggccacc    60
atcaactgca ggtccagcca gagtgtttta tacagttcca acaataagaa ctacttagct   120
tggtaccagc agaaatcagg acagcctcct aaactactgt tttacttggc atctattcgg   180
gaatccgggg tccctgaccg attcagtggc agcgggtctg gacagatttc gctctcacc   240 atcagcaacc tgcaggctga agatgtggca gtttattact gtcagcaata ttatagtact   300
ccgctcactt tcggcggtgg gaccaaggtg gagatcaaa                          339
```

<210> SEQ ID NO 43
<211> LENGTH: 118
<212> TYPE: PRT
<213> ORGANISM: Homo sapiens

<400> SEQUENCE: 43

```
Gln Val Gln Leu Gln Gln Trp Gly Ala Gly Leu Leu Lys Pro Ser Glu
1               5                   10                  15

Ser Leu Ser Leu Thr Cys Ala Val Tyr Gly Gly Ser Phe Phe Ser Gly
            20                  25                  30

Tyr Tyr Trp Ser Trp Ile Arg Gln Pro Pro Gly Lys Gly Leu Glu Trp
        35                  40                  45
```

```
Ile Gly Glu Ile Thr His Ser Gly Asn Thr Asn Tyr Asn Pro Ser Leu
        50                  55                  60
Lys Ser Arg Val Ser Ile Ser Val Asp Thr Ser Thr Asn Gln Phe Ser
 65                  70                  75                  80
Leu Lys Leu Ser Ser Val Thr Ala Ala Asp Thr Ala Val Tyr Tyr Cys
                85                  90                  95
Gly Arg Gly Gly Ala Glu Val Gly Phe Asp Tyr Trp Gly Gln Gly Thr
            100                 105                 110
Leu Val Thr Val Ser Ser
            115

<210> SEQ ID NO 44
<211> LENGTH: 354
<212> TYPE: DNA
<213> ORGANISM: Homo sapiens

<400> SEQUENCE: 44
caggtgcaac tacagcagtg gggcgcagga ctgttgaagc cttcggagtc cctgtccctc      60
acctgcgctg tctatggtgg gtccttcttc agtggttact actggagttg gatccgccag     120
cccccaggga aggggctgga gtggattggg gaaatcactc atagtggaaa caccaactac     180
aacccgtccc tcaagagtcg agtcagcata tcagttgaca cgtccacgaa ccagttctcc     240
ctgaagttga gctctgtgac cgccgcggac acggctgtct attactgtgg gagaggggga     300
gcagaagttg gttttgacta ctggggccag ggaaccctgg tcaccgtctc ctca           354

<210> SEQ ID NO 45
<211> LENGTH: 113
<212> TYPE: PRT
<213> ORGANISM: Homo sapiens

<400> SEQUENCE: 45

Asp Ile Val Met Thr Gln Ser Pro Asp Ser Leu Val Val Ser Leu Gly
  1               5                  10                  15
Glu Arg Ala Thr Ile Asn Cys Lys Ser Ser Gln Ser Val Leu Tyr Ser
                20                  25                  30
Ser Asn Asn Lys Asn Tyr Leu Ala Trp Tyr Gln Gln Lys Pro Gly Gln
            35                  40                  45
Pro Pro Lys Leu Leu Ile Tyr Trp Ala Ser Thr Arg Glu Ser Gly Val
 50                  55                  60
Pro Asp Arg Phe Ser Gly Ser Gly Ser Gly Thr Asp Phe Thr Leu Thr
 65                  70                  75                  80
Ile Ser Ser Leu Gln Ala Glu Asp Val Ala Val Tyr Tyr Cys Gln Gln
                85                  90                  95
Tyr Tyr Asp Thr Pro Phe Thr Phe Gly Gly Gly Thr Lys Val Glu Ile
            100                 105                 110
Lys

<210> SEQ ID NO 46
<211> LENGTH: 339
<212> TYPE: DNA
<213> ORGANISM: Homo sapiens

<400> SEQUENCE: 46
gacatcgtga tgacccagtc tccagactcc ctggttgtgt ctctgggcga gagggccacc      60
atcaactgca gtccagcca gagtgttttg tacagctcca acaataagaa ctacttagct     120
tggtaccagc agaaaccagg acagcctcct aagttgctca tttactgggc atctacccgg     180
```

```
gaatccgggg tccctgaccg attcagtggc agcgggtctg ggacagattt cactctcacc      240
atcagcagcc tgcaggctga agatgtggca gtttattact gtcagcaata ttatgatact      300
ccgttcactt tcggcggagg gaccaaggtg gagatcaaa                             339
```

<210> SEQ ID NO 47
<211> LENGTH: 117
<212> TYPE: PRT
<213> ORGANISM: Homo sapiens

<400> SEQUENCE: 47

```
Gln Val Gln Leu Gln Gln Trp Gly Ala Gly Leu Leu Lys Pro Ser Glu
 1               5                  10                  15

Thr Leu Ser Leu Thr Cys Ala Val Phe Gly Gly Ser Phe Ser Gly Tyr
            20                  25                  30

Tyr Trp Thr Trp Ile Arg Gln Pro Pro Gly Lys Gly Leu Glu Trp Ile
        35                  40                  45

Gly Glu Ile Ile His His Gly Ser Thr Asn Tyr Ser Pro Ser Leu Lys
    50                  55                  60

Ser Arg Val Thr Ile Ser Ala Asp Thr Ser Lys Ser Gln Phe Ser Leu
65                  70                  75                  80

Arg Leu Ser Ser Val Thr Ala Ala Asp Thr Ala Val Tyr Tyr Cys Ala
                85                  90                  95

Arg Gly Gly Ala Ala Ala Gly Leu Asp Ser Trp Gly Gln Gly Thr Leu
            100                 105                 110

Val Thr Val Ser Ser
        115
```

<210> SEQ ID NO 48
<211> LENGTH: 351
<212> TYPE: DNA
<213> ORGANISM: Homo sapiens

<400> SEQUENCE: 48

```
caggtgcagc tacagcagtg gggcgcagga ctgttgaagc cttcggaaac cctgtccctc      60
acctgcgctg tctttggtgg gtccttcagt ggttactact ggacctggat ccgccagccc     120
ccagggaagg gactggagtg gattggggaa atcatccatc atggaagcac caactacagc     180
ccgtccctca agagtcgagt caccatatca gcagacacgt ccaagagcca gttctccctg     240
aggctgagct ctgtgaccgc cgcggacacg gctgtgtatt actgtgcgag agggggagca     300
gcagctggtc ttgactcctg gggccaggga accctggtca ccgtctcctc a              351
```

<210> SEQ ID NO 49
<211> LENGTH: 12
<212> TYPE: PRT
<213> ORGANISM: Homo sapiens

<400> SEQUENCE: 49

```
Tyr Ser Lys Pro Phe His Pro Lys Phe Ile Lys Glu
 1               5                  10
```

<210> SEQ ID NO 50
<211> LENGTH: 124
<212> TYPE: PRT
<213> ORGANISM: Homo sapiens
<220> FEATURE:
<221> NAME/KEY: VARIANT
<222> LOCATION: 99, 100, 101, 102, 103, 104, 105, 106, 107, 108, 109,
      110, 111, 112, 113
<223> OTHER INFORMATION: Xaa = Any Amino Acid -continued

```
<400> SEQUENCE: 50

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Xaa Xaa Xaa Xaa Xaa Xaa Xaa Xaa Xaa Xaa Xaa Xaa Xaa Xaa
            100                 105                 110

Xaa Trp Gly Gln Gly Thr Thr Val Thr Val Ser Ser
        115                 120

<210> SEQ ID NO 51
<211> LENGTH: 123
<212> TYPE: PRT
<213> ORGANISM: Homo sapiens
<220> FEATURE:
<221> NAME/KEY: VARIANT
<222> LOCATION: 99, 100, 101, 102, 103, 104, 105, 106, 107, 108, 109,
      110, 111, 112
<223> OTHER INFORMATION: Xaa = Any Amino Acid

<400> SEQUENCE: 51

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Xaa Xaa Xaa Xaa Xaa Xaa Xaa Xaa Xaa Xaa Xaa Xaa Xaa Xaa
            100                 105                 110

Trp Gly Gln Gly Thr Thr Val Thr Val Ser Ser
        115                 120

<210> SEQ ID NO 52
<211> LENGTH: 117
<212> TYPE: PRT
<213> ORGANISM: Homo sapiens
<220> FEATURE:
<221> NAME/KEY: VARIANT
<222> LOCATION: 99, 100, 101, 102, 103, 104, 105, 106
<223> OTHER INFORMATION: Xaa = Any Amino Acid

<400> SEQUENCE: 52

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
```

-continued

```
                    20                  25                  30
Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Xaa Xaa Xaa Xaa Xaa Xaa Xaa Trp Gly Gln Gly Thr Leu
                100                 105                 110

Val Thr Val Ser Ser
        115

<210> SEQ ID NO 53
<211> LENGTH: 118
<212> TYPE: PRT
<213> ORGANISM: Homo sapiens
<220> FEATURE:
<221> NAME/KEY: VARIANT
<222> LOCATION: 99, 100, 101, 102, 103, 104, 105, 106, 107
<223> OTHER INFORMATION: Xaa = Any Amino Acid

<400> SEQUENCE: 53

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Xaa Xaa Xaa Xaa Xaa Xaa Xaa Xaa Trp Gly Gln Gly Thr
                100                 105                 110

Leu Val Thr Val Ser Ser
        115

<210> SEQ ID NO 54
<211> LENGTH: 117
<212> TYPE: PRT
<213> ORGANISM: Homo sapiens
<220> FEATURE:
<221> NAME/KEY: VARIANT
<222> LOCATION: 98, 99, 100, 101, 102, 103, 104, 105, 106
<223> OTHER INFORMATION: Xaa = Any Amino Acid

<400> SEQUENCE: 54

Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
            35                  40                  45

Gly Glu Ile Asn His Ser Gly Ser Thr Asn Tyr Asn Pro Ser Leu Lys
 50                  55                  60
```

```
Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Xaa Xaa Xaa Xaa Xaa Xaa Xaa Xaa Trp Gly Gln Gly Thr Leu
            100                 105                 110

Val Thr Val Ser Ser
        115

<210> SEQ ID NO 55
<211> LENGTH: 117
<212> TYPE: PRT
<213> ORGANISM: Homo sapiens
<220> FEATURE:
<221> NAME/KEY: VARIANT
<222> LOCATION: 98, 99, 100, 101, 102, 103, 104, 105, 106
<223> OTHER INFORMATION: Xaa = Any Amino Acid

<400> SEQUENCE: 55

Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
                 20                  25                  30

Tyr Trp Ser Trp Ile Arg Gln Pro Pro Gly Lys Gly Leu Glu Trp Ile
            35                  40                  45

Gly Glu Ile Asn His Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Xaa Xaa Xaa Xaa Xaa Xaa Xaa Xaa Trp Gly Gln Gly Thr Met
            100                 105                 110

Val Thr Val Ser Ser
        115

<210> SEQ ID NO 56
<211> LENGTH: 117
<212> TYPE: PRT
<213> ORGANISM: Homo sapiens
<220> FEATURE:
<221> NAME/KEY: VARIANT
<222> LOCATION: 98, 99, 100, 101, 102, 103, 104, 105, 106
<223> OTHER INFORMATION: Xaa = Any Amino Acid

<400> SEQUENCE: 56

Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
                 20                  25                  30

Tyr Trp Ser Trp Ile Arg Gln Pro Pro Gly Lys Gly Leu Glu Trp Ile
            35                  40                  45

Gly Gly Glu Ile Asn His Ser Gly Ser Thr Asn Tyr Asn Pro Ser Leu
         50                  55                  60

Lys Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Xaa Xaa Xaa Xaa Xaa Xaa Xaa Xaa Trp Gly Gln Gly Thr Leu
            100                 105                 110
```

```
Val Thr Val Ser Ser
        115

<210> SEQ ID NO 57
<211> LENGTH: 107
<212> TYPE: PRT
<213> ORGANISM: Homo sapiens

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Leu
                85                  90                  95

Thr Phe Gly Gly Gly Thr Lys Val Glu Ile Lys
            100                 105

<210> SEQ ID NO 58
<211> LENGTH: 108
<212> TYPE: PRT
<213> ORGANISM: Homo sapiens

<400> SEQUENCE: 58

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Phe Thr Phe Gly Pro Gly Thr Lys Val Asp Ile Lys
            100                 105

<210> SEQ ID NO 59
<211> LENGTH: 108
<212> TYPE: PRT
<213> ORGANISM: Homo sapiens

<400> SEQUENCE: 59

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
```

-continued

```
                    50                  55                  60
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Leu Thr Phe Gly Gly Gly Thr Lys Val Glu Ile Lys
            100                 105
```

<210> SEQ ID NO 60
<211> LENGTH: 107
<212> TYPE: PRT
<213> ORGANISM: Homo sapiens

<400> SEQUENCE: 60

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
                 20                  25                  30

Leu Gly Trp Tyr Gln Gln Lys Pro Gly Lys Ala Pro Lys Arg Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Trp
                 85                  90                  95

Thr Phe Gly Gln Gly Thr Lys Val Glu Ile Lys
            100                 105
```

<210> SEQ ID NO 61
<211> LENGTH: 113
<212> TYPE: PRT
<213> ORGANISM: Homo sapiens

<400> SEQUENCE: 61

```
Asp Ile Val Met Thr Gln Ser Pro Asp Ser Leu Ala Val Ser Leu Gly
  1               5                  10                  15

Glu Arg Ala Thr Ile Asn Cys Lys Ser Ser Gln Ser Val Leu Tyr Ser
                 20                  25                  30

Ser Asn Asn Lys Asn Tyr Leu Ala Trp Tyr Gln Gln Lys Pro Gly Gln
             35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Ser Thr Pro Leu Thr Phe Gly Gly Gly Thr Lys Val Glu Ile
            100                 105                 110

Lys
```

<210> SEQ ID NO 62
<211> LENGTH: 20
<212> TYPE: PRT
<213> ORGANISM: Homo sapiens

<400> SEQUENCE: 62

```
Leu Arg Cys Gln Cys Ile Lys Thr Tyr Ser Lys Pro Phe His Pro Lys
```

```
                1               5                  10                 15
Phe Ile Lys Glu
                20

<210> SEQ ID NO 63
<211> LENGTH: 6
<212> TYPE: PRT
<213> ORGANISM: Homo sapiens
<220> FEATURE:
<221> NAME/KEY: VARIANT
<222> LOCATION: 3, 5
<223> OTHER INFORMATION: Xaa = Any Amino Acid

<400> SEQUENCE: 63

Lys Pro Xaa Pro Xaa Phe
1               5

<210> SEQ ID NO 64
<211> LENGTH: 7
<212> TYPE: PRT
<213> ORGANISM: Homo sapiens

<400> SEQUENCE: 64

Lys Pro Phe His Pro Lys Phe
1               5

<210> SEQ ID NO 65
<211> LENGTH: 12
<212> TYPE: PRT
<213> ORGANISM: Homo sapiens

<400> SEQUENCE: 65

Glu Gly Lys Pro Phe Pro Thr Phe Leu Leu Arg Ser
1               5                  10

<210> SEQ ID NO 66
<211> LENGTH: 12
<212> TYPE: PRT
<213> ORGANISM: Homo sapiens

<400> SEQUENCE: 66

Val Trp Ser Lys Met Met Pro Gln Phe Leu Thr Pro
1               5                  10

<210> SEQ ID NO 67
<211> LENGTH: 12
<212> TYPE: PRT
<213> ORGANISM: Homo sapiens

<400> SEQUENCE: 67

His Ala Lys Pro Leu Pro His Trp Met Gly His Pro
1               5                  10

<210> SEQ ID NO 68
<211> LENGTH: 12
<212> TYPE: PRT
<213> ORGANISM: Homo sapiens

<400> SEQUENCE: 68

Asn Gly Asn Val Lys Pro Val Pro Lys Phe Leu His
1               5                  10

<210> SEQ ID NO 69
<211> LENGTH: 12
<212> TYPE: PRT
<213> ORGANISM: Homo sapiens
```

<400> SEQUENCE: 69

Ile Gly Ser Pro Lys Pro Tyr Pro His Phe Leu Gly
1               5                   10

<210> SEQ ID NO 70
<211> LENGTH: 12
<212> TYPE: PRT
<213> ORGANISM: Homo sapiens

<400> SEQUENCE: 70

Ser Gln Leu Asn Lys Pro Arg Pro Ile Phe Leu Tyr
1               5                   10

<210> SEQ ID NO 71
<211> LENGTH: 12
<212> TYPE: PRT
<213> ORGANISM: Homo sapiens

<400> SEQUENCE: 71

Asn Pro Leu Gln Ser Lys Pro Ile Pro Ile Phe Leu
1               5                   10

<210> SEQ ID NO 72
<211> LENGTH: 12
<212> TYPE: PRT
<213> ORGANISM: Homo sapiens

<400> SEQUENCE: 72

Val Pro Gln Lys Lys Phe Pro Ile Phe Leu Asn Leu
1               5                   10

<210> SEQ ID NO 73
<211> LENGTH: 12
<212> TYPE: PRT
<213> ORGANISM: Homo sapiens

<400> SEQUENCE: 73

Val Pro Ser Lys Thr Met Pro His Phe Leu Leu Thr
1               5                   10

<210> SEQ ID NO 74
<211> LENGTH: 12
<212> TYPE: PRT
<213> ORGANISM: Homo sapiens

<400> SEQUENCE: 74

Tyr Glu Lys Pro Ile Pro His Tyr Leu Ser Gln Arg
1               5                   10

<210> SEQ ID NO 75
<211> LENGTH: 12
<212> TYPE: PRT
<213> ORGANISM: Homo sapiens

<400> SEQUENCE: 75

Ala Val Leu Pro Arg Ser Ala Lys Glu Leu Arg Cys
1               5                   10

<210> SEQ ID NO 76
<211> LENGTH: 12
<212> TYPE: PRT
<213> ORGANISM: Homo sapiens

<400> SEQUENCE: 76

```
Leu Pro Arg Ser Ala Lys Glu Leu Arg Cys Gln Cys
 1               5                  10
```

<210> SEQ ID NO 77
<211> LENGTH: 12
<212> TYPE: PRT
<213> ORGANISM: Homo sapiens

<400> SEQUENCE: 77

```
Arg Ser Ala Lys Glu Leu Arg Cys Gln Cys Ile Lys
 1               5                  10
```

<210> SEQ ID NO 78
<211> LENGTH: 12
<212> TYPE: PRT
<213> ORGANISM: Homo sapiens

<400> SEQUENCE: 78

```
Ala Lys Glu Leu Arg Cys Gln Cys Ile Lys Thr Tyr
 1               5                  10
```

<210> SEQ ID NO 79
<211> LENGTH: 12
<212> TYPE: PRT
<213> ORGANISM: Homo sapiens

<400> SEQUENCE: 79

```
Glu Leu Arg Cys Gln Cys Ile Lys Thr Tyr Ser Lys
 1               5                  10
```

<210> SEQ ID NO 80
<211> LENGTH: 12
<212> TYPE: PRT
<213> ORGANISM: Homo sapiens

<400> SEQUENCE: 80

```
Arg Cys Gln Cys Ile Lys Thr Tyr Ser Lys Pro Phe
 1               5                  10
```

<210> SEQ ID NO 81
<211> LENGTH: 12
<212> TYPE: PRT
<213> ORGANISM: Homo sapiens

<400> SEQUENCE: 81

```
Gln Cys Ile Lys Thr Tyr Ser Lys Pro Phe His Pro
 1               5                  10
```

<210> SEQ ID NO 82
<211> LENGTH: 12
<212> TYPE: PRT
<213> ORGANISM: Homo sapiens

<400> SEQUENCE: 82

```
Ile Lys Thr Tyr Ser Lys Pro Phe His Pro Lys Phe
 1               5                  10
```

<210> SEQ ID NO 83
<211> LENGTH: 12
<212> TYPE: PRT
<213> ORGANISM: Homo sapiens

<400> SEQUENCE: 83

```
Tyr Ser Lys Pro Phe His Pro Lys Phe Ile Lys Glu
 1               5                  10
```

<210> SEQ ID NO 84
<211> LENGTH: 12
<212> TYPE: PRT
<213> ORGANISM: Homo sapiens

<400> SEQUENCE: 84

Lys Pro Phe His Pro Lys Phe Ile Lys Glu Leu Arg
1               5                   10

<210> SEQ ID NO 85
<211> LENGTH: 12
<212> TYPE: PRT
<213> ORGANISM: Homo sapiens

<400> SEQUENCE: 85

Phe His Pro Lys Phe Ile Lys Glu Leu Arg Val Ile
1               5                   10

<210> SEQ ID NO 86
<211> LENGTH: 12
<212> TYPE: PRT
<213> ORGANISM: Homo sapiens

<400> SEQUENCE: 86

Pro Lys Phe Ile Lys Glu Leu Arg Val Ile Glu Ser
1               5                   10

<210> SEQ ID NO 87
<211> LENGTH: 12
<212> TYPE: PRT
<213> ORGANISM: Homo sapiens

<400> SEQUENCE: 87

Phe Ile Lys Glu Leu Arg Val Ile Glu Ser Gly Pro
1               5                   10

<210> SEQ ID NO 88
<211> LENGTH: 12
<212> TYPE: PRT
<213> ORGANISM: Homo sapiens

<400> SEQUENCE: 88

Lys Glu Leu Arg Val Ile Glu Ser Gly Pro His Cys
1               5                   10

<210> SEQ ID NO 89
<211> LENGTH: 12
<212> TYPE: PRT
<213> ORGANISM: Homo sapiens

<400> SEQUENCE: 89

Leu Arg Val Ile Glu Ser Gly Pro His Cys Ala Asn
1               5                   10

<210> SEQ ID NO 90
<211> LENGTH: 12
<212> TYPE: PRT
<213> ORGANISM: Homo sapiens

<400> SEQUENCE: 90

Ile Glu Ser Gly Pro His Cys Ala Asn Thr Glu Ile
1               5                   10

<210> SEQ ID NO 91
<211> LENGTH: 12

```
<212> TYPE: PRT
<213> ORGANISM: Homo sapiens

<400> SEQUENCE: 91

Ser Gly Pro His Cys Ala Asn Thr Glu Ile Ile Val
1               5                   10

<210> SEQ ID NO 92
<211> LENGTH: 12
<212> TYPE: PRT
<213> ORGANISM: Homo sapiens

<400> SEQUENCE: 92

Pro His Cys Ala Asn Thr Glu Ile Ile Val Lys Leu
1               5                   10

<210> SEQ ID NO 93
<211> LENGTH: 12
<212> TYPE: PRT
<213> ORGANISM: Homo sapiens

<400> SEQUENCE: 93

Cys Ala Asn Thr Glu Ile Ile Val Lys Leu Ser Asp
1               5                   10

<210> SEQ ID NO 94
<211> LENGTH: 12
<212> TYPE: PRT
<213> ORGANISM: Homo sapiens

<400> SEQUENCE: 94

Asn Thr Glu Ile Ile Val Lys Leu Ser Asp Gly Arg
1               5                   10

<210> SEQ ID NO 95
<211> LENGTH: 12
<212> TYPE: PRT
<213> ORGANISM: Homo sapiens

<400> SEQUENCE: 95

Glu Ile Ile Val Lys Leu Ser Asp Gly Arg Glu Leu
1               5                   10

<210> SEQ ID NO 96
<211> LENGTH: 12
<212> TYPE: PRT
<213> ORGANISM: Homo sapiens

<400> SEQUENCE: 96

Ile Val Lys Leu Ser Asp Gly Arg Glu Leu Cys Leu
1               5                   10

<210> SEQ ID NO 97
<211> LENGTH: 12
<212> TYPE: PRT
<213> ORGANISM: Homo sapiens

<400> SEQUENCE: 97

Leu Ser Asp Gly Arg Glu Leu Cys Leu Asp Pro Lys
1               5                   10

<210> SEQ ID NO 98
<211> LENGTH: 12
<212> TYPE: PRT
<213> ORGANISM: Homo sapiens
```

```
<400> SEQUENCE: 98

Asp Gly Arg Glu Leu Cys Leu Asp Pro Lys Glu Asn
 1               5                  10

<210> SEQ ID NO 99
<211> LENGTH: 12
<212> TYPE: PRT
<213> ORGANISM: Homo sapiens

<400> SEQUENCE: 99

Arg Glu Leu Cys Leu Asp Pro Lys Glu Asn Trp Val
 1               5                  10

<210> SEQ ID NO 100
<211> LENGTH: 12
<212> TYPE: PRT
<213> ORGANISM: Homo sapiens

<400> SEQUENCE: 100

Leu Cys Leu Asp Pro Lys Glu Asn Trp Val Gln Arg
 1               5                  10

<210> SEQ ID NO 101
<211> LENGTH: 12
<212> TYPE: PRT
<213> ORGANISM: Homo sapiens

<400> SEQUENCE: 101

Leu Asp Pro Lys Glu Asn Trp Val Gln Arg Val Val
 1               5                  10

<210> SEQ ID NO 102
<211> LENGTH: 12
<212> TYPE: PRT
<213> ORGANISM: Homo sapiens

<400> SEQUENCE: 102

Pro Lys Glu Asn Trp Val Gln Arg Val Val Glu Lys
 1               5                  10

<210> SEQ ID NO 103
<211> LENGTH: 12
<212> TYPE: PRT
<213> ORGANISM: Homo sapiens

<400> SEQUENCE: 103

Glu Asn Trp Val Gln Arg Val Val Glu Lys Phe Leu
 1               5                  10

<210> SEQ ID NO 104
<211> LENGTH: 12
<212> TYPE: PRT
<213> ORGANISM: Homo sapiens

<400> SEQUENCE: 104

Val Gln Arg Val Val Glu Lys Phe Leu Lys Arg Ala
 1               5                  10

<210> SEQ ID NO 105
<211> LENGTH: 12
<212> TYPE: PRT
<213> ORGANISM: Homo sapiens

<400> SEQUENCE: 105

Val Val Glu Lys Phe Leu Lys Arg Ala Glu Asn Ser
```

```
<210> SEQ ID NO 106
<211> LENGTH: 64
<212> TYPE: PRT
<213> ORGANISM: Homo sapiens

<400> SEQUENCE: 106

Ser Ala Lys Glu Leu Arg Cys Gln Cys Ile Lys Thr Tyr Ser Lys Pro
 1               5                  10                  15

Phe His Pro Lys Phe Ile Lys Glu Leu Arg Val Ile Glu Ser Gly Pro
             20                  25                  30

His Cys Ala Asn Thr Glu Ile Ile Val Lys Leu Ser Asp Gly Arg Glu
         35                  40                  45

Leu Cys Leu Asp Pro Lys Glu Asn Trp Val Gln Arg Val Val Glu Lys
     50                  55                  60

<210> SEQ ID NO 107
<211> LENGTH: 12
<212> TYPE: PRT
<213> ORGANISM: Homo sapiens

<400> SEQUENCE: 107

Gly Tyr Lys Ser Leu Pro His Ser Leu Pro Met Ile
 1               5                  10

<210> SEQ ID NO 108
<211> LENGTH: 12
<212> TYPE: PRT
<213> ORGANISM: Homo sapiens

<400> SEQUENCE: 108

Thr Pro Tyr Lys Ala Phe Asn His Ser Leu Pro Leu
 1               5                  10

<210> SEQ ID NO 109
<211> LENGTH: 12
<212> TYPE: PRT
<213> ORGANISM: Homo sapiens

<400> SEQUENCE: 109

Tyr Lys Gln Pro Asn His Ser Met Pro Met Leu Ser
 1               5                  10

<210> SEQ ID NO 110
<211> LENGTH: 11
<212> TYPE: PRT
<213> ORGANISM: Homo sapiens

<400> SEQUENCE: 110

Tyr Lys Ala Pro Asn His Ser Leu Pro Met Ile
 1               5                  10

<210> SEQ ID NO 111
<211> LENGTH: 58
<212> TYPE: PRT
<213> ORGANISM: Homo sapiens

<400> SEQUENCE: 111

Ser Ala Lys Glu Leu Arg Cys Gln Cys Ile Lys Thr Tyr Ser Lys Pro
 1               5                  10                  15

Phe His Pro Lys Phe Ile Lys Glu Leu Arg Val Ile Glu Ser Gly Pro
             20                  25                  30
```

```
His Cys Ala Asn Thr Glu Ile Ile Val Lys Leu Ser Asp Gly Arg Glu
        35                  40                  45

Leu Cys Leu Asp Pro Lys Glu Asn Trp Val
        50                  55

<210> SEQ ID NO 112
<211> LENGTH: 12
<212> TYPE: PRT
<213> ORGANISM: Homo sapiens

<400> SEQUENCE: 112

Ser Lys His Trp His Pro Leu Leu Tyr Ser Gln Phe
1               5                   10

<210> SEQ ID NO 113
<211> LENGTH: 12
<212> TYPE: PRT
<213> ORGANISM: Homo sapiens

<400> SEQUENCE: 113

Tyr Ala His Ser Leu Asn Ser Pro Pro Arg Leu Ser
1               5                   10

<210> SEQ ID NO 114
<211> LENGTH: 8
<212> TYPE: PRT
<213> ORGANISM: Homo sapiens

<400> SEQUENCE: 114

His Ser Lys Phe His Pro Lys Leu
1               5
```